US009555136B2

(12) United States Patent
Khandhar et al.

(10) Patent No.: US 9,555,136 B2
(45) Date of Patent: Jan. 31, 2017

(54) COATED MAGNETIC NANOPARTICLES

(71) Applicant: University of Washington through its Center for Commercialization, Seattle, WA (US)

(72) Inventors: Amit P. Khandhar, Seattle, WA (US); Kannan M. Krishnan, Seattle, WA (US); R. Matthew Ferguson, Seattle, WA (US); Scott Kemp, Seattle, WA (US)

(73) Assignee: University of Washington through its Center for Commercialization, Seattle, WA (US)

(*) Notice: Subject to any disclaimer, the term of this patent is extended or adjusted under 35 U.S.C. 154(b) by 0 days.

(21) Appl. No.: 15/043,313

(22) Filed: Feb. 12, 2016

(65) Prior Publication Data

US 2016/0158387 A1 Jun. 9, 2016

Related U.S. Application Data

(63) Continuation-in-part of application No. 13/805,763, filed as application No. PCT/US2011/041090 on Jun. 20, 2011, now Pat. No. 9,259,492, application No. 15/043,313, which is a continuation-in-part of application No. PCT/US2014/067410, filed on Nov. 25, 2014.

(60) Provisional application No. 61/356,892, filed on Jun. 21, 2010, provisional application No. 61/441,933, filed on Feb. 11, 2011, provisional application No. 61/908,563, filed on Nov. 25, 2013.

(51) Int. Cl.
*A61K 49/18* (2006.01)
*A61K 41/00* (2006.01)
*A61N 2/00* (2006.01)
*A61B 5/05* (2006.01)

(52) U.S. Cl.
CPC ............ *A61K 49/1857* (2013.01); *A61B 5/05* (2013.01); *A61K 41/0052* (2013.01); *A61N 2/004* (2013.01)

(58) Field of Classification Search
CPC A61K 49/1857; A61K 41/0052; A61N 2/004; A61B 5/05; Y10T 428/2982
USPC ......................................................... 428/403
See application file for complete search history.

(56) References Cited

U.S. PATENT DOCUMENTS

| 7,128,891 | B1 | 10/2006 | Sun |
| 8,383,085 | B2 | 2/2013 | Hegmann |
| 9,259,492 | B2* | 2/2016 | Krishnan ........... A61K 41/0052 |
| 2002/0098529 | A1 | 7/2002 | Tan et al. |
| 2003/0085703 | A1 | 5/2003 | Gleich |
| 2005/0130167 | A1* | 6/2005 | Bao .................. A61K 49/0002 435/6.12 |
| 2006/0133990 | A1 | 6/2006 | Hyeon et al. |
| 2006/0286379 | A1* | 12/2006 | Gao ................. G01N 33/54326 428/403 |
| 2007/0014730 | A1 | 1/2007 | Briel |
| 2007/0036729 | A1 | 2/2007 | Briel |
| 2007/0258888 | A1 | 11/2007 | Feldmann |
| 2009/0196831 | A1* | 8/2009 | Yang ................. A61K 49/0032 424/9.322 |
| 2009/0324494 | A1* | 12/2009 | Ham ................. A61K 41/0052 424/1.65 |
| 2010/0012880 | A1 | 1/2010 | Rampersaud |
| 2013/0095043 | A1 | 4/2013 | Burdinski |
| 2013/0149539 | A1 | 6/2013 | Krishnan |
| 2014/0170078 | A1 | 6/2014 | Hyeon et al. |
| 2016/0136307 | A1 | 5/2016 | Wei et al. |

FOREIGN PATENT DOCUMENTS

| JP | 09-502958 A | 3/1997 |
| JP | 2005-504888 A | 2/2005 |
| JP | 2006-525506 A | 11/2006 |
| JP | 2008-519744 A | 6/2008 |
| JP | 2008-169110 A | 7/2008 |
| JP | 2008-544968 A | 12/2008 |
| JP | 2009-195614 A | 9/2009 |
| JP | 2009-531296 A | 9/2009 |
| JP | 2009-233845 A | 10/2009 |

(Continued)

OTHER PUBLICATIONS

Ahmad, S., et al., "Cholesterol Interferes With the MTT Assay in Human Epithelial-Like (A549) and Endothelial (HLMVE and HCAE) Cells," International Journal of Toxicology 25(1)17-23, Jan.-Feb. 2006.
Allémann, E., et al., "Drug-Loaded Nanoparticles—Preparation Methods and Drug Targeting Issues," European Journal of Pharmaceutics and Biopharmaceutics 39(5):173-191, 1993.
Allen, T.M., "Ligand-Targeted Therapeutics in Anticancer Therapy," Nature Reviews: Cancer 2(10):750-763, Oct. 2002.

(Continued)

*Primary Examiner* — Leszek Kiliman
(74) *Attorney, Agent, or Firm* — Christensen O'Connor Johnson Kindness PLLC

(57) ABSTRACT

Disclosed herein are polymer-coated iron oxide magnetic nanoparticles and methods of their manufacture and use. The nanoparticles are coated with a copolymer of poly(maleic anhydride alt-H2C=CH—R1)-polyethylene glycol (PMAR-PEG), wherein R1 is a hydrophobic moiety. The molecular weights of the PMAR and PEG portions of the copolymer, as well as the core diameter of the nanoparticles are selected in order to produce optimal performance for specific applications. Representative applications of the nanoparticles include magnetic particle imaging, magnetic sentinel lymph node biopsy, and magnetic fluid hyperthermia. The disclosed nanoparticles are tools for these methods that provide previously unachieved levels of stability (e.g., via reduced agglomeration) and customizability (e.g., tuned blood circulation half-life in vivo).

22 Claims, 23 Drawing Sheets

(56) References Cited

FOREIGN PATENT DOCUMENTS

| WO | 97/25073 A2 | 7/1997 |
|---|---|---|
| WO | 2009/109588 A2 | 9/2009 |
| WO | 2010/067264 A1 | 6/2010 |
| WO | 2012/018240 A2 | 2/2012 |

OTHER PUBLICATIONS

Andrä, W., et al., "Application of Magnetic Particles in Medicine and Biology," in H. Kronmüller and S. Parkin (eds.), "Handbook of Magnetism and Advanced Magnetic Materials," Wiley, Chichester, U.K., 2007, vol. 4, pp. 2536-2568.
Aoki, I., et al., "In Vivo Detection of Neuroarchitecture in the Rodent Brain Using Manganese-Enhanced MRI," NeuroImage 22(3):1046-1059, Jul. 2004.
Bacon, B.R., et al., "Ferrite Particles: A New Magnetic Resonance Imaging Contrast Agent. Lack of Acute or Chronic Hepatotoxicity After Intravenous Administration," Journal of Laboratory and Clinical Medicine 110(2):164-171, Aug. 1987.
Bao, Y., and K.M. Krishnan, "Preparation of Functionalized and Gold-Coated Cobalt Nanocrystals for Biomedical Applications," Journal of Magnetism and Magnetic Materials 293(1)15-19, May 2005.
Bao, Y., et al., "Brownian Magnetic Relaxation of Water-Based Cobalt Nanoparticles," Journal of Applied Physics 99(8):08H107-1-08H107-3, Apr. 2006.
Bao, Y., et al., "Controlled Crystalline Structure and Surface Stability of Cobalt Nanocrystals," Journal of Applied Physics 109(15):7220-7222, Apr. 2005.
Bao, Y., et al., "Controlled Self-Assembly of Colloidal Cobalt Nanocrystals Mediated by Magnetic Interactions," Journal of Magnetism and Magnetic Materials 272-276(Suppl.):E1367-E1368, May 2004.
Bao, Y., et al., "A General Approach to Synthesis of Nanoparticles With Controlled Morphologies and Magnetic Properties," Journal of Applied Physics 97(10):10J317-1-10J317-3, May 2005.
Bao, Y., et al., "Synthesis and Characterization of Magnetic-Optical Co—Au Core-Shell Nanoparticles," Journal of Physical Chemistry C 111(5):1941-1944, Feb. 2007.
Bao, Y.P., "Synthesis, Self-Assembly and Potential Applications of Cobalt-Based Nanoparticles With Tailored Magnetic Properties," doctoral dissertation, University of Washington, Seattle, 2006, 189 pages.
Bao, Y.P., et al., "The Critical Role of Surfactants in the Growth of Cobalt Nanoparticles," Langmuir 26(1):478-483, Jan. 2009.
Baselt, D.R., et al., "A Biosensor Based on Magnetoresistance Technology," Biosensors and Bioelectronics 13(7-8):731-739, Oct. 1998.
Bean, C.P., "Hysteresis Loops of Mixtures of Ferromagnetic Micropowders," Journal of Applied Physics 26(11):1381-1383, Nov. 1955.
Bedanta, S., and W. Kleemann, "Supermagnetism," Journal of Physics D: Applied Physics 42(1):013001, Jan. 2009, 28 pages.
Bengele, H.H., et al., "Biodistribution of an Ultrasmall Superparamagnetic Iron Oxide Colloid, BMS 180549, by Different Routes of Administration," Magnetic Resonance Imaging 12(3):433-442, 1994.
Bertone, V., et al., "Hyperthermic Effect on the Human Metastatic Liver: A TEM Study," Anticancer Research 17(6D):4713-4716, Nov.-Dec. 1997.
Blakemore, R., "Magnetotactic Bacteria," Science 190(4212):377-379, Oct. 1975.
Bouck, N., et al., "How Tumors Become Angiogenic," Advances in Cancer Research 69:135-174, 1996.
Boyles, J., and D.F. Bainton, "Changes in Plasma-Membrane-Associated Filaments During Endocytosis and Exocytosis in Polymorphonuclear Leukocytes," Cell 24(3):906-914, Jun. 1981.

Brezovich, I.A., "Low Frequency Hyperthermia: Capacitive and Ferromagnetic Thermoseed Methods," Medical Physics Monograph 16:82-111, Jan. 1988.
Brigger, I., et al., "Nanoparticles in Cancer Therapy and Diagnosis," Advances in Drug Delivery Reviews 54(5):631-651, Sep. 2002.
Bucak, S., et al., "Protein Separations Using Colloidal Magnetic Nanoparticles," Biotechnology Progress 19(2):477-484, Mar.-Apr. 2003.
Buffat, P., and J.-P. Borel, "Size Effect on the Melting Temperature of Gold Particles," Physical Review A 13(6):2287-2298, Jun. 1976.
Bull, J.M.C., "An Update on the Anticancer Effects of a Combination of Chemotherapy and Hyperthermia," Cancer Research 44(10 Suppl.):4853-4856, Oct. 1984.
Bulte, J.W.M., et al., "Preparation, Relaxometry, and Biokinetics of PEGylated Magnetoliposomes as MR Contrast Agent," Journal of Magnetism and Magnetic Materials 194(1-3):204-209, Apr. 1999.
Bulte, J.W.M., et al., "Specific MR Imaging of Human Lymphocytes by Monoclonal Antibody-Guided Dextran-Magnetite Particles," Magnetic Resonance in Medicine 25(1):148-157, May 1992.
Carmichael, J., et al., "Evaluation of a Tetrazolium-Based Semiautomated Colorimetric Assay: Assessment of Chemosensitivity Testing," Cancer Research 47(4):936-942, Feb. 1987.
Cengelli, F., et al., "Interaction of Functionalized Superparamagnetic Iron Oxide Nanoparticles With Brain Structures," Journal of Pharmacology and Experimental Therapeutics 318(1):108-116, Jul. 2006.
Chandaroy, P., et al., "Utilizing Temperature-Sensitive Association of Pluronic F-127 With Lipid Bilayers to Control Liposome-Cell Adhesion," Biochimica et Biophysica Acta 1559(1):32-42, Feb. 2002.
Chantrell, R., et al., "Measurements of Particle Size Distribution Parameters in Ferrofluids," IEEE Transactions on Magnetics 14(5):975-977, Sep. 1978.
Chatterji, T., et al., "Antiferromagnetic Spin Correlations in MnO Nanoparticles," Journal of Magnetism and Magnetic Materials 322(21):3333-3336, Nov. 2010.
Chieh, J.J., et al., "Hyper-High-Sensitivity Wash-Free Magnetoreduction Assay on Biomolecules Using High-Tc Superconducting Quantum Interference Devices," Journal of Applied Physics 103(1):014703-1-014703-6, Jan. 2008.
Cho, S.-J., et al., "Characterization and Magnetic Properties of Core/Shell Structured Fe/Au Nanoparticles," Journal of Applied Physics 95(11):6804-6806, Jun. 2004.
Chou, S.Y., et al., "Imprint Lithography With 25-Nanometer Resolution," Science 272(5258):85-87, Apr. 1996.
Chou, S.Y., et al., "Nanoimprint Lithography," Journal of Vacuum Science and Technology B: Microelectronics and Nanometer Structures 14(6):4129-4133, Nov. 1996.
Christophi, C., et al., "The Treatment of Malignancy by Hyperthermia," Surgical Oncology 7(1-2):83-90, Jul.-Aug. 1999.
Chung, S.H., et al., "Biological Sensors Based on Brownian Relaxation of Magnetic Nanoparticles," Applied Physics Letters 85(14):2971-2973, Oct. 2004.
Cikes, M., "Relationship Between Growth Rate, Cell Volume, Cell Cycle Kinetics, and Antigenic Properties of Cultured Murine Lymphoma Cells," Journal of the National Cancer Institute 45(5):979-988, Nov. 1970.
Connolly, J., and T.G. St. Pierre, "Proposed Biosensors Based on the Time-Dependent Properties of Magnetic Fluids," Journal of Magnetism and Magnetic Materials 225(1-2):156-160, Jan. 2001.
Couzin, J., "Nanoparticles Cut Tumors' Supply Lines," Science 296(5577):2314-2315, Jun. 2002.
Crew, D.C., et al., "Magnetic Interactions and Reversal Behavior of $Nd_2Fe_{14}B$ Particles Diluted in a Nd Matrix," Physical Review B 66(18):184418-1-184418-13, Nov. 2002.
Crossgrove, J., and W. Zheng, "Manganese Toxicity Upon Overexposure," NMR in Biomedicine 17(8):544-553, Dec. 2004.
Dahl, O., "Interaction of Hyperthermia and Chemotherapy," Recent Results in Cancer Research 107:157-169, 1988.
De Almeida, J.R.L., and D.J. Thouless, "Stability of the Sherrington-Kirkpatrick Solution of a Spin Glass Model," Journal of Physics A: Mathematical and General 11(5):983-990, May 1978.

(56) References Cited

OTHER PUBLICATIONS

De Cuyper, M., and M. Joniau, "Magnetoliposomes: Formation and Structural Characterization," European Biophysics Journal 15(5):311-319, Feb. 1988.
De Palma, R., et al., "Silane Ligand Exchange to Make Hydrophobic Superparamagnetic Nanoparticles Water-Dispersible," Chemistry of Materials 19(7):1821-1831, Apr. 2007.
Decker, T., and M.-L. Lohmann-Matthes, "A Quick and Simple Method for the Quantitation of Lactate Dehydrogenase Release in the Measurements of Cellular Cytotoxicity and Tumor Necrosis Factor (TNF) Activity," Journal of Immunological Methods 115(1):61-69, Nov. 1988.
Denizot, F., and R. Lang, "Rapid Colorimetric Assay for Cell Growth and Survival: Modifications to the Tetrazolium Dye Procedure Giving Improved Sensitivity and Reliability," Journal of Immunological Methods 89(2):271-277, May 1986.
Dewey, W.C., et al., "Cell Biology of Hyperthermia and Radiation," in R.E. Meyn and H.R. Withers (eds.), "Radiation Biology in Cancer Research," Raven Press, New York, 1980, pp. 589-621.
Dohi, N., et al., "Red Blood Cell-Mimicking Synthetic Biomaterial Particles," Proceedings of the National Academy of Sciences of the USA (PNAS) 106(51):21495-21499, Dec. 2009.
Eberbeck, D., et al., "Evidence of Aggregates of Magnetic Nanoparticles in Suspensions Which Determine the Magnetisation Behaviour," in T.M. Buzug et al. (eds.), "Magnetic Nanoparticles: Particle Science, Imaging Technology and Clinical Applications: Proceedings of the First International Workshop on Magnetic Particle Imaging," World Scientific Publishing, Hackensack, N.J., Aug. 2010, pp. 66-72.
Edelstein, R.L., et al., "The BARC Biosensor Applied to the Detection of Biological Warfare Agents," Biosensors and Bioelectronics 14(10-11):805-813, Jan. 2000.
Euliss, Le, et al., "Cooperative Assembly of Magnetic Nanoparticles and Block Copolypeptides in Aqueous Media," Nano Letters 3(11):1489-1493, Nov. 2003.
Fahlvik, A.K., et al., "Iron Oxides as MR Imaging Contrast Agents," Journal of Magnetic Resonance Imaging 3(1):187-194, Jan.-Feb. 1993.
Falicov, L.M., "Surface, Interface, and Thin-Film Magnetism," Journal of Materials Research 5(6):1299-1340, Jun. 1990.
Flakenhagen, D., "Small Particles in Medicine," Artificial Organs 19(8):792-794, Aug. 1995.
Ferguson, R.M., et al., "Optimization of Nanoparticle Core Size for Magnetic Particle Imaging," Journal of Magnetism and Magnetic Materials 321(10):1548-1551, May 2009.
Ferguson, R.M., et al., "Optimizing Magnetite Nanoparticles for Mass Sensitivity in Magnetic Particle Imaging," Medical Physics 38(3):1619-1626, Mar. 2011.
Ferguson, R.M., et al., "Size-Optimized Magnetite Nanoparticles for Magnetic Particle Imaging," in T.M. Buzug et al. (eds.), "Magnetic Nanoparticles: Particle Science, Imaging Technology, and Clinical Applications: Proceedings of the First International Workshop on Magnetic Particle Imaging," World Scientific Publishing, Singapore, 2010, pp. 53-59.
Ferrari, M., "Cancer Nanotechnology: Opportunities and Challenges," Nature Reviews: Cancer 5(3):161-171, Mar. 2005.
Feri, E.H., et al., "Critical Size and Nucleation Field of Ideal Ferromagnetic Particles," Physical Review 106(3):446-455, May 1957.
Fritz, T., et al., "Detailed Toxicity Studies of Liposomal Gadolinium-DTPA," Investigative Radiology 26(11):960-968, Nov. 1991.
Fujii, T., and T. Kaito, "Nano Factory Achieved by Focused Ion Beam," Microscopy and Microanalysis 11(Suppl. 2):810-811, Aug. 2005.
Gao, Y., et al., "Spiral Spin Order of Self-Assembled Co Nanodisk Arrays," Physical Review Letters 96(13):137205-1-137205-4, Apr. 2006.
Gao, Y., et al., "Superstructures of Self-Assembled Cobalt Nanocrystals," Applied Physics Letters 84(17):3361-3363, Apr. 2004.
Geraldes, C.F.G.C., and S. Laurent, "Classification and Basic Properties of Contrast Agents for Magnetic Resonance Imaging," Contrast Media and Molecular Imaging 4(1):1-23, Jan.-Feb. 2009.
Gerner, E.W., and M.J. Schneider, "Induced Thermal Resistance in HeLa Cells," Nature 256(5517):500-502, Aug. 1975.
Gerweck, L.E., "Modification of Cell Lethality at Elevated Temperatures: The pH Effect," Radiation Research 70(1):224-235, Apr. 1977.
Gijs, M.A.M., "Magnetic Bead Handling On-Chip: New Opportunities for Analytical Applications," Microfluidics and Nanofluidics 1(1):22-40, Nov. 2004.
Gilchrist, R.K., et al., "Selective Inductive Heating of Lymph Nodes," Annals of Surgery 146(4):596-606, Oct. 1957.
Gilmour, P.S., et al., "Pulmonary and Systemic Effects of Short-Term Inhalation Exposure to Ultrafine Carbon Black Particles," Toxicology and Applied Pharmacology 195(1):35-44, Feb. 2004.
Gleich, B., and J. Weizenecker, "Tomographic Imaging Using the Nonlinear Response of Magnetic Particles," Nature 435(7046):1214-1217, Jun. 2005.
Gleich, B., et al., "Experimental Results on Fast 2D-Encoded Magnetic Particle Imaging," Physics in Medicine and Biology 53(6):N81-N84, Mar. 2008.
Gonzales, M., and K.M. Krishnan, "Phase Transfer of Highly Monodisperse Iron Oxide Nanocrystals With Pluronic F127 for Biomedical Applications," Journal of Magnetism and Magnetic Materials 311(1):59-62, Apr. 2007.
Gonzales, M., and K.M. Krishnan, "Synthesis of Magnetoliposomes With Monodisperse Iron Oxide Nanocrystal Cores for Hyperthermia," Journal of Magnetism and Magnetic Materials 293(1):265-270, May 2005.
Gonzales, M., et al., "Cytotoxicity of Iron Oxide Nanoparticles Made From the Thermal Decomposition of Organometallics and Aqueous Phase Transfer With Pluronic F127," Contrast Media and Molecular Imaging 5(5):286-293, Sep.-Oct. 2010. (Author manuscript PMCID: PMC3020093, available in PMC Sep. 1, 2011, 18 pages.).
Gonzales-Weyhmiller, M., "Synthesis, Modeling and Optimization of Iron Oxide Nanoparticles for Magnetic Fluid Hyperthermia," doctoral dissertation, University of Washington, Seattle, 2007, 188 pages.
Goodwill, P., and S. Conolly, "The X-Space Formulation of the Magnetic Particle Imaging Process: 1-D Signal, Resolution, Bandwidth, SNR, SAR, and Magnetostimulation," IEEE Transactions on Medical maging 29(11):1851-1859, Nov. 2010.
Griffin, K.A., et al., "Intrinsic Ferromagnetism in Insulating Cobalt Doped Anatase $TiO_2$," Physical Review Letters 94(15):157204-1-157204-4, Apr. 2005.
Gupta, A.K., and M. Gupta, "Synthesis and Surface Engineering of Iron Oxide Nanoparticles for Biomedical Applications," Biomaterials 26(18):3995-4021, Jun. 2005.
Häfeli, U.O., et al., "The Biocompatibility and Toxicity of Magnetic Particles," in M. Zborowski and J.J. Chalmers (eds.), "Magnetic Cell Separation," Elsevier, Amsterdam, 2008, vol. 32, Chap. 7, pp. 163-223.
Häfeli, U.O., et al., "Cell Uptake and In Vitro Toxicity of Magnetic Nanoparticles Suitable for Drug Delivery," Molecular Pharmaceutics 6(5):1417-1428, Sep.-Oct. 2009.
Häfeli, U.O., "Magnetic Nano and Microparticles for Targeted Drug Delivery," in R. Arshady and K. Kono (eds.), "Smart Nanoparticles in Nanomedicine," MML Series, Kentus Books, London, 2006, vol. 8, pp. 77-126.
Hahn, G.M., "Comparison of the Malignant Potential of 10T½ Cells and Transformants With Their Survival Responses to Hyperthermia and to Amphotericin B," Cancer Research 40(10):3763-3767, Oct. 1980.
Hahn, G.M., "Hyperthermia for the Engineer: A Short Biological Primer," IEEE Transactions on Biomedical Engineering 31(1):3-8, Jan. 1984.

(56) References Cited

OTHER PUBLICATIONS

Hamm, B., et al., "Contrast Enhanced MR Imaging of Liver and Spleen: First Experience in Humans With a New Superparamagnetic Iron Oxide," Journal of Magnetic Resonance Imaging 4(5):659-668, Sep. 1994.
Hanahan, D., and R.A. Weinberg, "The Hallmarks of Cancer," Cell 100(1):57-70, Jan. 2000.
Harika, L., et al., "Macromolecular Intravenous Contrast Agent for MR Lymphography: Characterization and Efficacy Studies," Radiology 198(2):365-370, Feb. 1996.
Harisinghani, M.G., et al., "Noninvasive Detection of Clinically Occult Lymph-Node Metastases in Prostate Cancer," New England Journal of Medicine 348(25):2491-2499, Jun. 2003.
Hendrick, R.E., and E.M. Haacke, "Basic Physics of MR Contrast Agents and Maximization of Image Contrast," Journal of Magnetic Resonance Imaging 3(1):137-148, Jan.-Feb. 1993.
Henle, K.J., "Sensitization to Hyperthermia Below 43° C. Induced in Chinese Hamster Ovary Cells by Step-Down Heating," 64(6):1479-1483, Jun. 1980.
Henle, K.J., and D.B. Leeper, "Interaction of Hyperthermia and Radiation in CHO Cells: Recovery Kinetics," Radiation Research 66(3):505-518, Jun. 1976.
Herzer, G., "Grain Structure and Magnetism of Nanocrystalline Ferromagnets," IEEE Transactions on Magnetics 25 (5):3327-3329, Sep. 1989.
Heyn, C., et al., "Detection Threshold of Single SPIO-Labeled Cells With FIESTA," Magnetic Resonance in Medicine 53(2):312-320, Feb. 2005.
Himpsel, F.J., et al., "Magnetic Nanostructures," Advances in Physics 47(4):511-597, 1998.
Hoffman, A.S., and P.S. Stayton, "Bioconjugates of Smart Polymers and Proteins: Synthesis and Applications," Macromolecular Symposia 207(1):139-151, Feb. 2004.
Hood, J.D., et al., "Tumor Regression by Targeted Gene Delivery to the Neovasculature," Science 296(5577):2404-2407, Jun. 2002.
Horák, D., et al., "Preparation and Properties of Magnetic Nano- and Microsized Particles for Biological and Environmental Separations," Journal of Separation Sciences 30(11):1751-1772, Jul. 2007.
Housini, A., and R. Narain, "Aqueous Solution Behavior of P(N-isopropyl acrylamide) in the Presence of Water-Soluble Macromolecular Species," European Polymer Journal 43(10):4344-4354, Oct. 2007.
Hu, F., et al., "Cellular Response to Magnetic Nanoparticles 'PEGylated' via Surface-Initiated Atom Transfer Radical Polymerization," Biomacromolecules 7(3):809-816, Mar. 2006.
Hu, W., et al., "High-Moment Antiferromagnetic Nanoparticles With Tunable Magnetic Properties," Advanced Materials 20(8):1479-1481, Apr. 2008.
Hu, W., et al., "Patterning of High Density Magnetic Nanodot Arrays by Nanoimprint Lithography," Journal of Vacuum Science & Technology A 25(4):1294-1297, Jul. 2007.
Hyeon, T., "Chemical Synthesis of Magnetic Nanoparticles," Chemical Communications 21(8):927-934, Apr. 2003.
Hyeon, T., et al., "Synthesis of Highly Crystalline and Monodisperse Maghemite Nanocrystallites Without a Size-Selection Process," Journal of the American Chemical Society 123(51):12798-12801, Dec. 2001.
Inouye, K., et al., "Oxygenation of Ferrous Ions in Reversed Micelle and Reversed Microemulsion," Journal of Physical Chemistry 86(8):1465-1469, Apr. 1982.
International Search Report and Written Opinion dated Mar. 28, 2012, issued in corresponding International Application No. PCT/US2011/041090, filed Jun. 20, 2011, 10 pages.
International Search Report and Written Opinion mailed Feb. 20, 2015, issued in corresponding International Application No. PCT/US2014/067410, filed Nov. 25, 2014, 7 pages.
Ito, A., et al., "Augmentation of MHC Class I Antigen Presentation via Heat Shock Protein Expression by Hyperthermia," Cancer Immunology, Immunotherapy 50(10):515-522, Dec. 2001.
Ito, A., et al., "Heat Shock Protein 70 Expression Induces Antitumor Immunity During Intracellular Hyperthermia Using Magnetite Nanoparticles," Cancer Immunology, Immunotherapy 52(2):80-88, Feb. 2003.
Ito, A., et al., "Medical Application of Functionalized Magnetic Nanoparticles," Journal of Bioscience and Bioengineering 100(1):1-11, Jul. 2005.
Jain, R.K., "Delivery of Molecular and Cellular Medicine to Solid Tumors," Advanced Drug Delivery Reviews 46(1-3):149-168, Mar. 2001.
Jain, R.K., "The Next Frontier of Molecular Medicine: Delivery of Therapeutics," Nature Medicine 4(6):655-657, Jun. 1998.
Jana, N.R., et al., "Size- and Shape-Controlled Magnetic (Cr, Mn, Fe, Co, Ni) Oxide Nanocrystals via a Simple and General Approach," Chemistry of Materials 16(20):3931-3935, Oct. 2004.
Johnsen, S., and K.J. Lohmann, "The Physics and Neurobiology of Magnetoreception," Nature Reviews: Neuroscience 6(9):703-712, Sep. 2005.
Jordan, A., et al., "Arrhenius Analysis of the Thermal Response of Human Colonic Adenocarcinoma Cells In Vitro Using the Multi-Target, Single-Hit and the Linear-Quadratic Model," International Journal of Hyperthermia 13(1):83-88, Jan.-Feb. 1997.
Jordan, A., et al., "Magnetic Fluid Hyperthermia (MFH): Cancer Treatment With AC Magnetic Field Induced Excitation of Biocompatible Superparamagnetic Nanoparticles," Journal of Magnetism and Magnetic Materials 201(1-3):413-419, Jul. 1999.
Josephson, L., et al., "The Effects of Iron Oxide on Proton Relaxivity," Magnetic Resonance Imaging 6(6):647-653, Nov.-Dec. 1988.
Kabalka, G.W., et al., "Gadolinium-Labeled Liposomes Containing Various Amphiphilic Gd-DTPA Derivatives: Targeted MRI Contrast Enhancement Agents for the Liver," Magnetic Resonance in Medicine 19(2):406-415, Jun. 1991.
Kalele, S., et al., "Probing Temperature-Sensitive Behavior of pNIPAAm-Coated Iron Oxide Nanoparticles Using Frequency-Dependent Magnetic Measurements," Journal of Magnetism and Magnetic Materials 321(10):1377-1380, May 2009.
Kang, Y.S., et al., "Synthesis and Characterization of Nanometer-Size $Fe_3O_4$ and $\gamma$-$Fe_2O_3$ Particles," Chemistry of Materials 8(9):2209-2211, Sep. 1996.
Kaplan, P.D., et al., "Entropically Driven Surface Phase Separation in Binary Colloidal Mixtures," Physical Review Letters 72(4):582-585, Jan. 1994.
Kashchiev, D., "Nucleation: Basic Theory With Applications," Butterworth-Heineman, Oxford, U.K., 2000, pp. 33-35; 293-306.
Kashchiev, D., and G.M. Van Rosmalen, "Review: Nucleation in Solutions Revisited," Crystal Research and Technology 38(7-8):555-574, Jul. 2003.
Katz, E., and I. Willner, "Integrated Nanoparticle-Biomolecule Hybrid Systems: Synthesis, Properties, and Applications," Angewandte Chemie International Edition 43(45):6042-6108, Nov. 2004.
Kircher, M.F., et al., "A Multimodal Nanoparticle for Preoperative Magnetic Resonance Imaging and Intraoperative Optical Brain Tumor Delineation," Cancer Research 63(23):8122-8125, Dec. 2003.
Kirsch, J.E., "Basic Principles of Magnetic Resonance Contrast Agents," Topics in Magnetic Resonance maging 3(2):1-18, Mar. 1991.
Kittel, C., "Physical Theory of Ferromagnetic Domains," Reviews of Modern Physics 21(4):541-583, Oct. 1949.
Klem, M.T., et al., "Bio-Inspired Synthesis of Protein-Encapsulated CoPt Nanoparticles," Advanced Functional Materials 15(9):1489-1494, Sep. 2005.
Klem, M.T., et al., "Biomimetic Magnetic Nanoparticles," Materials Today 8(9):28-37, Sep. 2005.
Klibanov, A.L., et al., "Activity of Amphipathic Poly(ethylene glycol) 5000 to Prolong the Circulation Time of Liposomes Depends on the Liposome Size and is Unfavorable for Immunoliposome Binding to Target," Biochimica et Biophysica Acta (BBA)—Biomembranes 1062(2):142-148, Feb. 1991.
Klibanov, A.L., et al., "Amphipathic Polyethyleneglycols Effectively Prolong the Circulation Time of Liposomes," FEBS Letters 268(1):235-237, Jul. 1990.

(56) References Cited

OTHER PUBLICATIONS

Klie, R.F., and N.D. Browning, "Characterization of Oxygen Ordering in (La, Sr)FeO(3-δ) by Atomic Resolution Z-Contrast Imaging and Electron Energy-Loss Spectroscopy," Journal of Electron Microscopy 51(Suppl. 1):S59-S66, Mar. 2002.

Kötitz, R., et al., "Determination of the Binding Reaction Between Avidin and Biotin by Relaxation Measurements of Magnetic Nanoparticles," Journal of Magnetism and Magnetic Materials 194(1-3):62-68, Apr. 1999.

Kramer, R.M., et al., "Engineered Protein Cages for Nanomaterial Synthesis," Journal of the American Chemical Society 126(41):13282-13286, Oct. 2004.

Kreuter, J., "Nanoparticle-Based Drug Delivery Systems," Journal of Controlled Release 16(1-2):169-176, Jun.-Jul. 1991.

Kreyling, W.G., et al., "Health Implications of Nanoparticles," Journal of Nanoparticle Research 8(5):543-562, Oct. 2006.

Krishnan, K.M., "Atomic Site and Species Determinations Using Channeling and Related Effects in Analytical Electron Microscopy," Ultramicroscopy 24(2-3):125-141, 1988.

Krishnan, K.M., "Biomedical Nanomagnetics: A Spin Through Possibilities in Imaging, Diagnostics, and Therapy," IEEE Transactions on Magnetics 46(7):2523-2558, Jul. 2010.

Krishnan, K.M., "Iron$_{3,2}$ Near-Edge Fine Structure Studies," Ultramicroscopy 32(4):309-311, May-Jun. 1990.

Krishnan, K.M., et al., "Crystallographic Site-Occupancy Refinements in Thin-Film Oxides by Channelling-Enhanced Microanalysis," Acta Crystallographica Section B 41(6):396-405, Dec. 1985.

Krishnan, K.M., et al., "Nanomagnetism and Spin Electronics: Materials, Microstructure and Novel Properties," Journal of Materials Science 41(3):793-815, Feb. 2006.

LaMer, V.K., and R.H. Dinegar, "Theory, Production and Mechanism of Formation of Monodispersed Hydrosols," Journal of the American Chemical Society 72(11):4847-4854, Nov. 1950.

Lang, C., and D. Schuler, "Biogenic Nanoparticles: Production, Characterization, and Application of Bacterial Magnetosomes," Journal of Physics: Condensed Matter 18(38):S2815-S2828, Sep. 2006.

Lang, C., et al., "Synthesis of Magnetite Nanoparticles for Bio- and Nanotechnology: Genetic Engineering and Biomimetics of Bacterial Magnetosomes," Macromolecular Bioscience 7(2):144-151, Feb. 2007.

Langer, R., "Drug Delivery and Targeting," Nature 392(6679 Suppl.):5-10, Apr. 1998.

Larson, D.R., et al., "Water-Soluble Quantum Dots for Multiphoton Fluorescence Imaging In Vivo," Science 300(5624):1434-1436, May 2003.

Larsson, K., et al., "Magnetic Transducers in Biosensors and Bioassays," Analusis 27(7):617-621, Sep. 1999.

Lauffer, R.B., "Paramagnetic Metal Complexes as Water Proton Relaxation Agents for NMR Imaging: Theory and Design," Chemical Reviews 87(5):901-927, Oct. 1987.

Lee, Y.-C., et al., "Size-Driven Magnetic Transitions in Monodisperse MnO Nanocrystals," Journal of Applied Physics 107(9):09E124-1-09E124-3, May 2010.

Legrand, C., et al., "Lactate Dehydrogenase (LDH) Activity of the Number of Dead Cells in the Medium of Cultured Eukaryotic Cells as Marker," Journal of Biotechnology 25(3):231-243, Sep. 1992.

Leslie-Pelecky, D.L., and R.D. Rieke, "Magnetic Properties of Nanostructured Materials," Chemistry of Materials 8(8):1770-1783, Aug. 1996.

Li, G.C., et al., "Heat Shock Proteins, Thermotolerance, and Their Relevance to Clinical Hyperthermia," International Journal of Hyperthermia 11(4):459-488, Jul.-Aug. 1995.

Li, K.C.P., et al., "Molecular Imaging Applications in Nanomedicine," Biomedical Microdevices 6(2):113-116, Jun. 2004.

Lim, J.K., et al., "Synthesis and Single-Particle Optical Detection of Low-Polydispersity Plasmonic-Superparamagnetic Nanoparticles," Advanced Materials 20(9):1721-1726, May 2008.

Lin, J., et al., "Gold-Coated Iron (Fe@Au) Nanoparticles: Synthesis, Characterization, and Magnetic Field Induced-Self-Assembly," Journal of Solid State Chemistry 159(1):26-31, Jun. 2001.

Liu, Q., et al., "Novel Two-Step Silica-Coating Process for Engineering Magnetic Nano Composites," Chemistry of Materials 10(12):3936-3940, Dec. 1998.

Lyon, J.L., et al., "Synthesis of Fe Oxide Core/Au Shell Nanoparticles by Iterative Hydroxylamine Seeding," Nano Letters 4(4):719-723, Apr. 2004.

Mazer-Hauff, K., et al., "Intracranial Thermotherapy Using Magnetic Nanoparticles Combined With External Beam Radiotherapy: Results of a Feasability Study on Patients With Glioblastoma Multiforme," Journal of Neuro-Oncology 81(1):53-60, Jan. 2007.

Mandal, S., and K.M. Krishnan, "Co(core)AU(shell) Nanoparticles: Evolution of Magnetic Properties in the Displacement Reaction," Journal of Materials Chemistry 17(4):372-376, 2007.

Marshall, E., "Setbacks for Endostatin," Science 295(5563):2198-2199, Mar. 2002.

Massoud, T.F., and S.S. Gambhir, "Molecular Imaging in Living Subjects: Seeing Fundamental Biological Processes in a New Light," Genes and Development 17(5):545-580, Mar. 2003.

Matsumura, Y., and H. Maeda, "A New Concept for Macromolecular Therapeutics in Cancer Chemotherapy: Mechanism of Tumoritropic Accumulation of Proteins and the Antitumor Agent Smancs," Cancer Research 46(12 Pt. 1):6387-6392, Dec. 1986.

Ménoret, A., and R. Chandawarkar, "Heat-Shock Protein-Based Anticancer Immunotherapy: An Idea Whose Time Has Come," Seminars in Oncology 25(6):654-660, Dec. 1998.

Minard, K.R., and R.A. Wind, "Picoliter $^1$H NMR Spectroscopy," Journal of Magnetic Resonance 154(2):336-343, Feb. 2002.

Minard, K.R., and R.A. Wind, "Solenoidal Micocoil Design. Part I: Optimizing Rf Homogeneity and Coil Dimensions," Concepts in Magnetic Resonance 13(2):190-210, Mar. 2001.

Mizejewski, G.J., "Role of Integrins in Cancer: Survey of Expression Patterns," Proceedings of the Society for Experimental Biology and Medicine 222(2):124-138, Nov. 1999.

Morawski, A.M., et al., "Targeted Nanoparticles for Quantitative Imaging of Sparse Molecular Epitopes With MRI," Magnetic Resonance in Medicine 51(3):480-486, Mar. 2004.

Mosmann, T., "Rapid Colorimetric Assay for Cellular Growth and Survival: Application to Proliferation and Cytotoxicity Assays," Journal of Immunological Methods 65(1-2):55-63, Dec. 1983.

Mousa, S.A., et al., "Tetraiodothyroacetic Acid, a Small Molecule Integrin Ligand, Blocks Angiogenesis Induced by Vascular Endothelial Growth Factor and Basic Fibroblast Growth Factor," Angiogenesis 11(2):183-190, Jun. 2008.

Muldoon, L.L., et al., "Imaging, Distribution, and Toxicity of Superparamagnetic Iron Oxide Magnetic Resonance Nanoparticles in the Rat Brain and Intracerebral Tumor," Neurosurgery 57(4):785-796, Oct. 2005.

Murray, C.B., et al., "Colloidal Synthesis of Nanocrystals and Nanocrystal Superlattices," IBM Journal of Research and Development 45(1):47-56, Jan. 2001.

Murray, C.B., et al., "Synthesis and Characterization of Monodisperse Nanocrystals and Close-Packed Nanocrystal Assemblies," Annual Review of Materials Science 30:545-610, Aug. 2000.

Murray, C.B., et al., "Synthesis and Characterization of Nearly Monodisperse CdE (E=S, Se, Te) Semiconductor Nanocrystallites," Journal of the American Chemical Society 115(19):8706-8715, Sep. 1993.

Na, H.B., et al., "Inorganic Nanoparticles for MRI Contrast Agents," Advanced Materials 21(21):2133-2148, Jun. 2009.

Narain, R., et al., "Synthesis of Monodisperse Biotinylated p(NIPAAm)-Coated Iron Oxide Magnetic Nanoparticles and Their Bioconjugation to Streptavidin," Langmuir 23(11):6299-6304, May 2007.

Nelson, K.L, and V.M. Runge, "Basic Principles of MR Contrast," Topics in Magnetic Resonance Imaging 7(3):124-136, Summer 1995.

Netti, P.A., et al., "Time-Dependent Behavior of Interstitial Fluid Pressure in Solid Tumors: Implications for Drug Delivery," Cancer Research 55(22):5451-5458, Nov. 1995.

(56) References Cited

OTHER PUBLICATIONS

Nie, S., et al., "Nanotechnology Applications in Cancer," Annual Review of Biomedical Engineering 9:257-288, Aug. 2007.
Nunn, A.D., et al., "Can Receptors Be Imaged With MRI Agents?" Quarterly Journal of Nuclear Medicine 41(2):155-162, Jun. 1997.
Oesterhelt, F., et al., "Unfolding Pathways of Individual Bacteriorhodopsins," Science 288(5463):143-146, Apr. 2000.
Okuhata, Y., "Delivery of Diagnostic Agents for Magnetic Resonance Imaging," Advanced Drug Delivery Reviews 37(1-3):121-137, Apr. 1999.
Osterfeld, S.J., et al., "Multiplex Protein Assays Based on Real-Time Magnetic Nanotag Sensing," Proceedings of the National Academy of Sciences of the USA (PNAS) 105(52):20637-20640, Dec. 2008.
Overgaard, J., and H.D. Suit, "Time-Temperature Relationship in Hyperthermic Treatment of Malignant and Normal Tissue In Vivo," Cancer Research 39(8):3248-3253, Aug. 1979.
Pamme, N., and C. Wilhelm, "Continuous Sorting of Magnetic Cells via On-Chip Free-Flow Magnetophoresis," Lab on a Chip 6(8):974-980, Aug. 2006.
Pankhurst, Q.A., et al., "Applications of Magnetic Nanoparticles in Biomedicine," Journal of Physics D: Applied Physics 36(13):R167-R181, Jul. 2003.
Park, J., et al., "Synthesis, Characterization, and Magnetic Properties of Uniform-Sized MnO Nanospheres and Nanorods," Journal of Physical Chemistry B 108(36):13594-13593, Sep. 2004.
Park, J., et al., "Ultra-Large-Scale Syntheses of Monodisperse Nanocrystals," Nature Materials 3(12):891-895, Dec. 2004.
Pellegrino, T., et al., "Hydrophobic Nanocrystals Coated With an Amphiphilic Polymer Shell: A General Route to Water Soluble Nanocrystals," Nano Letters 4(4):703-707, Apr. 2004.
Peng, X., et al., "Kinetics of II-VI and III-V Colloidal Semiconductor Nanocrystal Growth: 'Focusing' of Size Distributions," Journal of the American Chemical Society 120(21):5343-5344, Jun. 1998.
Peng, X., et al., "Shape Control of CdSe Nanocrystals," Nature 404(6773):59-61, Mar. 2000.
Perry, M.M., and A.B. Gilbert, "Yolk Transport in the Ovarian Follicle of the Hen (*Gallus domesticus*): Lipoprotein-Like Particles at the Periphery of the Oocyte in the Rapid Growth Phase," Journal of Cell Science 39(1):257-272, Oct. 1979.
Pileni, M.P., "Nanosized Particles Made in Colloidal Assemblies," Langmuir 13(13):3266-3276, Jun. 1997.
Puntes, V.F., and K.M. Krishnan, "Synthesis, Structural Order and Magnetic Behavior of Self-Assembled ε-Co Nanocrystal Arrays," IEEE Transactions on Magnetics 37(4):2210-2212, Jul. 2001.
Puentes, V.F., et al., "Colloidal Nanocrystal Shape and Size Control: The Case of Co," Science 291(5511):2115-2117, Mar. 2001.
Puentes, V.F., et al., "Synthesis of Colloidal Cobalt Nanoparticles With Controlled Size and Shapes," Topics in Catalysis 19(2):145-148, Apr. 2002.
Puentes, V.F., et al., "Synthesis of hcp-Co Nanodisks," Journal of the American Chemical Society 124(43):12874-12880, Oct. 2002.
Pusey, P.N., and W. Van Megen, "Phase Behaviour of Concentrated Suspensions of Nearly Hard Colloidal Spheres," Nature 320(6060):340-342, Mar. 1986.
Puzder, A., et al., "The Effect of Organic Ligand Binding on the Growth of CdSe Nanoparticles Probed by Ab Initio Calculations," Nano Letters 4(12):2361-2365, Dec. 2004.
Reasons for Refusal Notice dated Apr. 14,2015, issued in Japanese Application No. 2013-516656, filed Jun. 20, 2011, 11 pages.
Reiss, B.D., et al., "Biological Routes to Metal Alloy Ferromagnetic Nanostructures," Nano Letters 4(6):1127-1132, Jun. 2004.
Reiss, H., "The Growth of Uniform Colloidal Dispersions," Journal of Chemical Physics 19(4):482-487, Apr. 1951.
Roberts, K.G., et al., "Defect-Mediated Ferromagnetism in Insulating Co-Doped Anatase $TiO_2$ Thin Films," Physical Review B 78(1):014409-1-014409-6, Jul. 2008.

Rockenberger, J., et al., "A New Nonhydrolytic Single-Precursor Approach to Surfactant-Capped Nanocrystals of Transition Metal Oxides," Journal of the American Chemical Society 121(49):11595-11596, Dec. 1999.
Romanus, E., et al., "Magnetic Nanoparticle Relaxation Measurement as a Novel Tool for in Vivo Diagnostics," Journal of Magnetism and Magnetic Materials 252:387-389, Nov. 2002.
Röschmann, P., "Radiofrequency Penetration and Absorption in the Human Body: Limitations to High-Field Whole-Body Nuclear Magnetic Resonance Imaging," Medical Physics 14(6):922-931, Nov.-Dec. 1987.
Rosensweig, R.E., "Heating Magnetic Fluid With Alternating Magnetic Field," Journal of Magnetism and Magnetic Materials 252:370-374, Nov. 2002.
Rosensweig, R.E., "Magnetic Fluids," Scientific American 247(4):136-145, Oct. 1982.
Runge, V.M., et al., "Intravascular Contrast Agents Suitable for Magnetic Resonance Imaging," Radiology 153(1):171-176, Oct. 1984.
Runge, V.M., et al., "Paramagnetic Agents for Contast-Enhanced NMR Imaging: A Review," American Journal of Roentgenology 141(6):1209-1215, Dec. 1983.
Šafarίl, I., and M. Šafarίková, "USe of Magnetic Techniques for the Isolation of Cells," Journal of Chromatography B: Biomedical Sciences and Applications 722(1-2):33-53, Feb. 1999.
Sapieszko, R.S., and E. Matijevic, "Preparation of Well-Defined Colloidal Particles by Thermal Decomposition of Metal Chelates," Journal of Colloid and Interface Science 74(2):405-422, Apr. 1980.
Schlesinger, M.J., "Heat Shock Proteins," Journal of Biological Chemistry 265(21):12111-12114, Jul. 1990.
Schütt, W., et al., "Applications of Magnetic Targeting in Diagnosis and Therapy—Possibilities and Limitations: A Mini-Review," Hybridoma 16(1):109-117, Feb. 1997.
Shapiro, E.M., and A.P. Koretsky, "Convertible Manganese Contrast for Molecular and Cellular MRI," Magnetic Resonance in Medicine 60(2):265-269, Aug. 2008.
Shen, T., et al., "Monocrystalline Iron Oxide Nanoparticles (MION): Physicochemical Properties," Magnetic Resonance in Medicine 29(5):599-604, May 1993.
Shiozawa, M., et al., "Sentinal Lymph Node Biopsy in Patients With Breast Cancer Using Superparamagnetic Iron Oxide and a Magnetometer," Breast Cancer 20(3):223-229, Jul. 2013.
Shliomis, M.I., "Magnetic Fluids," Soviet Physics-Uspekhi 17(2):153-169, Sep.-Oct. 1974.
Silva, A.C., et al., "Manganese-Enhanced Magnetic Resonance Imaging (MEMRI): Methodological and Practical considerations," NMR in Biomedicine 17(8):532-543, Nov.-Dec. 2004.
Silva, G.A., "Nanotechnology Approaches for Drug and Small Molecule Delivery Across the Blood Brain Barrier," Neurosurgery 67(2):113-116, Feb. 2007.
Sjögren, Ce., et al., "Crystal Size and Properties of Superparamagnetic Iron Oxide (SPIO) Particles," Magnetic Resonance Imaging 15(1):55-67, 1997.
Soenen, S.J.H., and M. De Cuyper, "Assessing Cytotoxicity of (Iron Oxide-Based) Nanoparticles: An Overview of Different Methods Exemplified With Cationic Magnetoliposomes," Contrast Media and Molecular Imaging 4(5):207-219, Sep.-Oct. 2009.
Srinivas, P.R., et al., "Nanotechnology in Early Detection of Cancer," Laboratory Investigation 82(5):657-662, May 2002.
Srivastava, P.K., et al., "Heat Shock Proteins Come of Age: Primitive Functions Acquire New Roles in an Adaptive World," Immunity 8(6):657-665, Jun. 1998.
Stern, S.T, and T.M. Potter, "NCL Method GTA-2, Version 1.0: HEP G2 Hepatocarcinoma Cytotoxicity Assay," Nanotechnology Characterization Laboratory, Frederick, Md., Feb. 2006, pp. 1-9.
Sullivan, S.M., and L. Huang, "Preparation and Characterization of Heat-Sensitive Immunoliposomes," Biochimica et Biophysica Acta (BBA)—Biomembranes 812(1)116-126, Jan. 1985.
Sun, S., and H. Zeng, "Size-Controlled Synthesis of Magnetite Nanoparticles," Journal of the American Chemical Society 124(28):8204-8205, Jul. 2002.

(56) References Cited

OTHER PUBLICATIONS

Taboada, E, et al., "New Ultrasmall Iron—Oxide Nanoparticles With High Magnetisation as Potential $T_1$-MRI Contrast Agents for Molecular Imaging," submitted to Journal of Materials Chemistry, preprint arXiv:cond-mat/0611243v1, Nov. 2006.

Tartaj, P., "Nanomagnets for Biomedical Applications," in H.S. Nalwa (ed.), "Encyclopedia of Nanoscience and Nanotechnology," American Scientific Publishers, Valencia, Calif., 2004, vol. 6, pp. 823-842.

Teeguarden, J.G., et al., "Particokinetics In Vitro: Dosimetry Considerations for In Vitro Nanoparticle Toxicity assessments," Toxicological Sciences 95(2):300-312, Feb. 2007.

Tilly, W., et al., "Temperature Data and Specific Absorption Rates in Pelvic Tumours: Predictive Factors and Correlations," International Journal of Hyperthermia 17(2):172-188, Mar.-Apr. 2001.

Tucciarone, J., et al., "Layer Specific Tracing of Corticocortical and Thalamocortical Connectivity in the Rodent Using Manganese Enhanced MRI," NeuroImage 44(3):923-931, Feb. 2009.

Ulman, A., "Formation and Structure of Self-Assembled Monolayers," Chemical Reviews 96(4):1533-1554, Jun. 1996.

Unger, E., et al., "Gadolinium-DTPA Liposomes as a Potential MRI Contrast Agent: Work in Progress," Investigative Radiology 23(12):928-932, Dec. 1988.

Urano, M., et al., "For the Clinical Application of Thermochemotherapy Given at Mild Temperatures," International Journal of Hyperthermia 15(2):79-107, Mar.-Apr. 1999.

Valko, M., et al., "Metals, Toxicity and Oxidative Stress," Current Medicinal Chemistry 12(10)1161-1209, May 2005.

Van Der Zee, J., et al., "Comparison of Radiotherapy Alone With Radiotherapy Plus Hyperthermia in Locally advanced Pelvic Tumours: A Prospective, Randomised, Multicentre Trial," Lancet 355(9210):1119-1125, Apr. 2000.

Vaupel, P., et al., "Blood Flow, Oxygen and Nutrient Supply, and Microenvironment of Human Tumors: A Review," Cancer Research 49(23):6449-6465, Dec. 1989.

Vijayakumar, fR., et al., "Sonochemical Synthesis and Characterization of Pure Nanometer-Sized $Fd_3O_4$ Particles," Materials Science and Engineering A 286(1):101-105, Jun. 2000.

Nang, Y.-X.J., et al., "Superparamagnetic Iron Oxide Contrast Agents: Physicochemical Characteristics and Applications in MR Imaging," European Radiology 11(11):2319-2331, 2001.

Nang, Z.L., et al., "Polyhedral Shapes of Cobalt Nanocrystals and Their Effect on Ordered Nanocrystal Assembly," Advanced Materials 12(24):1944-1946, Dec. 2000.

Natson, J.H.P., "Magnetic Filtration," Journal of Applied Physics 44(9):4209-4213, Sep. 1973.

Weinmann, H.-J., et al., "Characteristics of Gadolinium-DTPA Complex: A Potential NMR Contrast Agent," American Journal of Roentgenology 142(3):619-624, Mar. 1984.

Weissleder, R., et al., "Long-Circulating Iron Oxides for MR Imaging," Advanced Drug Delivery Reviews 16(2-3):321-334, Sep. 1995.

Weissleder, R., et al., "Superparamagnetic Iron Oxide: Enhanced Detection of Focal Splenic Tumors With MR Imaging," Radiology 169(2):399-403, Nov. 1988.

Weissleder, R., et al., "Superparamagnetic Iron Oxide: Pharmacokinetics and Toxicity," American Journal of Roentgenology 152(1):167-173, Jan. 1989.

Weizenecker, J., et al., "Magnetic Particle Imaging Using a Field Free Line," Journal of Physics D: Applied Physics 41(10):105009, May 2008, 3 pages.

Weizenecker, J., et al., "A Simulation Study on the Resolution and Sensitivity of Magnetic Particle Imaging," Physics in Medicine and Biology 52(21):6363-6374, Nov. 2007.

Willard, M.A., et al., "Chemically Prepared Magnetic Nanoparticles," International Materials Reviews 49(3-4):125-170, Jun. 2004.

Wolf, G.L., and L. Baum, "Cardiovascular Toxicity and Tissue Proton T, Response to Manganese Injection in the Dog and Rabbit," American Journal of Roentgenology 141(1):193-197, Jul. 1983.

Woodcock, L.V., "Entropy Difference Between the Face-Centred Cubic and Hexagonal Close-Packed Crystal Structures," Nature 385(6612):141-143, Jan. 1997.

Nust, P., et al., "Hyperthermia in Combined Treatment of Cancer," Lancet Oncology 3(8):487-497, Aug. 2002.

Yanase, M., et al., "Antitumor Immunity Induction by Intracellular Hyperthermia Using Magnetite Cationic Liposomes," Japanese Journal of Cancer Research 89(7):775-782, Jul. 1998.

Yanes, R., et al., "Effective Anisotropies and Energy Barriers of Magnetic Nanoparticles With Néel Surface Anisotropy," Physical Review B 76(6):064416-1-064416-13, Aug. 2007.

Yatvin, M.B., et al., "pH-Sensitive Liposomes: Possible Clinical Implications," Science 210(4475):1253-1255, Dec. 1980.

Yin, H., et al., "The Effects of Particle Size and Surface Coating on the Cytotoxicity of Nickel Ferrite," Biomaterials 26(29):5818-5826, Oct. 2005.

Yin, Y., and A.P. Alivisatos, "Colloidal Nanocrystal Synthesis and the Organic-Inorganic Interface," Nature 437(7059):664-670, Sep. 2005.

Yu, W.W., "Semiconductor Quantum Dots: Synthesis and Water-Solubilization for Biomedical Applications," Expert Opinion on Biological Therapy 8(10):1571-1581, Oct. 2008.

Yu, W.W., et al., "Aqueous Dispersion of Monodisperse Magnetic Iron Oxide Nanocrystals Through Phase Transfer," Nanotechnology 17(17):4483-4487, Sep. 2006.

Yu, W.W., et al., "Forming Biocompatible and Nonaggregated Nanocrystals in Water Using Amphiphilic Polymers," Journal of the American Chemical Society 129(10):2871-2879, Mar. 2007.

Yu, W.W., et al., "Synthesis of Monodisperse Iron Oxide Nanocrystals by Thermal Decomposition of Iron Carboxylate Salts," Chemical Communications 20:2306-2307, Oct. 2004.

Ferguson, R.M., et al., "Optimization of Nanoparticle Core Size for Magnetic Particle Imaging," Journal of Vlagnetism and Magnetic Materials 321(10):1548-1551, May 2009. (Author Manuscript provided, PMCID: PMC2709850, available in PMC Jul. 14, 2009, 11 pages).

Notice of Reasons for Refusal mailed Apr. 5, 2016, issued in corresponding Japanese Application No. 2013-516656, filed Jun. 20, 2011, 4 pages.

Ferguson, R.M., et al., "Size-Dependent Relaxation Properties of Monodisperse Magnetite Nanoparticles Measured Over Seven Decades of Frequency by AC Susceptometry," IEEE Transactions on Magnetics 49(7):3441-3444, Jul. 2013.

Ferguson, R.M., et al., "Tailoring the Magnetic and Pharmacokinetic Properties of Iron Oxide Magnetic Particle Imaging Tracers," Biomedizinische Technik (Biomedical Engineering) 58(6):493-507, Dec. 2013.

Ferguson, R.M., et al., "Tracer Design for Magnetic Particle Imaging (Invited)," Journal of Applied Physics 111(7):07B318-1-07B318-5, Apr. 2012.

Goodwill, P.W., et al., "X-Space MPI: Magnetic Nanoparticles for Safe Medical Imaging," Advanced Materials 24(28):3870-3877, Jul. 2012.

Khandhar, A.P, et al., "Monodisperse Magnetite Nanoparticle Tracers for in Vivo Magnetic Particle Imaging," Biomaterials 34(15):3837-3845, May 2013.

Khandhar, A.P., et al., "Monodispersed Magnetite Nanoparticles Optimized for Magnetic Fluid Hyperthermia: Implications in Biological Systems," Journal of Applied Physics 109(7):07B310-1-07B310-3, Apr. 2011.

Khandhar, A.P., et al., "Tailored Magnetic Nanoparticles for Optimizing Magnetic Fluid Hyperthermia," Journal of Biomedical Materials Research 100A(3):728-737, Mar. 2012.

\* cited by examiner

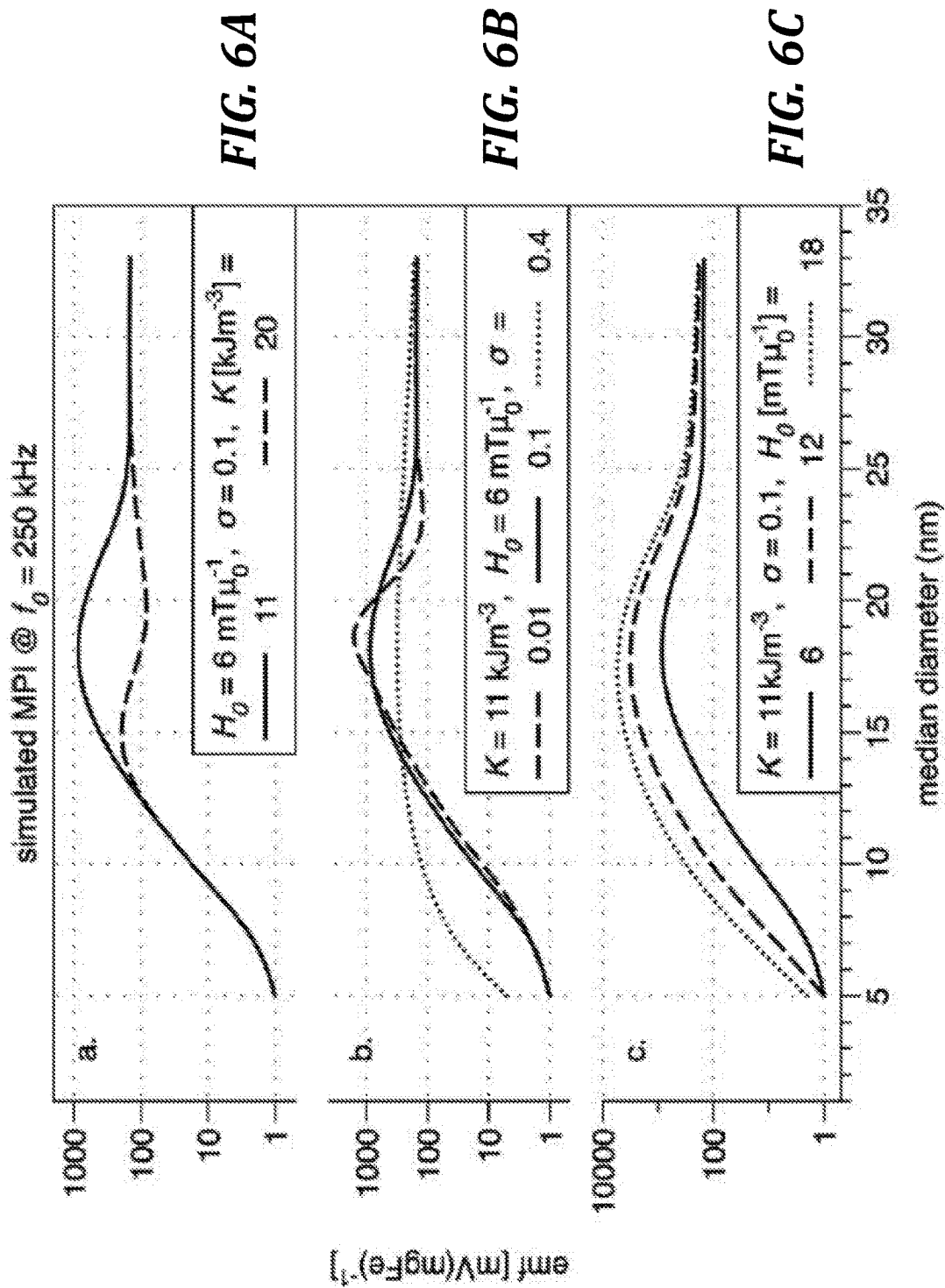

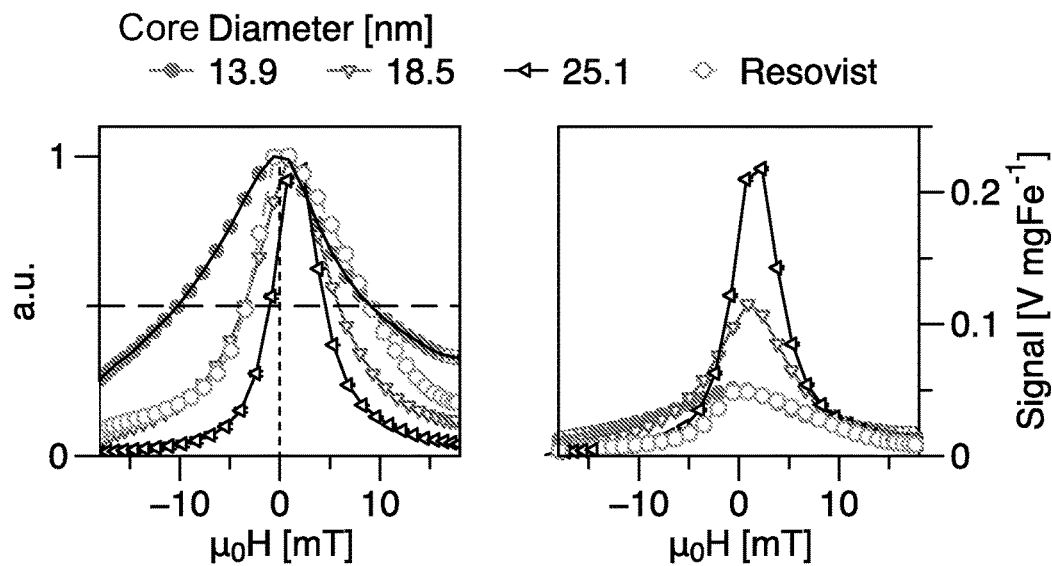
FIG. 20A  FIG. 20B
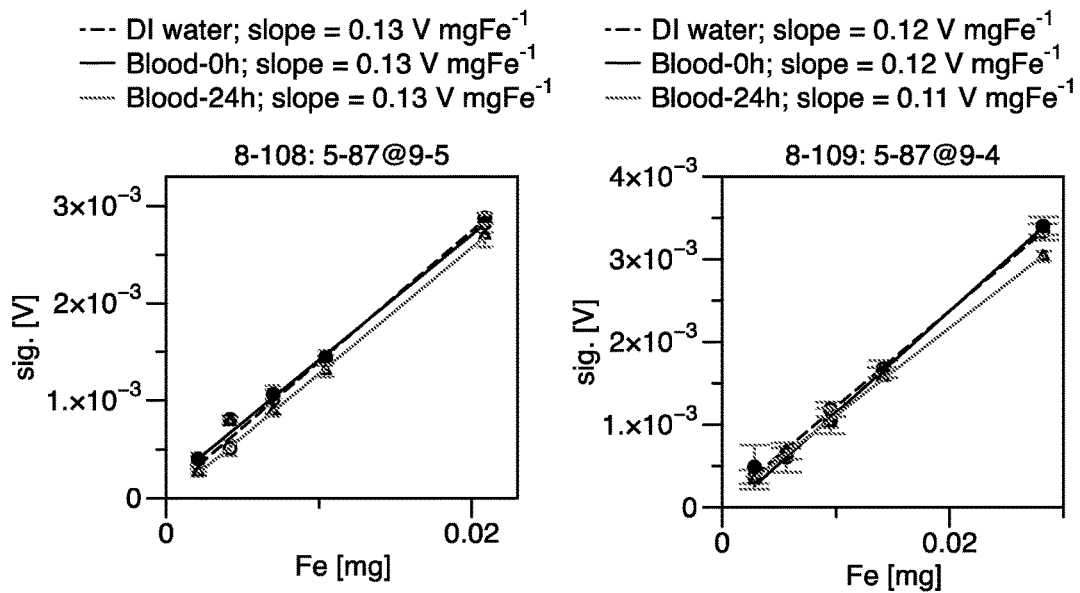
FIG. 21A  FIG. 21B

COATED MAGNETIC NANOPARTICLES

CROSS-REFERENCES TO RELATED APPLICATIONS

This application is a continuation-in-part of U.S. application Ser. No. 13/805,763, filed Feb. 26, 2013, which is the National Stage of International Application No. PCT/US2011/041090, which claims the benefit of U.S. Provisional Application No. 61/356,892, filed Jun. 21, 2010, and U.S. Provisional Patent Application No. 61/441,933, filed Feb. 11, 2011, the entire disclosures of which are hereby incorporated by reference herein. This application is also a continuation-in-part of International Application No. PCT/US2014/067410, filed Nov. 25, 2014, which claims the benefit of U.S. Provisional Application No. 61/908,563, filed Nov. 25, 2013, the entire disclosures of which are hereby incorporated by reference herein.

STATEMENT OF GOVERNMENT LICENSE RIGHTS

This invention was made with Government support under NIH 1R01EB013689-01/NIBIB and NIH 1R42EB013520-02/NIBIB, awarded by the National Institutes of Health. The Government has certain rights in the invention.

BACKGROUND

The present disclosure relates to magnetic nanoparticles and related devices and methods. More specifically, the present disclosure relates to compositions and methods of making magnetic nanoparticles having a narrow size distribution for use in diagnostics and therapeutics.

Magnetic nanoparticles (also referred to as MNPs) are attractive agents for biomedicine due to strong intrinsic magnetism that, through interaction with a magnetic field, enables their detection or influence from deep within a living subject. Rightly, magnetic nanoparticles have been studied extensively as potential contrast agents or nanoparticle materials in molecular imaging applications based on magnetic resonance imaging (MRI), as well as carriers for magnetically assisted drug delivery and hyperthermia. Recently, a new imaging modality called magnetic particle imaging (MPI) was introduced as a technique for visualizing magnetic nanoparticles in humans and animals. MPI is fast, quantitative, sensitive, and features good spatial resolution, a combination that is difficult to realize in MR imaging of magnetic nanoparticles, because MPI directly probes the large magnetic nanoparticle moment rather than its indirect effect on proton relaxation, as does MR imaging. Noteworthy recent MPI studies include in vivo, real-time imaging of magnetic nanoparticles passing through a beating mouse heart and compact, single-sided scanners that can image a patient without first inserting them into a costly and potentially claustrophobic magnetic device.

Despite much exciting progress in MPI scanner design and related image processing, relatively little effort has been spent developing magnetic nanoparticles that optimize imaging sensitivity. In fact, for MPI to successfully move beyond proof-of-principle experiments into the clinic or preclinical research laboratory, it will be important to engineer magnetic nanoparticles that are optimized for MPI. Most recent studies have used commercially available magnetic nanoparticle agents, including Resovist® (Bayer Schering Pharma, Berlin) and Feridex I.V.® (AMAG Pharmaceuticals, Lexington, Mass.; trade name Endorem™ in Europe); these are far from being magnetically optimized for MPI and thus inhibit MPI from reaching its full potential in terms of both spatial resolution and mass sensitivity. For example, in Resovist®, which to date has been the most popular material for MPI studies, it has been shown that only 3% of the total sample mass contributes noticeably to the MPI signal. More efficient nanoparticles are desired for molecular imaging applications that depend on active targeting, where for the highest sensitivity, each unit of nanoparticle is desired to generate the maximum achievable MPI signal voltage. Furthermore, for quantitative imaging, the signal intensity, and therefore magnetic nanoparticle properties, are desired to be uniform and reproducible.

In addition, magnetic nanoparticles are an attractive option for site-specific cancer therapies because they can be remotely targeted by the application of external magnetic field gradients or other active and passive targeting methods. Once localized, Magnetic Fluid Hyperthermia (MFH), a therapeutic modality that utilizes alternating magnetic fields (AMF) to dissipate heat from the resulting relaxation losses in magnetic nanoparticles, can be used to induce localized heating. Heating cancer cells (typically to ~42-43° C.) is known to disrupt cellular metabolism making adjuvant therapy by conventional established methods more efficient. A wide range of ferromagnetic nanoparticles can be synthesized for MFH. Due to their modest magnetic characteristics, however, magnetic nanoparticles need to be optimized in terms of their morphological (size, size distribution, shape), crystallographic (phase purity) and magnetic (relaxation) characteristics for effective application in MFH.

Superparamagnetic iron oxide nanoparticles (SPIONs) composed of magnetite ($Fe_3O_4$), maghemite ($Fe_2O_3$) or a mixture of magnetite and maghemite, have been used in the clinic to enhance the T2/T2*(negative) MRI contrast [Feridex I.V.® and Combidex®—produced by AMAG pharmaceuticals, Resovist®, produced by Bayer Schering Corporation], and more recently for the treatment of iron deficiency anemia in chronic kidney disease (CKD) patients [Feraheme®—produced by AMAG pharmaceuticals]. Experimentally, SPIONs of various compositions have been used for biomedical applications such as cell labeling and separation, drug delivery, magnetic gene transfection (magnetofection), tissue repair and hyperthermia [Gupta et al, Biomaterials 2005; 26:3995-4021, Krishnan, IEEE Trans. Mag. 46, 2523-2558 (2010)].

The unique nonlinear magnetic response of SPIONs can be exploited in alternating magnetic fields to induce a detectable signal that is proportional to the ac-susceptibility (m'(H)). Applications such as MPI [Gleich and Weizenecker, Nature 2005; 435:1214-7], magnetic sentinel lymph node biopsy (SLNB) [M. Douek et al, Ann. Surg. Oncol., 21, 1237 (2013)] and MFH [R. K. Gilchrist et al, Ann. Surgery 146, 596 (1957); U. Gneveckow et al, Med. Phys. 31, 1444 (2004)], employ alternating magnetic fields in the radiofrequency range (1 1,000 kHz) applied to SPIONs. Maximum signal, especially in MPI, is generated when SPIONs with core sizes near the superparamagnetic-to-ferrimagnetic transition and uniform size distribution are used.

With clinical end-use in perspective, the first generation of SPIONs designed for either in vivo MPI or MFH therapy must be biocompatible and demonstrate appropriate circulation times to enable vascular imaging or site-specific heating, respectively. For performing first-pass and subsequent blood pool imaging, a circulation time of approximately 1 hour should provide clinicians sufficient time; for instance, Ablavar® (Lantheus Medical Imaging)—a gadolinium-based MRI blood pool agent remains in circulation for up to 1 hour [www.ablavar.com]. However, given the real-time imaging capability of MPI, even shorter circulation times may be sufficient. Ultimately, practical considerations such as the preferred administration route (intravenous injection or cardiac catheterization; the latter is preferred if in situ interventional procedures are deemed necessary) and the actual time it takes to ready patients for MPI scans will determine the optimum circulation time of SPIONs. On the other hand, studies indicate that cancer targeting—measured by targeting efficiency and not imaging speed—requires several hours (>1 hour) of circulation time [Fang et al, Eur J Pharm Sci 2006; 27:27-36, Cole et al, Biomaterials 2011; 32:2183-93]; typically, longer the circulation time, greater the probability of reaching the disease site [Albanese et al, Annu Rev Biomed Eng 2012; 14:1-16]. Thus, it would be advantageous to have a surface coating platform that can be readily modified to tune the blood half-life and/or other characteristics of SPIONs for desired applications. It is also important that the biodistribution and clearance is via well-defined pathways; for example, for patients with Chronic Kidney disease it is important that in vivo tracers administered for MPI are clear not by the Kidney but by the liver and spleen.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, a plurality of nanoparticles is provided. The nanoparticles are referred to herein as nanoparticles (NP), magnetic nanoparticles (MNP), and superparamagnetic iron oxide nanoparticles (SPIONs).

In one embodiment, each nanoparticle includes:

a core comprising iron oxide, wherein the core has a diameter of 15 nm to 30 nm; and a coating surrounding the core, the coating comprising a PMAR-PEG copolymer having a poly(maleic anhydride alt-$H_2C=CH-R1$) (PMAR) portion and a plurality of polyethylene glycol (PEG) portions each with a molecular weight (Mn) of 10,000 Da or greater;

wherein R1 is a hydrophobic moiety.

In another aspect, methods of using the nanoparticles are provided. In one embodiment, the method comprises applying a magnetic field to a plurality of nanoparticles according to the disclosed embodiments. In certain applications, the magnetic field is applied to a subject into which the nanoparticles have been dispersed.

The central receive coil is wound with opposite sense from the two adjacent coils to inductively decouple the transmit and receive channels.

Figures 5A, 5B:
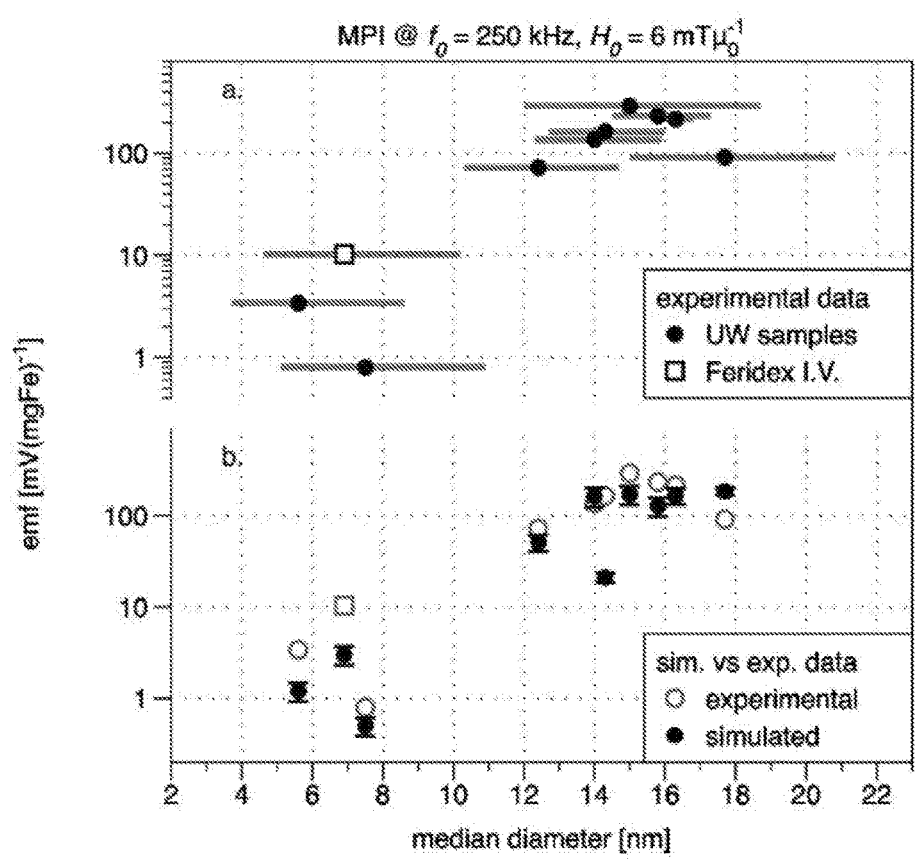

FIG. 5A shows MPI signal testing results, in accordance with an embodiment of the present disclosure. Symbols represent MNP samples, and the error bars delineate the first standard deviation of the sample diameter distribution. FIG. 5B shows simulated data for each experimental sample (in black) with measured points duplicated (in gray) for reference.

FIGS. 6A-6C show simulated MPI data for (A) different anisotropy constants K, (B) different diameter distribution widths ($\sigma$), and (C) different driving field amplitudes $H_0$, in accordance with an embodiment of the present disclosure.

Figures 7A, 7B, 7C:
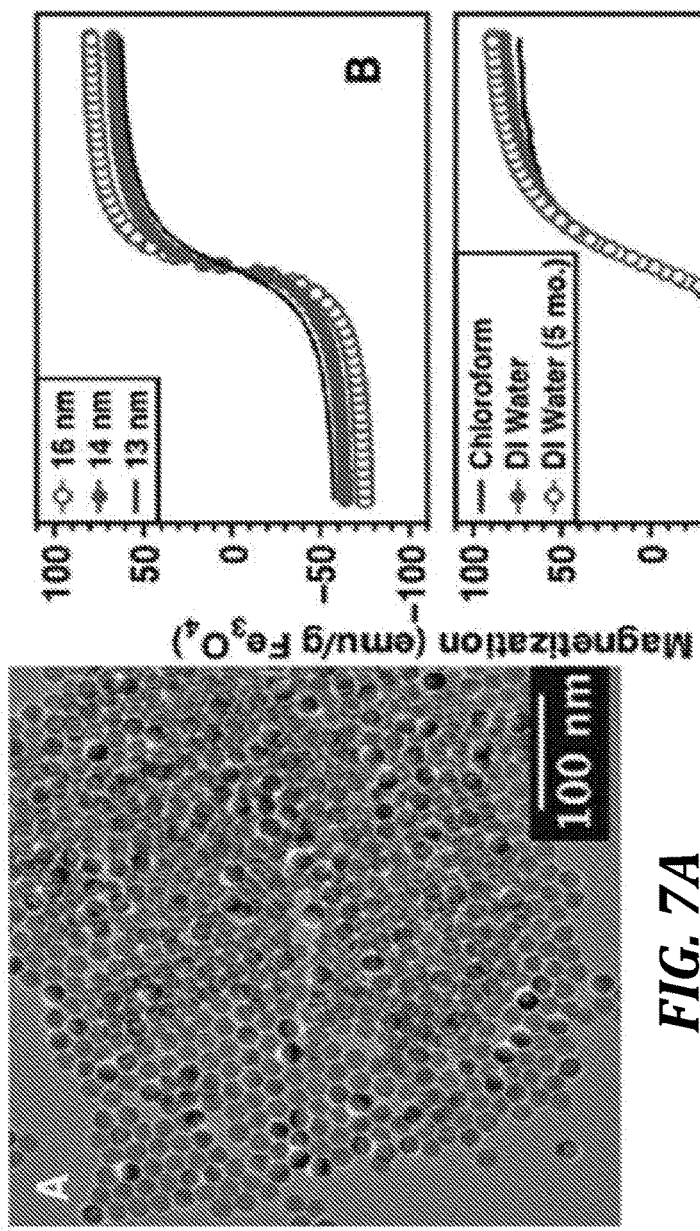

FIGS. 7A-7C shows (A) TEM image of ~16 nm diameter magnetite nanoparticles; (B) magnetization curves for a range of particle diameters; and (C) magnetization curves before and after phase transfer for 12 nm MNPs and 5 months after phase transfer, in accordance with an embodiment of the present disclosure.

Figure 8A:
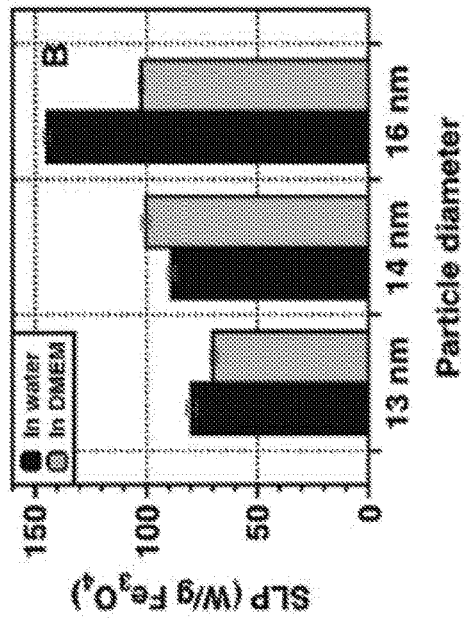
Figure 8B:
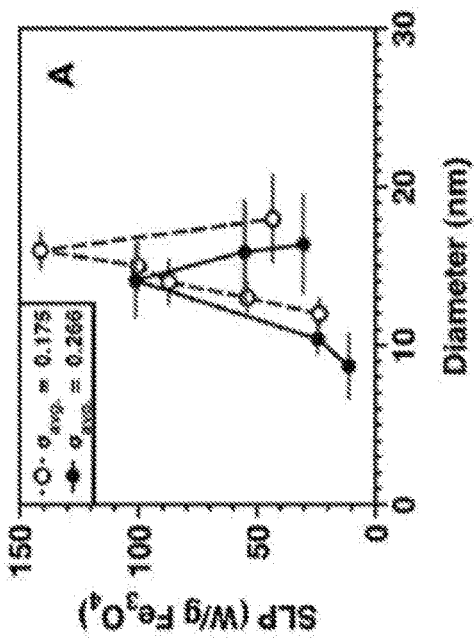
Figure 8C:
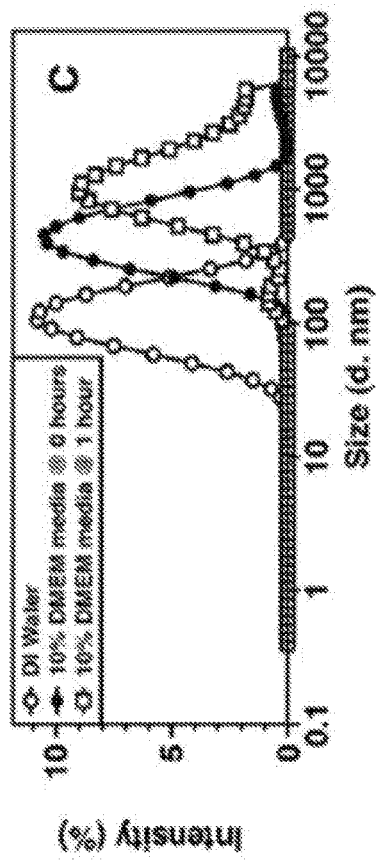

FIGS. 8A-8C show (A) SLP of a range of MNP diameters; (B) heating capacity of MNPs coated with PMAO-PEG as measured in water and DMEM; (C) and DLS measurements of MNPs coated with PMAO-PEG, in accordance with an embodiment of the present disclosure.

Figure 9:
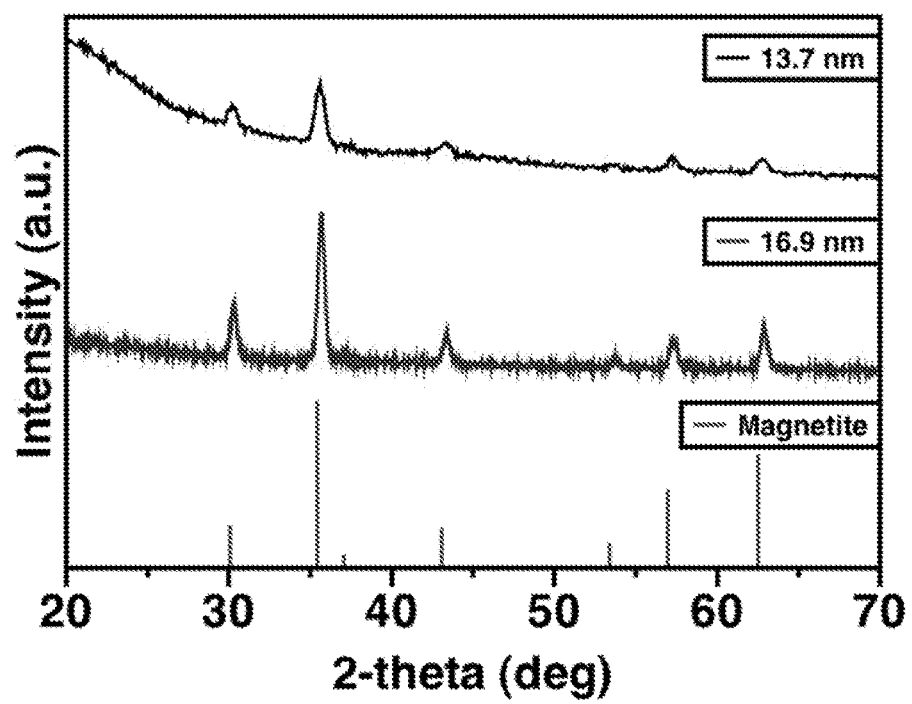

FIG. 9 shows powder X-ray diffraction, $\theta$-$2\theta$ scans, of magnetite nanoparticles, in accordance with an embodiment of the present disclosure. Sizes indicated in legends were determined by Scherrer's formula using the peak at $2\theta=35.4°$. The magnetite reference (bottom) was obtained from the International Centre for Diffraction Data (PDF#019-0629).

Figure 10A:
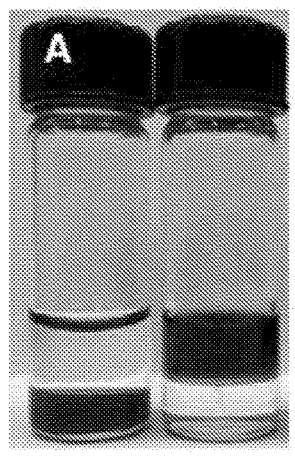
Figure 10B:
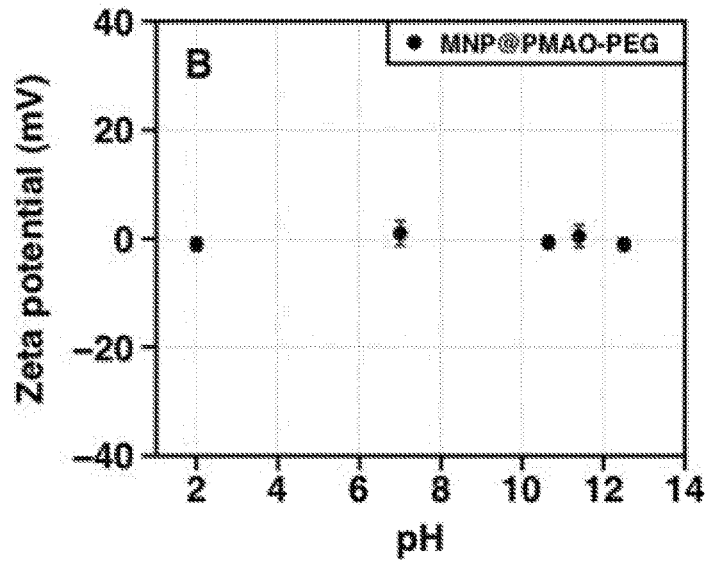
Figure 10C:
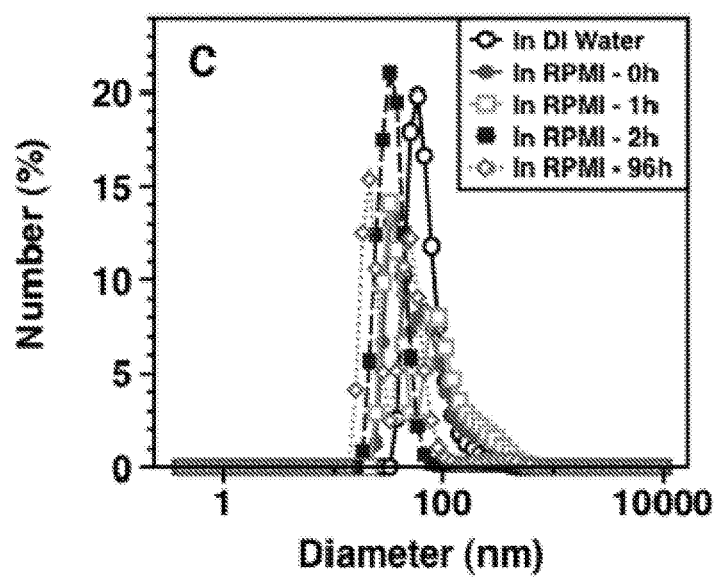

FIGS. 10A-10C show (A) MNPs preferentially dispersed in the denser chloroform phase before phase transfer (left), while preferring the aqueous phase after phase transfer (right); (B) Zeta potential of MNP@PMAO-PEG as a function of pH; and (C) Hydrodynamic size measurements of MNP@PMAO-PEG in RPMI 1640+10% FBS cell culture medium as a function of time, in accordance with an embodiment of the present disclosure.

Figure 11:
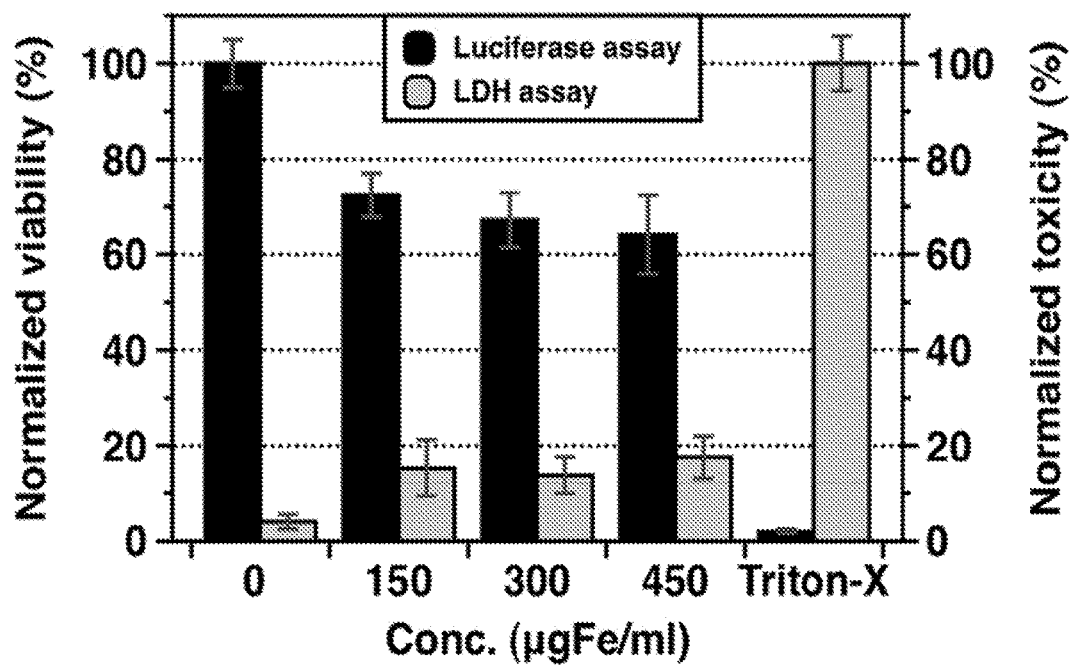
Figure 12:
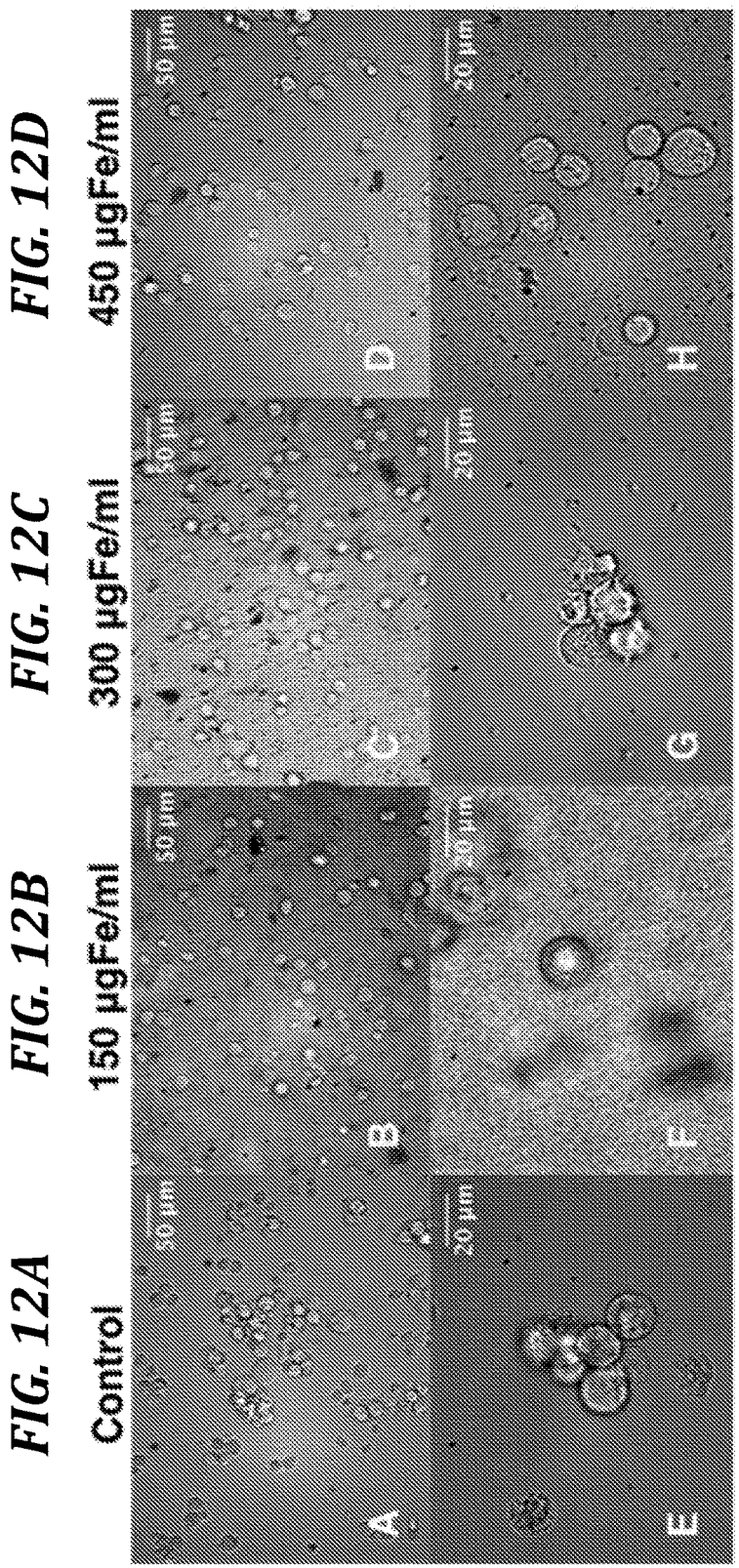

FIG. 11 provides in vitro cytotoxicity of MNP@PMAO-PEG in Jurkats. Viability measured via Luciferase assay and toxicity measured via LDH assay. MNPs were incubated for 24 hours in physiological conditions (37° C. and 5% $CO_2$), in accordance with an embodiment of the present disclosure.

FIGS. 12A-12H show bright field images of Jurkat cells after 24 hours incubation with MNP@PMAO-PEG, in accordance with an embodiment of the present disclosure.

Figure 13:
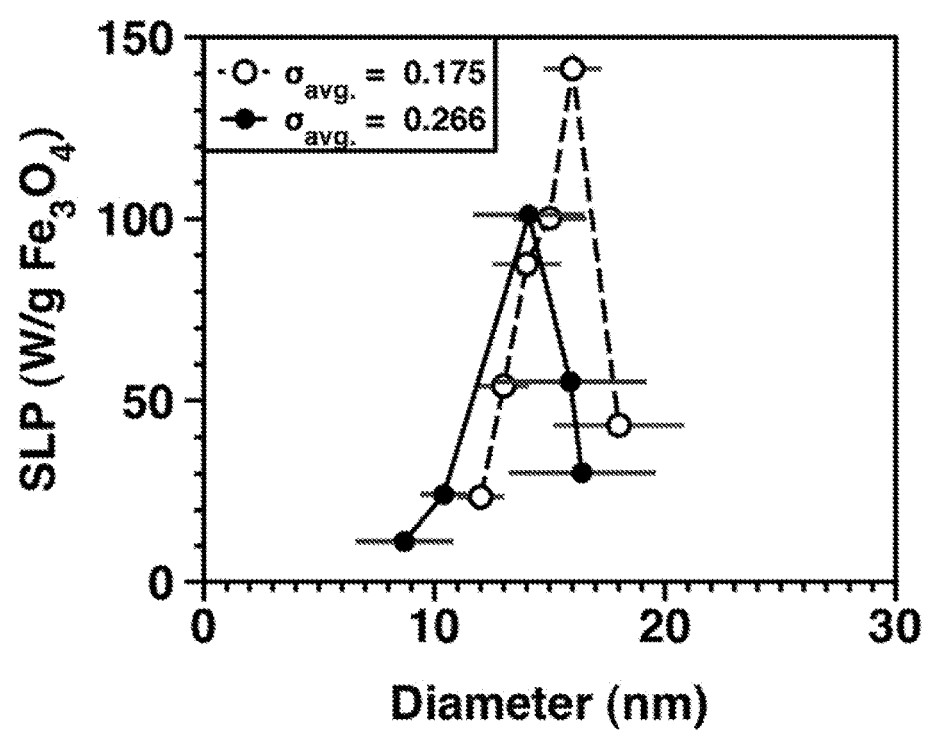

FIG. 13 shows specific loss power (W/g $Fe_3O_4$) as a function of size and size distribution (Frequency (f)=373 kHz and $H_O$ 14 kA/m), in accordance with an embodiment of the present disclosure.

Figures 14A, 14B, 14C:
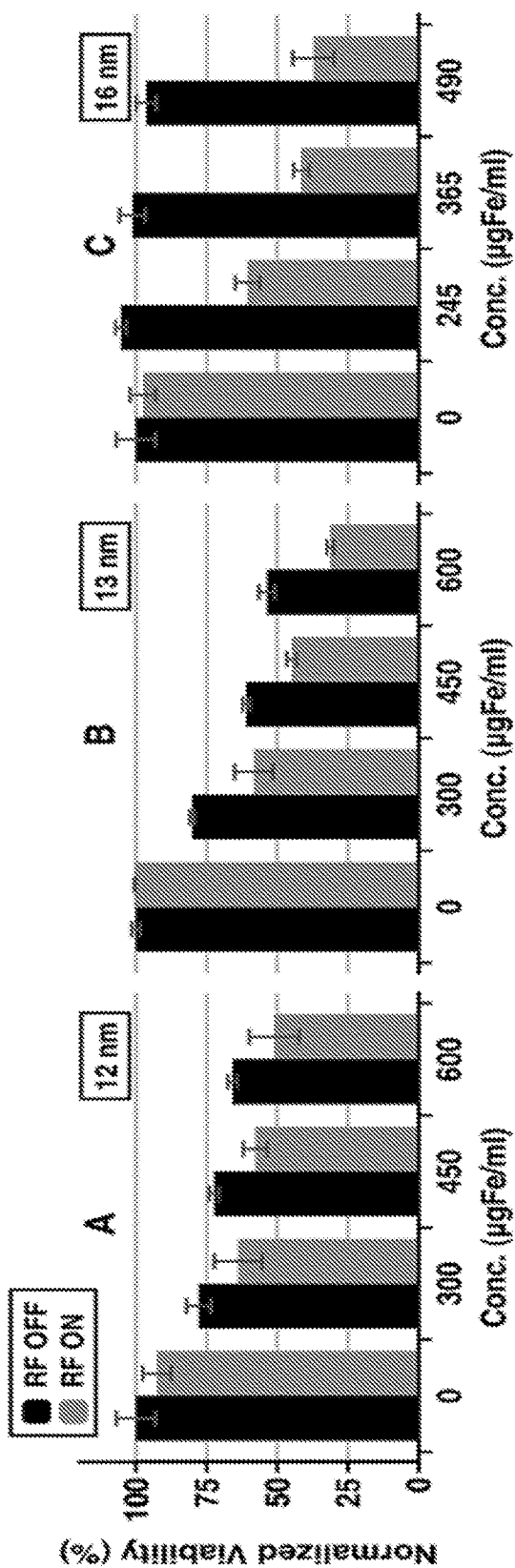

FIGS. 14A-14C shows in vitro heating of Jurkats using MNPs of diameters (A) 12 nm, (B) 13 nm and (C) 16 nm (AMF was applied for 15 minutes), in accordance with an embodiment of the present disclosure.

Figure 15:
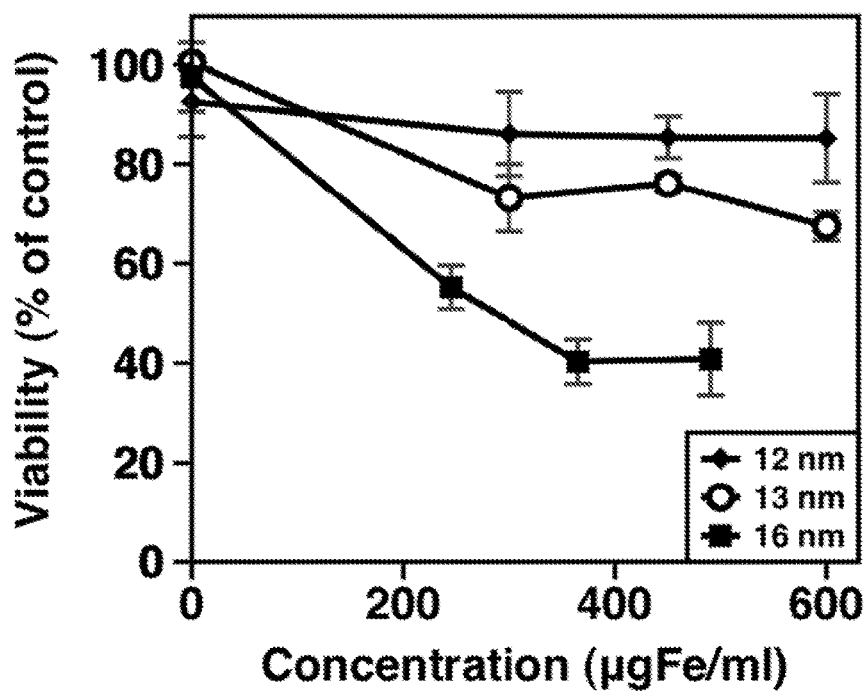

FIG. 15 shows cell viability relative to control calculated as AC $OFF_{avg}$–AC $ON_{avg}$, in accordance with an embodiment of the present disclosure.

Figure 16:
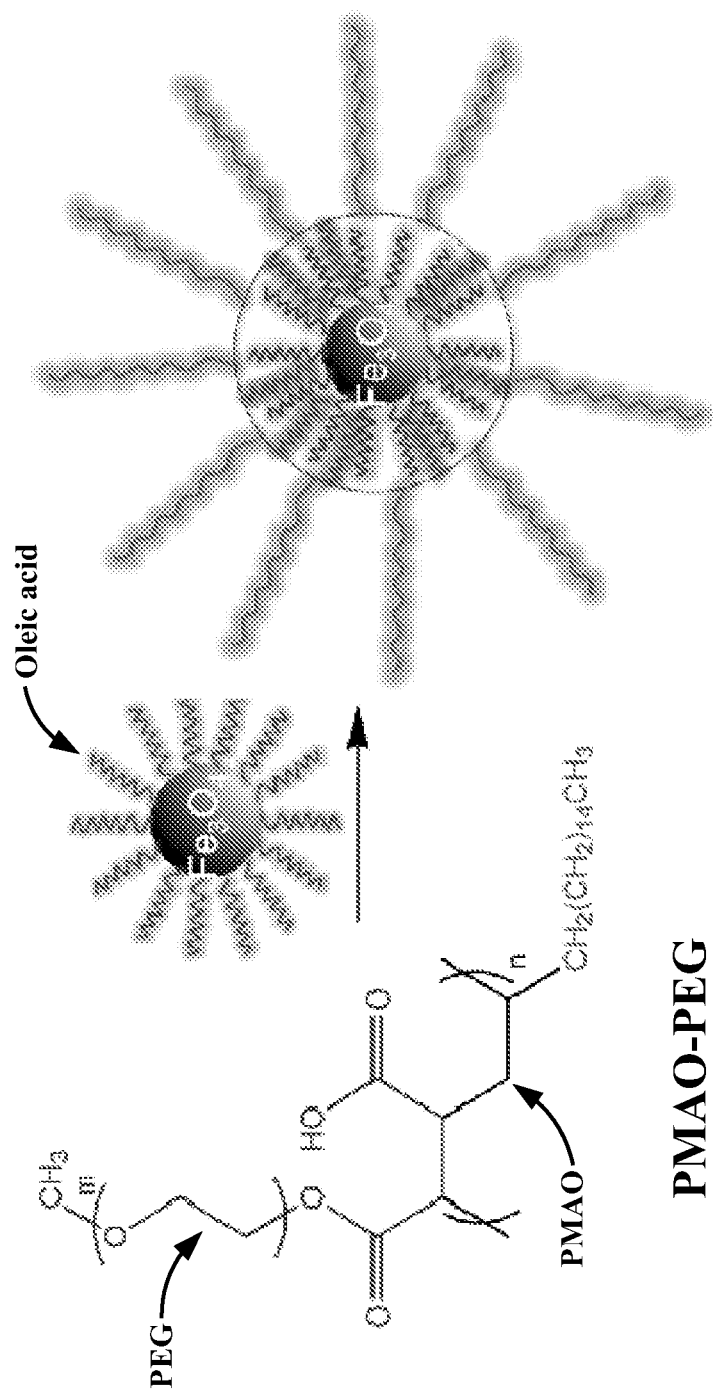

FIG. 16 schematically illustrates a representative magnetic nanoparticle in accordance with the disclosed embodiments.

Figure 17A:
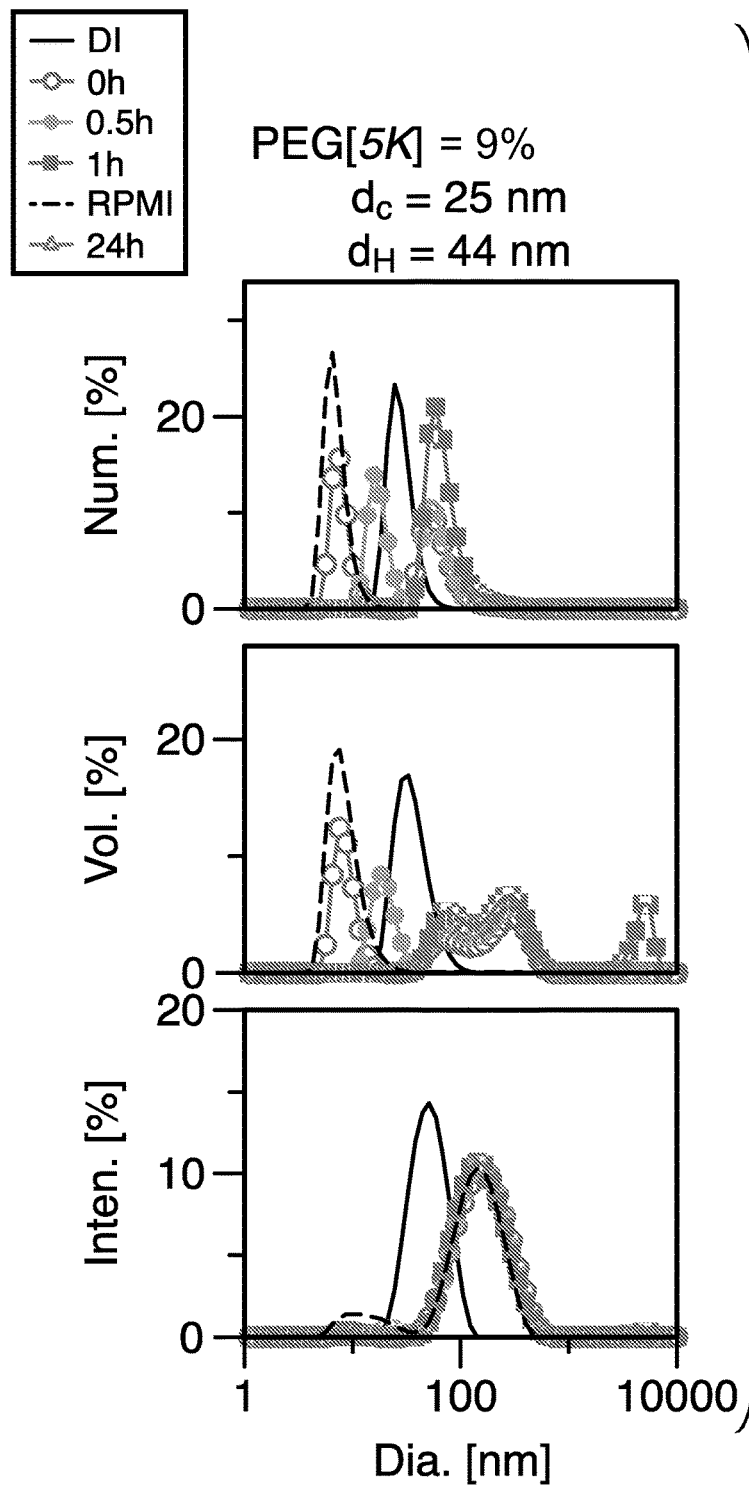
Figure 17B:
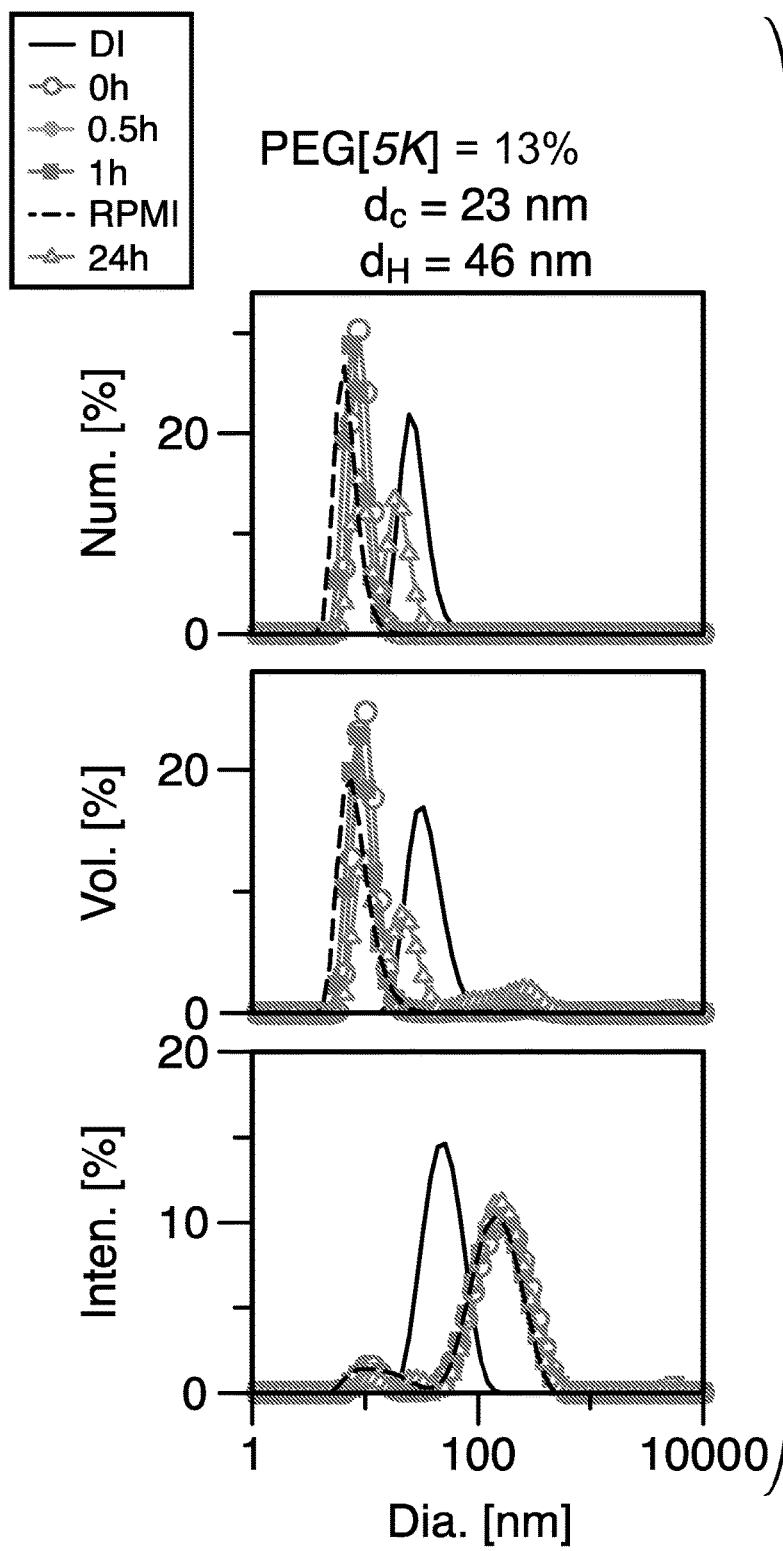
Figure 17C:
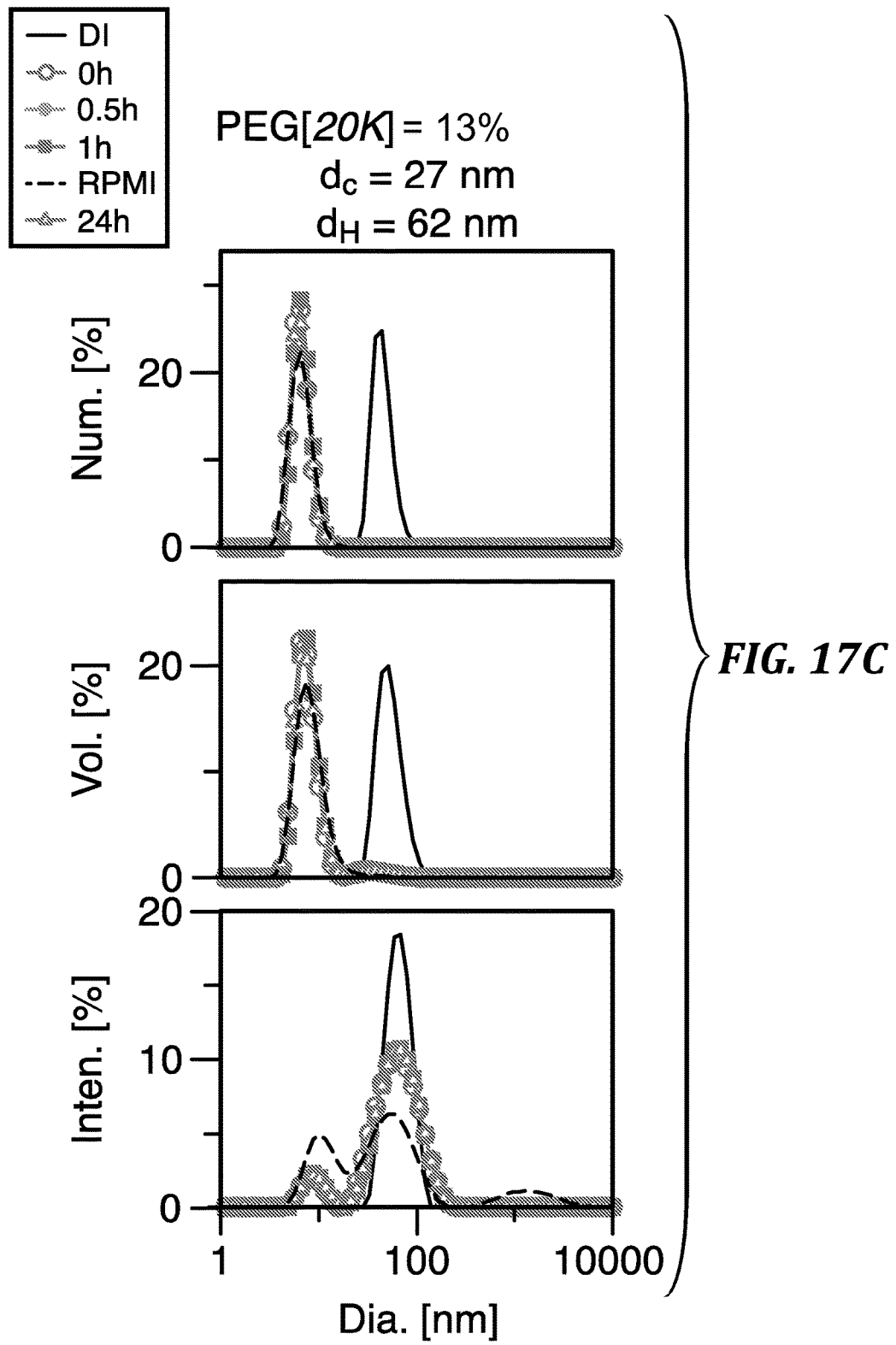

FIGS. 17A-17C graphically illustrate hydrodynamic size data from three samples of PMAO-PEG nanoparticles (>20 nm) in RPMI+10% FBS cell culture medium: FIGS. 17A and 17B are comparative samples with 5 k Da PEG at a loading of 9% and 13%, respectively; FIG. 17C is an exemplary embodiment having 20 k Da PEG at a loading of 13%.

Figures 18A, 18B, 18C:
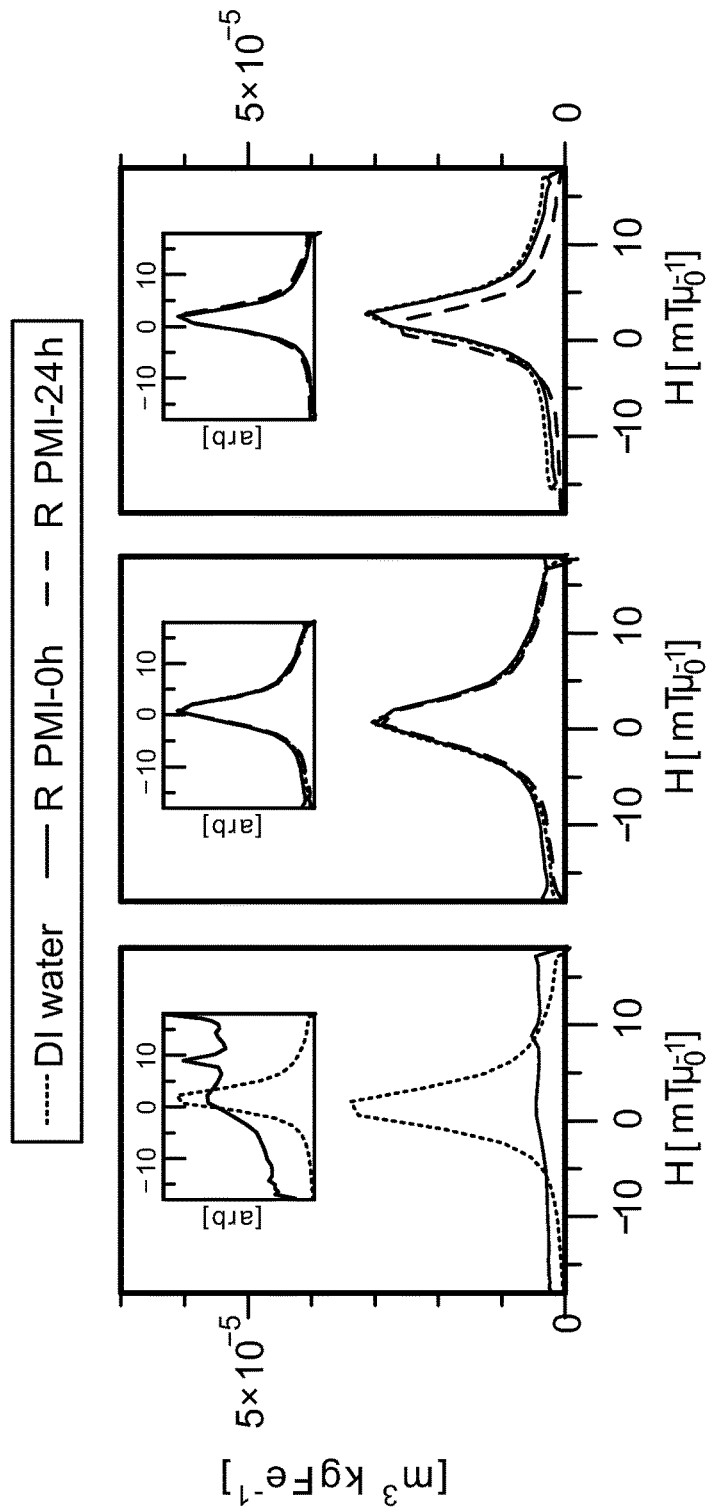

FIGS. 18A-18C graphically illustrate magnetic particle spectrometry data from three samples of PMAO-PEG nanoparticles in DI water and serum-rich cell culture medium: FIG. 18A is a comparative sample of 25 nm core diameter coated with 5 k Da PEG at a loading of 9%; FIG. 18B is a comparative sample of 23 nm core diameter coated with 5 k Da PEG at a loading of 13%; and FIG. 18C is an exemplary embodiment of 25 nm core diameter coated with 20 k Da PEG at a loading of 13%.

Figure 19A:
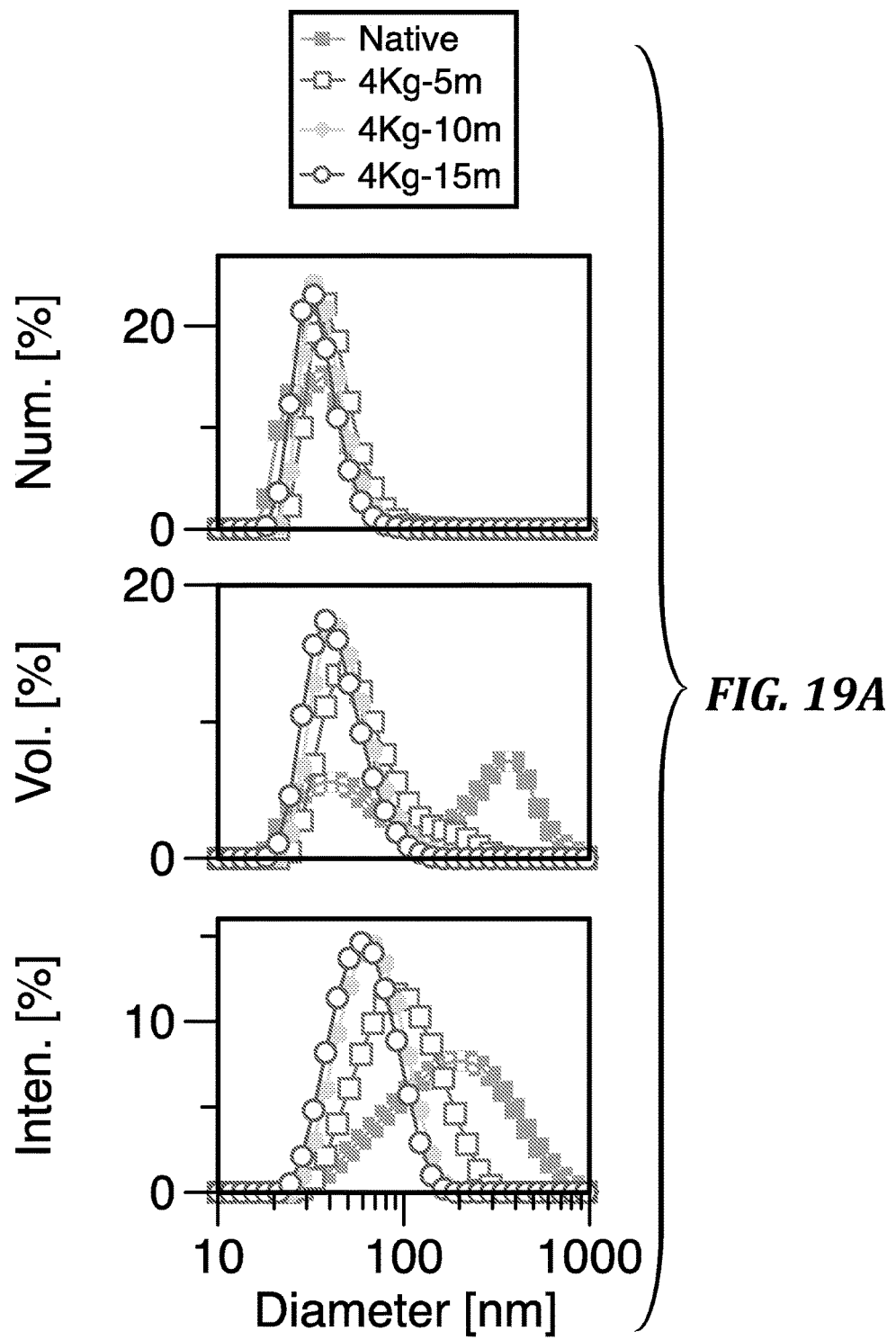

FIG. 19A graphically illustrates the effect of centrifugation on the hydrodynamic diameter of PMAO-PEG nanoparticles.

Figure 19B:
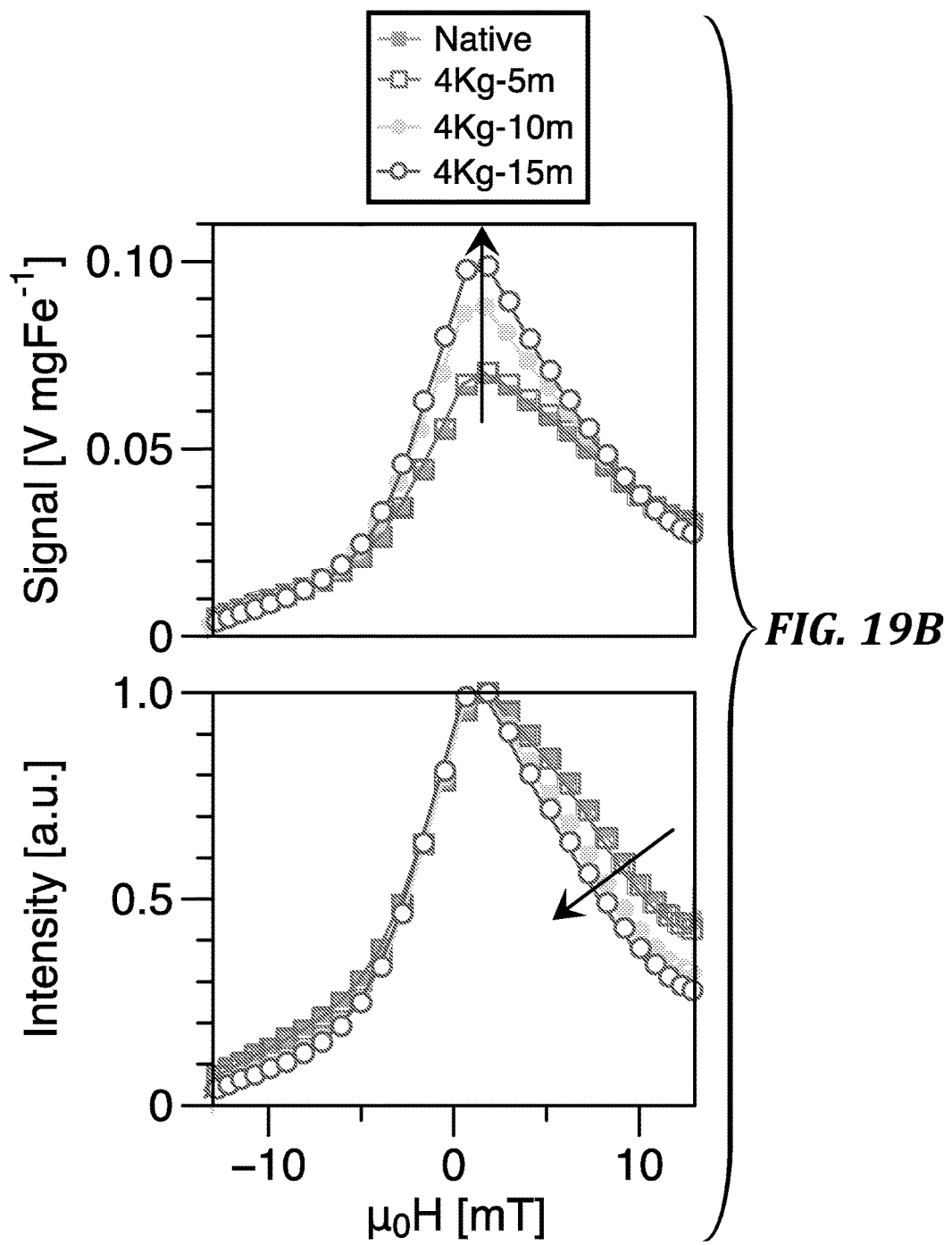

FIG. 19B graphically illustrates the mass (top) and intensity (bottom) of the PMAO-PEG nanoparticles evaluated in FIG. 19A by magnetic particle spectrometry.

FIGS. 20A and 20B graphically illustrate the magnetic particle spectrometry response to magnetic nanoparticle core diameter based on intensity (FIG. 20A) and mass (FIG. 20B).

FIGS. 21A and 21B graphically illustrate the magnetic response linearity of magnetic nanoparticles according to the disclosed embodiments in blood.

Figure 22:
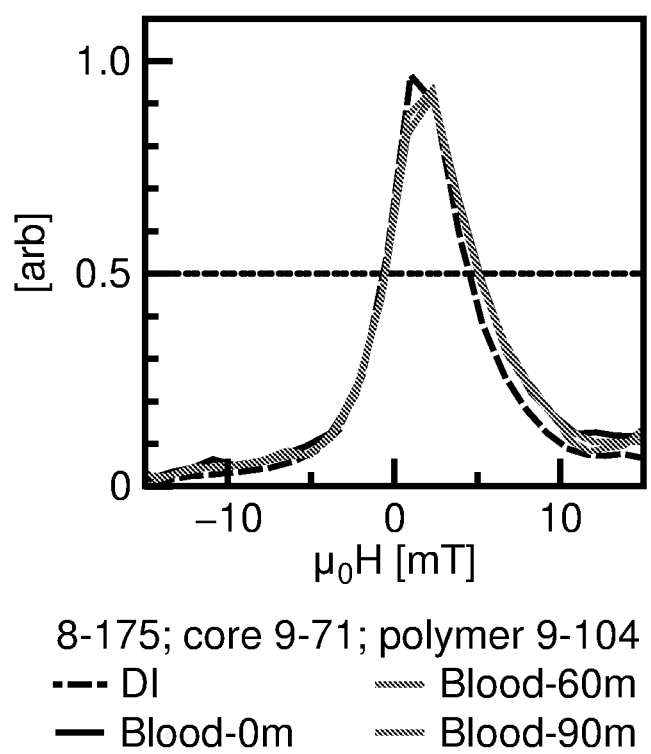

FIG. 22 graphically illustrates magnetic signal stability in blood of exemplary nanoparticles in vivo (mice).

DETAILED DESCRIPTION

The present disclosure relates to magnetic nanoparticles and related devices and methods. More specifically, the present disclosure relates to compositions and methods of making magnetic nanoparticles having a narrow size distribution for use in diagnostics and therapeutics.

I. Magnetic Nanoparticles Having a Narrow Size Distribution

The present disclosure provides a wide variety of magnetic nanoparticles that can be designed for several different types of applications, such as diagnostic and/or therapeutic purposes. For example, the magnetic nanoparticles of the present disclosure can include magnetic particles composed of a magnetic material, such as iron in oxidized form. In some embodiments, the magnetic nanoparticles can be composed of iron oxide. Magnetic nanoparticles can include, for example, magnetite ($Fe_3O_4$) and/or maghemite ($Fe_2O_3$) particles. In certain embodiments, the magnetic nanoparticles have a magnetite core that is a single, defect-free crystal of magnetite. The nanoparticles can have a variety of phases such as, e.g., a spinel phase. As described further herein, the magnetic nanoparticles can also include a magnetic core (e.g., a magnetite core) coated with amphiphilic molecules.

In one aspect, the present disclosure is based at least partially on fabrication of a population of magnetic nanoparticles having a size distribution that is surprisingly narrower than other previously reported magnetic particles. A population of magnetic nanoparticles having a narrow size distribution can provide a wide variety of advantages over existing magnetic particles. For example, magnetic properties can be highly dependent on the particle size, and in some cases, very small variations in size can exponentially improve or degrade the desired magnetic property. Producing magnetic nanoparticles with a narrow size distribution can influence magnetic imaging modalities (such as MPI or MRI) by selection and manufacture of a size that produces maximum signal and/or maximum resolution for improving imaging. Alternatively, localized tissue heating can be optimized by exciting narrowly sized magnetic nanoparticles that are located near, e.g., a cancer cell thereby improving options in magnetic hypothermia applications. These are just some of the improved capabilities provided by a narrow size distribution of magnetic nanoparticles. One of ordinary skill in the art will appreciate additional advantages in view of the present disclosure.

Thus, in one embodiment, the present disclosure provides a population of magnetic nanoparticles having a narrow size distribution. As provided herein, a "narrow size distribution" is intended to mean a distribution of magnetic nanoparticles that have sizes (e.g., diameters) that are within a certain specified range from a median diameter of the population of magnetic nanoparticles. The size distribution of magnetic nanoparticles can be determined by a variety of methods, and characterization of the distribution can depend on the method used to determine the sizes of the magnetic nanoparticles. Methods for analyzing sizes (e.g., diameters) of the magnetic nanoparticles include but are not limited to magnetic measurement techniques, optical techniques (e.g., photon correlation spectroscopy or dynamic light scattering) and imaging techniques (e.g., transmission electron microscopy).

The size distribution of a population of magnetic nanoparticles can be expressed in a variety of forms. For example, the size distribution can obey a log normal distribution, a normal distribution, a bimodal distribution, and the like. Various known techniques can be used to fit the size distribution a population of magnetic nanoparticles. In addition, the quality of fitting can be determined by a standard goodness of fit test, for example a chi-square test, or Kolmogorov-Smirnov test.

In some embodiments, sizes (e.g., diameters) in a population of magnetic nanoparticles can be characterized by a log normal distribution. In certain embodiments, the diameter distribution g(d) of magnetic nanoparticles can be approximated by a log normal distribution, as shown in Equation (1):

$$g(d) = \frac{1}{\sigma d\sqrt{2\pi}} \exp\frac{-\ln(d/d_o)^2}{2\sigma^2} \quad (1)$$

where exp(σ) is the geometric standard deviation of the distribution and do is the median diameter. For log normal distributions, standard deviation is not additive, but is multiplicative. Sigma (σ) can be described as the standard deviation of log(d), where d is the diameter and log(d) is distributed normally (i.e., defined by a Gaussian distribution). To determine a range of diameters for a population of magnetic nanoparticles, standard deviation for the distribution can be considered. For example, if sigma is 0.3, exp(σ) is 1.35 (unitless), then it can be interpreted that 68.3% of diameters in the distribution lie between $d_0*\exp(\sigma)$ and $d_0 \exp(\sigma)$ (unitless). In some embodiments, the population of magnetic nanoparticles will have a size (e.g., diameter) distribution that obeys a volume weighted (e.g., log normal) distribution function (e.g., as measured by magnetic measurement techniques or dynamic light scattering). In certain embodiments, the population of magnetic nanoparticles will have a size (e.g., diameter) distribution that obeys a number weighted (e.g., log normal) distribution function (e.g., as measured by transmission electron microscopy). The quality of fitting the log normal distributions can be identified by a standard goodness of fit test, for example a chi-square test.

In certain embodiments, the populations of magnetic nanoparticles that are described by log normal distributions can be described as having a median diameter and a standard deviation (σ), or alternatively exp(σ), which is the geometric standard deviation of the distribution (or a multiplicative standard deviation). Median diameters and diameter distributions can be determined, for example, using the Chantrell method, described in R. Chantrell et al., IEEE Trans. Magn. Mag. 14:975-977 (1978). The median diameters of populations of magnetic nanoparticles of the present disclosure can range, for example, from about 10 nm to about 50 nm, from about 10 nanometers (nm) to about 30 nm, from about 10 nm to about 25 nm, from about 10 nm to about 20 nm, from about 15 nm to about 30 nm, from about 15 nm to about 25 nm, and from about 15 nm to about 20 nm. Multiplicative standard deviations (i.e., exp(σ)) for populations of magnetic nanoparticles of the present disclosure can be, for example, less than about 1.35, less than about 1.22, or less than about 1.11. Sigma (σ) for these ranges corresponds to less than about 0.3, less than about 0.2, or less than about 0.1, respectively. In certain embodiments, the standard deviation (e.g., sigma) will decrease as the median diameter of magnetic nanoparticles is reduced.

The size distribution of a population of magnetic nanoparticles can also be expressed by a distance value from a median diameter of the population. For example, a percentage of magnetic nanoparticles can be characterized within nanometers distance from the median diameter of the population. For example, the narrow size distribution of magnetic nanoparticles can include a distribution where greater than about 70% of the magnetic nanoparticles in a population have a diameter less than 10.5 nm from the median diameter (e.g., as measured by a volume weighted log normal distribution function). In some embodiments, the narrow size distribution of magnetic nanoparticles can include a distribution where greater than about 70% of the magnetic nanoparticles in a population have a diameter less than 8.8 nm from the median diameter, as measured by a volume weighted log normal distribution function. In some embodiments, greater than about 70%, about 80%, about 90%, about 95% or about 99% of the magnetic nanoparticles in a population can have a diameter less than about 9 nm, about 8 nm, about 7 nm, about 6 nm, about 5 nm, about 4 nm, about 3 nm, about 2 nm or about 1 nm from the median diameter, for example, as measured by a volume-weighted (e.g., log normal) distribution function. In some embodiments, the narrow size distribution of magnetic nanoparticles can include a distribution where greater than about 70% of the magnetic nanoparticles in a population have a diameter less than 3 nm from the median diameter, as measured by a number weighted (e.g., log normal) distribution function. In some embodiments, greater than about 70%, about 80%, about 90%, about 95% or about 99% of the magnetic nanoparticles in a population can have a diameter less than about 5 nm, about 4 nm, about 3 nm, about 2.5 nm, about 2 nm, about 1.5 nm, about 1 nm, or about 0.5 nm from the median diameter, as measured by a number weighted log normal distribution function.

In addition to the nanoparticle core size characterizations described above, the populations of magnetic nanoparticles can also be characterized by hydrodynamic properties. For example, the populations of magnetic nanoparticles can include a mean hydrodynamic diameter, which, e.g., can be dependent on solution conditions and/or coatings of amphiphilic molecules on the surface of the magnetic nanoparticles. In certain embodiments, a population of magnetic nanoparticles of the present disclosure can include a mean hydrodynamic diameter ranging from about 20 nm to about 110 nm, from about 30 nm to about 100 nm, from about 40 to about 90 nm, from about 50 to about 80 nm, or from about 60 nm to about 70 nm in aqueous solution.

II. Methods of Making Magnetic Nanoparticles

The present disclosure includes methods of making magnetic nanoparticles described herein. A variety of techniques can be used that, for example, can depend on the desired size and/or properties of the magnetic nanoparticles. For example, the methods of making magnetic nanoparticles can be tailored to produce magnetic nanoparticles with sizes and magnetic properties that are optimal for particular diagnostic and/or therapeutic applications.

Figure 1:
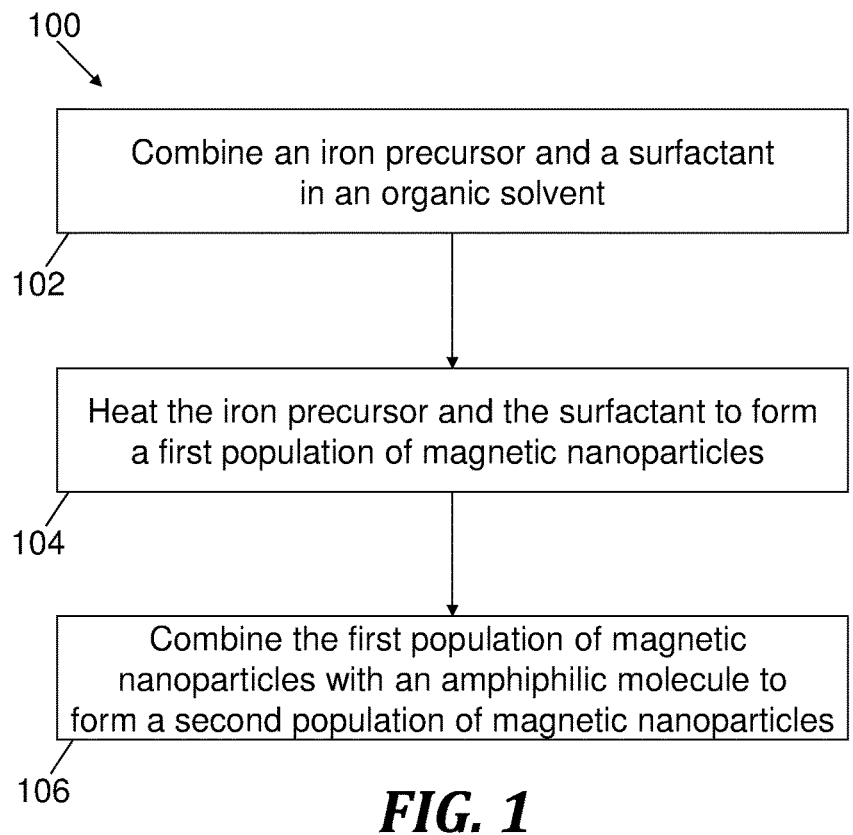
FIG. 1 shows a method of making magnetic nanoparticles, in accordance with an embodiment of the present disclosure.

FIG. 1 shows a method 100 in accordance with an embodiment of the present disclosure. The method of making magnetic nanoparticles can include combining an iron precursor and a surfactant in an organic solvent (step 102), heating the iron precursor and the surfactant to form a first population of magnetic nanoparticles (step 104), and combining the first population of magnetic nanoparticles with additional amphiphilic small molecules or polymers to form a second population of magnetic nanoparticles (step 106).

In one example embodiment, the methods of the present disclosure include a method of making a population of magnetic nanoparticles that includes combining an iron precursor and a surfactant in an organic solvent to form an iron precursor solution. The ratio of surfactant to iron precursor can be, for example, greater than 10:1. The method further includes heating the iron precursor solution to form a first population of magnetic nanoparticles, and combining the first population of magnetic nanoparticles with an amphiphilic polymer to form a second population of magnetic nanoparticles that include the amphiphilic polymer. The second population of magnetic nanoparticles can have a narrow size distribution (e.g., a multiplicative standard deviation of less than about 1.35) and be dispersible in an aqueous solution.

As provided herein, iron precursor solutions of the present disclosure can include an iron precursor. A variety of iron precursor materials can be selected for making the magnetic nanoparticles. The iron precursor can include iron in a reduced or an oxidized (e.g., ferrous or ferric) state. In some embodiments, the iron precursor includes an iron ion (e.g., $Fe^{3+}$) complexed with at least one other molecule. For example, the iron precursor can have the formula: $Fe^{3+}(R^1)_3$, in which $R^1$ can include any compound capable of complexing with ferric iron to facilitate production of the magnetic nanoparticles. In one embodiment, the iron precursor has the formula: $Fe^{3+}(R^1)_3$ wherein $R^1$ is a substituted or unsubstituted saturated $C_1$-$C_{24}$ carboxylic acid or a substituted or unsubstituted unsaturated $C_1$-$C_{24}$ carboxylic acid. In some embodiments, the iron precursor includes $Fe^{3+}$-oleate or $Fe^{3+}$-stearate The iron precursor solutions used in making magnetic nanoparticles can further include a surfactant. The surfactant, for example, can be combined with the iron precursor for stabilization. A wide range of surfactants can be used. In some embodiments, the surfactant can include a substituted or unsubstituted $C_1$-$C_{24}$ alkane or a substituted or unsubstituted $C_1$-$C_{24}$ alkene. For example, the surfactant can include oleylamine. In certain embodiments, the surfactant can be a carboxylic acid. The carboxylic acid can be a substituted or unsubstituted saturated $C_1$-$C_{24}$ carboxylic acid or a substituted or unsubstituted unsaturated $C_1$-$C_{24}$ carboxylic acid. For example, the carboxylic acid can be oleic acid. Other types of surfactants, e.g., alkyl phosphines can be used. Alkylphosphine surfactants can include but are not limited to trioctylphosphane oxide (TOPO). In certain embodiments, the iron precursor can be combined with any combination of the surfactants described herein.

Substituents for the substituted compounds described herein (e.g., substituted $C_1$-$C_{24}$ alkane or a substituted $ClC_1$-$C_{24}$ alkene) can be one or more of a variety of groups selected from, but not limited to: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. When a compound disclosed herein includes more than one R group, for example, each of the R groups is independently selected as are each R', R", R'" and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

As provided herein, the present disclosure is based in-part on the discovery that the ratio of surfactant to iron precursor surprisingly can play a role in making magnetic nanoparticles with a narrow size distribution that can, for example, enhance magnetic properties and their uses. For example, lower molar ratios from 1:1 to 4:1 surfactant:iron precursor have been used to make magnetic particles. However, it was discovered that a large excess of surfactant as compared to iron precursor could be used to make magnetic nanoparticles. In particular, high ratios would have been expected to inhibit nucleation and particle growth. Surprisingly, high molar ratios of surfactant to iron precursor can be used to make populations of magnetic nanoparticles having narrow size distributions that have not been previously realized. The molar ratios of surfactant to iron precursor can range, for example, from greater than 5:1, greater than 10:1, greater than 15:1, greater than 20:1, and greater than 25:1. In some embodiments, the molar ratio of surfactant to iron precursor ranges from about 5:1 to about 40:1, from about 10:1 to about 40:1, from about 10:1 to about 30:1, and from about 10:1 to about 20:1. In certain embodiments, the molar ratio of surfactant to iron precursor is about 5:1, about 10:1, about 15:1, about 20:1, about 25:1, about 30:1, about 35:1 or about 40:1.

Organic solvents can also be included in the iron precursor solutions and other steps in the methods described herein. Organic solvents, for example, can be used in amounts that facilitate adjustment of the molar ratio of surfactant to iron precursor. The organic solvent includes a non-polar solvent. The selection of an organic solvent may under certain conditions depend on the surfactant and/or iron precursor being used. In some embodiments, the organic solvent includes a substituted or unsubstituted $C_1$-$C_{24}$ alkane or a substituted or unsubstituted $C_1$-$C_{24}$ alkene. In certain embodiments, the organic solvent includes octadecene. In some embodiments, the organic solvent can include oleylamine.

To allow for nucleation and particle growth at higher ratios of surfactant to iron precursor, certain steps can be taken during the methods of making magnetic nanoparticles. For example, solutions including iron precursor and surfactant can be heated under a given temperature and/or pressure for an extended period of time, e.g., longer than about 24 hours. In certain embodiments, nucleation of the magnetic nanoparticles can be delayed until after the iron precursor solution has been refluxed (e.g., heated) for between one to four hours, depending on the surfactant to iron precursor molar ratio. In certain embodiments, a higher ratio corresponds to longer times until nucleation begins. In addition, growth of the magnetic nanoparticles after nucleation can be longer than processes that involve low (e.g., 1:1) surfactant to iron precursor molar ratios. Depending on the high surfactant to iron precursor molar ratio used, the methods of making magnetic nanoparticles described herein can include heating processes longer than about 20 hours, longer than about 22 hours, longer than about 24 hours, and/or longer than about 26 hours.

Without being bound to any particular theory, it is believed that during the longer heating periods consistent with the present disclosure iron precursor concentration gradually reaches super-saturation due to gradual decomposition of the surfactant. For example, with methods including $Fe^{3+}$-oleate as the iron precursor, the surfactant oleic acid can begin to dissociate from iron atoms at temperatures above 250° C. Heating at a temperature, for example, of 320° C. can cause gradual decomposition of the oleic acid thereby allowing for nucleation and then growth to occur. A longer period for growth, e.g., longer than 24 hours, may be due to a mechanism in which the acidic surfactant (e.g., oleic acid) partially dissolves the particles at the surface during the growth process, thus competing with ongoing growth and extending the growth time.

In certain embodiments, heating the iron precursor solutions described herein can include a variety of different heating phases. In some embodiments, heating the iron precursor solution can include a gradient temperature heating phase and a stable temperature heating phase. The order and duration of these phases can depend on the particular iron precursor, surfactant and/or organic solvent being used. For example, heating the iron precursor solution can include a gradient temperature heating phase followed by a stable temperature phase or vice versa. Rates of temperature increase during the gradient heating phase can be, for example, about 1° C./minute, about 2° C./minute, about 3° C./minute, 5° C./minute, about 10° C./minute, about 20° C./minute, about 30° C./minute, or about 40° C./minute. In an example embodiment using oleic acid, heating can include a gradient heating phase in which the iron precursor solution is heated to 320° C. at a rate of about 30° C./minute. Upon reaching 320° C., the solution can then be held at a stable temperature during a stable heating phase of longer than about 24 hours, or some other specified time (e.g., longer than 20 hours) that allows for production of the magnetic nanoparticles. In certain embodiments, the heating of the precursor solution can further include purging the solution under, for example, an argon and/or nitrogen atmosphere.

The surface properties of the magnetic nanoparticles provided herein can also be modified to effect solubility in non-polar and/or polar solvents. In certain embodiments, magnetic nanoparticles can undergo a phase transfer in which the surface of the magnetic nanoparticles is modified from a surface soluble in the non-polar organic solvent to a surface that is soluble in polar solvent, e.g., aqueous solution. For example, the methods of making magnetic nanoparticles can include forming a first population of magnetic nanoparticles that are not soluble (e.g., sparingly soluble) in aqueous solution. The first population of magnetic nanoparticles can be combined with an amphiphilic molecule, e.g., an amphiphilic polymer that modifies the surface of the magnetic nanoparticles, thereby making them dispersible in aqueous solution. The amphiphilic molecules or polymers can associate with the magnetic nanoparticles, for example, by covalent and/or non-covalent interactions with the surface of the magnetic nanoparticles. Moreover, surprisingly, the phase transfer process can actually cause a further narrowing on the size distribution for a population of magnetic nanoparticles. For example, a first population of magnetic nanoparticles produced in the iron precursor solution may have a broader size distribution than a second population of magnetic nanoparticles that is produced from a phase transfer process by, e.g., coating the magnetic nanoparticles with amphiphilic polymer.

A variety of amphiphilic molecules (e.g., polymers) can be used in the present disclosure. Suitable amphiphilic polymers include but are not limited to ethylene oxide/propylene oxide block copolymer, polyethylene oxide polymer, polyethylene glycol polymer, poly (maleic anhydride alt-1-octadecene) polymer and/or poly (maleic anhydride alt-1-octadecene)-polyethylene glycol polymer (PMAO-PEG). The amphiphilic polymers can have a wide range of molecular weights and can be linear or branched. In certain embodiments, the amphiphilic polymer can include Pluronic® F127. In some embodiments, the amphiphilic polymer can include PMAO-PEG. In one embodiment, the PMAO-PEG polymer can have a PMAO portion with a $M_n$~30,000-50,000 and a PEG portion with a $M_n$~5000. In some embodiments, the PMAO portion can range from about 1,000 to about 50,000, from about 5,000 to about 40,000, from about 10,000 to about 30,000, or from about 20,000 to about 50,000. Higher molecular weights can also be used. In some embodiments, the PEG portion can include, but is not limited to, PEG500, PEG1000, PEG2000, PEG5000, PEG 10000, and higher.

III. Systems and Methods of Using Magnetic Nanoparticles

The magnetic nanoparticles of the present disclosure may find use in a wide variety of applications. For example, the present disclosure provides diagnostic and/or therapeutic methods of using magnetic nanoparticles described herein. In some embodiments, for example, the present disclosure provides methods for imaging magnetic nanoparticles that include administering a population of magnetic nanoparticles described herein to a subject and exciting at least one magnetic nanoparticle in the population of magnetic nanoparticles with an imaging system. The method can further include detecting a signal from at least one excited magnetic nanoparticle in the population of magnetic nanoparticles.

Figure 2:
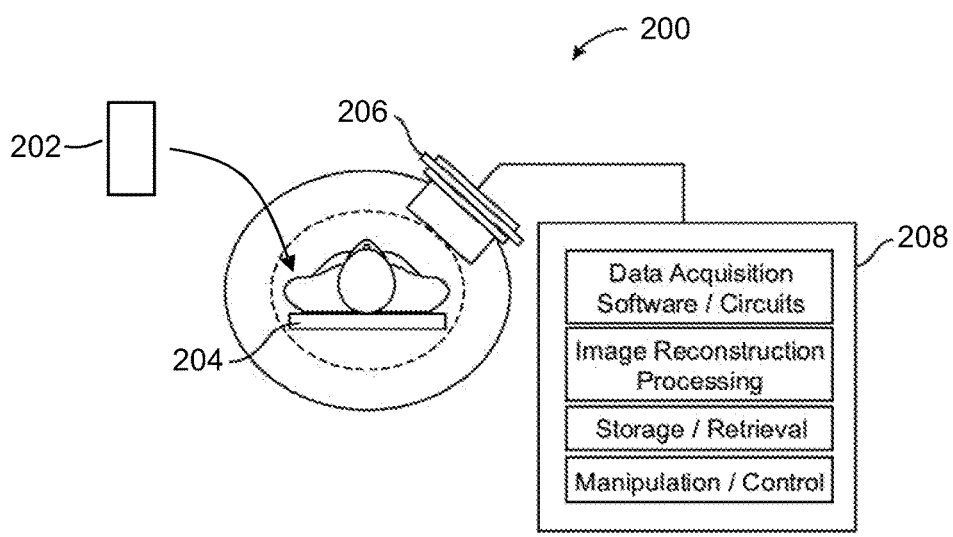
FIG. 2 shows an imaging system in accordance with an embodiment of the present disclosure.

FIG. 2 illustrates various aspects of the present disclosure. For example, FIG. 2 illustrates a composition of magnetic nanoparticles 202 that can be delivered to a patient or subject prior to imaging. FIG. 2 also illustrates a basic configuration of an imaging system 200. The system 200 can, for example, include configurations/components commonly employed in known imaging systems. As shown, the imaging system 200 includes a patient or subject area 204 (positioned subject shown for illustrative purposes), a detector assembly 206 and a computer control unit 208. The computer control unit may include circuitry and software for data acquisition, image reconstruction and processing, data storage and retrieval, and manipulation and/or control of various components/aspects of the system. For certain applications, the detector assembly and subject area may be movable with respect to each other, and may include moving the detector assembly with respect to the subject area and/or moving the subject area with respect to the detector assembly. The components shown in FIG. 2 are provided for general illustrative purposes. One of ordinary skill will appreciate the modifications that would be associated with conducting different diagnostic (e.g., MPI and/or MRI) and/or therapeutic (e.g., MFH) techniques. For example, for MRI applications, the detector assembly 206 can be in the form of a conventional MRI scanner that houses the subject. Similarly, an assembly conventionally known for use with MPI can be arranged around the subject in place of the detector assembly 206.

A variety of imaging systems can be used to detect the magnetic nanoparticles in a subject, which can include but is not limited to an object, a plant, an animal, a mammal, or a human. In certain embodiments, the imaging systems can be configured to perform magnetic particle imaging (MPI) and/or magnetic resonance imaging (MRI). Commercially available and/or custom-built MPI and/or MRI systems can be used. MPI imaging can be carried out under a range of frequencies and amplitudes. In certain embodiments, the MPI imaging system can employ a frequency ranging between about 1 kHz to about 250 kHz, between about 1 kHz to about 100 kHz, and between about 1 kHz to about 25 kHz. Higher or lower frequencies can also be used.

The present disclosure also provides therapeutic methods that employ the magnetic particles described herein. In an example embodiment, the present disclosure provides a method of performing magnetic hyperthermia. The method includes administering a population of magnetic nanoparticles described herein to a subject and heating a cell in the vicinity of at least one of the magnetic nanoparticles in the population of magnetic nanoparticles. Heating of the magnetic nanoparticles can be accomplished using commercially available or custom built hyperthermia systems that, for example, can radiate the magnetic nanoparticles with an alternating magnetic field at a specified frequency and amplitude.

The present disclosure can further include selecting a particular magnetic nanoparticle size that is optimized for diagnostic and/or therapeutic applications described herein. For example, the present disclosure provides a method of producing magnetic nanoparticles with a tuned size distribution for magnetic particle imaging. The method can include selecting a diameter of a magnetic nanoparticle that produces a maximum signal at a frequency used in magnetic particle imaging and producing a population of magnetic nanoparticles having a median diameter approximately equal to the selected diameter of the magnetic nanoparticle that produces the maximum signal. The population of the magnetic nanoparticles can further have a narrow size distribution, as described above. In some embodiments, the present disclosure provides a method of producing magnetic nanoparticles with a tuned size distribution for magnetic particle imaging that can include selecting a diameter of a magnetic nanoparticle that produces a maximum spatial resolution at a frequency used in magnetic particle imaging and producing a population of magnetic nanoparticles having a median diameter approximately equal to the selected diameter of the magnetic nanoparticle that produces the narrowest spatial resolution. The population of the magnetic nanoparticles can further have a narrow size distribution, as described above.

Selecting a diameter of a magnetic nanoparticle that produces a maximum signal and/or a maximum spatial resolution can be performed through a variety of ways. For example, mathematical models can be used to simulate how a system of magnetic nanoparticles, with a selected diameter, will respond to an ac magnetic field to generate harmonics and therefore a signal recognized by, e.g., a magnetic particle imaging system. In one embodiment, the following model can be used: Magnetic nanoparticle susceptibility $\chi$ is modeled using the complex convention first developed to describe the permittivity of polar dielectrics in solution by Debye, such that $$\chi = \chi' - i\chi'' = \frac{\chi_0}{1+(\omega\tau)^2} - i\frac{\omega\tau}{1+(\omega\tau)^2}\chi_0, \quad (2)$$

where $\omega$ is the angular frequency of the applied magnetic field, $\tau$ is the time for the magnetic nanoparticle magnetic moment to reverse its direction, and $\chi_0$ is the equilibrium susceptibility. For this approximation to be strictly valid, relaxation should be rotational and domain processes excluded and all particles should have identical size and shape.

Thus, for a driving field of the form $$H(t) = H_0 \cos \omega t = Re[H_0 e^{i\omega t}]. \quad (3)$$

the magnetic nanoparticle magnetization is $$M(t) = Re[\chi H_0 e^{i\omega t}] = H_0(\chi' \cos \omega t + \chi'' \sin \omega t) \quad (4)$$

and M(t) contains both in-phase and out-of-phase terms due to the complex form of Eq. (2). The nonlinear equilibrium susceptibility $\chi_0$ of superparamagnetic magnetic nanoparticles can be described by the Langevin function such that $$\chi_0 = \frac{M(H_0)}{H_0} = \frac{M_s}{H_0}\mathcal{L}(\alpha), \quad (5)$$

$$\text{where } \alpha = \frac{\mu_0 H_0 M_s \pi d^3}{6k_b T},$$

$\mu_0$ is $4\pi \times 10^{-7}$ (Henry m$^{-1}$), $H_0$ is the equilibrium magnetic field strength in T $\mu_0^{-1}$, $k_b$ is the Boltzmann constant, $1.38 \times 10^{-23}$ (JK$^{-1}$), T is the temperature in Kelvin, and the magnetic moment of each particle is expressed in terms of the diameter d of its magnetic volume and volume saturation magnetization Ms in kA m$^{-1}$ (446 for bulk magnetite).

Magnetic nanoparticle susceptibility depends on the effective relaxation time $\tau$ for the magnetic nanoparticle moment to reverse in an alternating magnetic field $$\tau = \tau_B \tau_N/(\tau_B + \tau_N), \quad (6)$$

which includes two distinct relaxation processes, each with a characteristic time. For small-amplitude applied fields, the Néel relaxation time $\tau_N$ describes the magnetic reversal of an "unblocked" volume $$\tau_N = \frac{\sqrt{\pi}}{2}\tau_0 \frac{\exp[K\rho]}{(K\rho)^{1/2}}, \quad (7)$$

where K (Jm$^{-3}$) is the magnetocrystalline anisotropy constant, a material property $$\rho = \frac{\pi d^3}{6k_b T},$$

and the attempt time $\tau_0$ is $\sim 10^{-10}$ seconds. The Brownian relaxation time, $\tau_B$ describes the physical rotation of a "blocked" magnetic volume $$\tau_0 = \frac{3\eta\pi d_N^3}{6k_b T}, \quad (8)$$

where $d_H$ is the magnetic nanoparticle hydrodynamic diameter and $\eta$ (Pa sec) is the viscosity of the suspending fluid (0.89 for water). Equation (4) can also be modified to describe the magnetization M(t) of magnetic nanoparticles having a distribution of diameters g(d) in an alternating field of the form given in Equation 3, such that $$M(t) = \qquad (9)$$
$$M_s \int_0^\infty \left(\frac{1}{1+(\omega\tau)^2}\mathcal{L}(\alpha\cos\omega t) + \frac{\omega\tau}{1+(\omega\tau)^2}\mathcal{L}(\alpha\sin\omega t)\right)g(d)\,dd \bigg|.$$

The diameter distribution g(d) is described above in Equation (1).

The present disclosure also provides methods and compositions for administering the magnetic nanoparticles described herein to a subject to facilitate diagnostic and/or therapeutic applications. In certain embodiments, the compositions can include a population of magnetic nanoparticles and a pharmaceutically acceptable excipient. Pharmaceutical excipients useful in the present disclosure include, but are not limited to, binders, fillers, disintegrants, lubricants, coatings, sweeteners, flavors and colors. One of skill in the art will recognize that other pharmaceutical excipients are useful in the present disclosure.

The magnetic nanoparticles of the present disclosure can be administered as frequently as necessary, including hourly, daily, weekly or monthly. The compounds utilized in the methods of the disclosure are administered at dosages ranging from, for example, about 1 mg to about 510 mg, or about 0.0125 mg/kg body weight to about 6.375 mg/kg body weight (assuming an average adult weighs 80 kg). The dosages, however, may be varied depending upon the requirements of the patient, the severity of the condition being treated and/or imaged, and/or the magnetic nanoparticle being employed. For example, dosages can be empirically determined considering the type and stage of disease diagnosed in a particular patient and/or the type of imaging modality being used in conjunction with the magnetic nanoparticles. The dose administered to a patient, in the context of the present disclosure should be sufficient to effect a beneficial diagnostic or therapeutic response in the patient. The size of the dose also will be determined by the existence, nature, and extent of any adverse side-effects that accompany the administration of a particular magnetic nanoparticle in a particular patient. Determination of the proper dosage for a particular situation is within the skill of the practitioner.

The compositions described herein can be administered to the patient in a variety of ways, including parenterally, intravenously, intradermally, intramuscularly, colonically, rectally or intraperitoneally. Preferably, the pharmaceutical compositions are administered parenterally, intravenously, intramuscularly or orally. The oral agents comprising a population of the magnetic nanoparticles of the disclosure can be in any suitable form for oral administration, such as liquid, tablets, capsules, or the like. The oral formulations can be further coated or treated to prevent or reduce dissolution in stomach.

The magnetic nanoparticle compositions of the present disclosure can be administered to a subject using any suitable methods known in the art. Suitable formulations for use in the present disclosure and methods of delivery are generally well known in the art. For example, a population of magnetic nanoparticles described herein can be formulated as pharmaceutical compositions with a pharmaceutically acceptable diluent, carrier or excipient. A population of magnetic nanoparticles of the present disclosure can be administered in any pharmaceutically acceptable composition. A pharmaceutically acceptable nontoxic composition is formed by incorporating any of normally employed excipients, and 10-95% of active ingredient or at a concentration of 25%-75%. Furthermore, in some embodiments, various carrier systems, such as nanoparticles, microparticles, or liposomes, etc. can be used. For example, magnetic nanoparticles can be encapsulated with other nanoparticles, e.g., liposomes. This approach can, for example, allow for a higher density of magnetic nanoparticles in an area, thereby influencing diagnostic and/or therapeutic applications. In addition, the magnetic nanoparticles can be further combined with drug delivery methodologies generally known in the art that, for example, employ nanoparticles for targeted drug delivery to a patient.

Furthermore, a population of magnetic nanoparticles can be formulated for parenteral, topical, nasal, sublingual, gavage, or local administration. For example, the pharmaceutical compositions are administered parenterally, e.g., intravenously, subcutaneously, intradermally, or intramuscularly, or intranasally. Thus, the disclosure provides compositions for parenteral administration that comprise a solution of a single or mixture of a population of magnetic nanoparticles described herein, dissolved or suspended in an acceptable carrier, preferably an aqueous carrier. A variety of aqueous carriers may be used. These compositions may be sterilized by conventional, well known sterilization techniques, or they may be sterile filtered. The resulting aqueous solutions may be packaged for use as is or lyophilized, the lyophilized preparation being combined with a sterile solution prior to administration. The compositions may contain pharmaceutically acceptable auxiliary substances as required to approximate physiological conditions including pH adjusting and buffering agents, tonicity adjusting agents, wetting agents and the like, such as, for example, sodium acetate, sodium lactate, sodium chloride, potassium chloride, calcium chloride, sorbitan monolaurate, triethanolamine oleate, etc.

The present disclosure also provides kits for administering the magnetic nanoparticles to a subject for treating and/or diagnosing a disease state. Such kits typically include two or more components useful for administration. Components can include magnetic nanoparticles of the present disclosure, reagents, containers and/or equipment. In some embodiments, a container within a kit may contain a magnetic nanoparticle composition including a radiopharmaceutical that is radiolabeled before use. The kits can further include any of the reaction components or buffers necessary for administering the magnetic nanoparticle compositions. Moreover, the magnetic nanoparticle compositions can be in lyophilized form and then reconstituted prior to administration.

In certain embodiments, the kits of the present disclosure can include packaging assemblies that can include one or more components. For example, a packaging assembly may include a container that houses at least one of the magnetic nanoparticle compositions as described herein. A separate container may include other excipients or agents that can be mixed with the magnetic nanoparticle compositions prior to administration to a patient. In some embodiments, a physician may select and match certain components and/or packaging assemblies depending on the particular diagnostic and/or therapeutic application.

IV. Polymer-Coated Magnetic Nanoparticles

In view of the above disclosure and related Examples below, further embodiments related to specific polymeric coatings applied to magnetic nanoparticles to provide advantageous attributes to the coated magnetic nanoparticles. Accordingly, disclosed herein are polymer-coated iron oxide magnetic nanoparticles and methods of their manufacture and use. The nanoparticles are coated with a copolymer of poly(maleic anhydride alt-$H_2C$=CH—$R_1$)-polyethylene glycol (PMAR-PEG), wherein $R_1$ is a hydrophobic moiety. The molecular weights of the PMAR and PEG portions of the copolymer, as well as the core diameter of the nanoparticles are selected in order to produce optimal performance for specific applications. Representative applications of the nanoparticles include magnetic particle imaging (MPI), magnetic sentinel lymph node biopsy (SLNB), and magnetic fluid hyperthermia (MFH). The disclosed nanoparticles are tools for these methods that provide previously unachieved levels of stability and customizability to iron oxide nanoparticles.

In one aspect, a plurality of nanoparticles is provided. The nanoparticles are referred to herein as nanoparticles (NP), magnetic nanoparticles (MNP), and superparamagnetic iron oxide nanoparticles (SPIONs).

In one embodiment, each nanoparticle includes:

a core comprising iron oxide, wherein the core has a diameter of 15 nm to 30 nm; and a coating surrounding the core, the coating comprising a PMAR-PEG copolymer having a poly(maleic anhydride alt-H2C=CH—R1) (PMAR) portion and a plurality of polyethylene glycol (PEG) portions each with a molecular weight (Mn) of 10,000 Da or greater;

wherein R1 is a hydrophobic moiety.

The combination of the specific size range of the core, coupled with the specific composition of the coating, provides the nanoparticles with unexpectedly superior properties compared to known nanoparticles. These benefits include, but are not limited to, improving dispersal in water, preventing aggregation, and preserving the nonlinear magnetic response or AC-susceptibility in aqueous media and serum-containing in vivo environments, such as circulating blood. Furthermore, the molecular weight and surface density of PEG chains conjugated to the PMAR can be tailored to tune the in vivo blood half-life of nanoparticles injected intravenously or through a catheter in order to provide sustained nonlinear magnetic signal for first-pass and steady-state imaging or detection.

FIG. 16 schematically illustrates an exemplary magnetic nanoparticle in accordance with the disclosed embodiments. The nanoparticle includes PMAO-PEG coating on oleic acid coated nanoparticles. The hydrophobic alkyl chains (C16) in PMAO intercalate with oleic acid chains and are bound by hydrophobic van der Waals forces.

Iron Oxide Core

The core of the nanoparticles is iron oxide. Any iron oxide can be used in the nanoparticles. In one embodiment, the iron oxide is selected from the group consisting of wüstite, magnetite, maghemite, and combinations thereof. In one embodiment the iron oxide is wüstite. In one embodiment, the iron oxide is magnetite. In one embodiment, the iron oxide is maghemite. Iron oxide cores are generally known to those of skill in the art but their size, distribution and phase purity must be carefully selected to have appropriate magnetic relaxation characteristics.

The size or diameter of the iron oxide nanoparticle cores can be determined, for example, by transmission electron microscopy (TEM).

In one embodiment, the core has a diameter ("size") of 15 nm to 30 nm. It has been determined that this core size range is valuable for applications such as MPI. Example 8 illustrates the inferiority of cores smaller than 15 nm in diameter. The optimal core size range for the system of Example 8 is 23-27 nm.

Known coatings fail to provide optimal properties within the 15 nm to 30 nm core size range. For example, known coatings allow for aggregation, which attenuates magnetic signal strength. The larger the core, the more the forces lead to aggregation. Accordingly, improved coatings for the iron oxide cores address these deficiencies. In a further embodiment, the core has a diameter of 18 nm to 30 nm. In yet a further embodiment, the core has a diameter of 23 nm to 30 nm. In another embodiment, the core has a diameter of 23 nm to 27 nm.

In one embodiment, the cores are monodisperse, as defined by their having a diameter distribution with geometric standard deviation of equal to or less than 1.35 when a log-normal distribution function is used. In another embodiment, the cores are monodisperse, as defined by their having a diameter distribution with geometric standard deviation of equal to or less than 1.11 when a log-normal distribution function is used. As used herein, the geometric standard deviation of a plurality of nanoparticles is defined as relating to how spread out are the particle diameters in the sample, with 68% of the samples falling between the lower bound set by $d_0/exp\,(\sigma)$ and the upper bound $d_0*exp\,(\sigma)$, where $d_0$ is the median diameter of the distribution and $exp\,(\sigma)$ is the geometric standard deviation. An exemplary calculation of the geometric standard deviation is included in the Examples below.

A log-normal distribution may be applied to the data even if the data do not perfectly fit the log-normal distribution. Furthermore, the distribution function may obey other relationships besides a log-normal distribution, including a normal distribution, a bimodal distribution, and any other relationship known to those of skill in the art.

Relevant to the monodispersity of the nanoparticles is the large number of nanoparticles that comprise the plurality of nanoparticles. Maintaining monodispersity is important because it provides uniform characteristics that translate to optimized, reproducible and predictable magnetic performance and stability in aqueous, in vitro and in vivo environments. Many physical properties of nanoparticles vary exponentially with particle size, with some sizes being well-suited to a particular application and other sizes being ill-suited. Monodisperse samples can be optimized for an application by making all particles very nearly the optimum size. Polydisperse samples cannot be optimized, since they contain both desirable and undesirable sizes. Monodiserse magnetic nanoparticles provide more intense signals, whereas polydisperse magnetic nanoparticles often give broad and lower intensity signal response.

In one embodiment, the plurality of nanoparticles is 100 or more nanoparticles. In one embodiment, the plurality of nanoparticles is 1,000 or more nanoparticles. In one embodiment, the plurality of nanoparticles is 1,000,000 or more nanoparticles. When considering the number of nanoparticles required for a particular application, the primary factor is the amount of iron oxide, which is defined by the size and number of nanoparticles. As an example, for a mouse circulation time study using MPI a typical injection is about 0.1 mg of iron oxide, which contains about $3.3 \times 10^{12}$ nanoparticles with a 25 nm core diameter.

In one embodiment, the coating is attached to the core by a mechanism selected from the group consisting of covalent bonding, ionic bonding, van der Waals forces, and hydrophobic/hydrophobic interactions.

In certain embodiments, the core comprises an attachment layer on its surface that provides functionality such that the coating adheres to the core. An exemplary attachment layer is oleic acid, which provides hydrophobic moieties extending from the core surface, which can facilitate hydrophobic-hydrophobic bonding.

Polymer Coating

A coating surrounds the core in order to decrease aggregation between nanoparticles and preserve magnetic characteristics of the core. As used herein, the term "surrounds" includes both complete surface coverage, as well as partial surface coverage. In one embodiment, the coating completely surrounds the core. In another embodiment, the coating partially surrounds the core. In one embodiment, at least a portion of the plurality of nanoparticles comprises a single core surrounded with the coating.

The coating provides both physical and magnetic isolation between adjacent nanoparticles. Specifically, the coating minimizes magnetic dipole-dipole interactions between individual nanoparticles, minimizing clustering and aggregation and preserving their nonlinear magnetic response in alternating magnetic fields used in inductive measurement techniques. As a result, the induced signal is quantitative (linear with concentration) and remains unchanged after administration in in vivo environments (e.g. intravenous injection), thus enabling high quality imaging or detection, and quantitation. In one embodiment, the nanoparticle relaxation or magnetic moment reversal of each core is independent of an adjacent nanoparticle.

The coating includes an amphiphilic polymer. Generally, the coating comprises a PMAR-PEG copolymer having a poly(maleic anhydride alt-H2C=CH—R1) (PMAR) portion and a plurality of polyethylene glycol (PEG) portions each with a molecular weight (Mn) of 10,000 Da or greater; wherein R1 is a hydrophobic moiety. As used herein, a hydrophobic moiety is any chemical moiety that provides hydrophobic character. Representative hydrophobic moieties include alkyl and alkenyl groups, both substituted and unsubstituted. In one embodiment, R1 is a C6 to C18 hydrocarbon.

When the core includes an adhesion layer that is hydrophobic, the hydrophobic moiety of the PMAR-PEG polymer provides an attaching force The PMAR-PEG polymer is of the type typically embodied by poly(maleic anhydride alt-octadecene)-PEG, referred to as "PMAO-PEG." Accordingly, in one embodiment, the PMAR portion is PMAO and thus the PMAR-PEG polymer is PMAO-PEG.

The PMAR-PEG polymer is configured as a pendant-type copolymer, with the PMAR portion forming the backbone and the PEG portions pendant off of the PMAR portion. PMAR provides functional binding sites such that up to two PEG portions can be bound to each PMAR monomer. PEGs are grafted onto the PMAR portion by reacting carboxylates on the PMAR portion with terminal hydroxyl or primary amines on the PEG portions to form ester or amide bonds, respectively.

The amount of PEG bound to the PMAR is referred to herein as the PEG "loading." The loading is a percentage based on the number of PEG portions attached to the available number of carboxylates of the PMAR portion, given the presence of 2 carboxylates per maleate in the PMAR portion. In one embodiment, the PMAR-PEG copolymer has 1% to 50% PEG loading. In one embodiment, the PMAR-PEG copolymer has 12.5% to 25% PEG loading.

As used herein, all molecular weights (MW) are referred to by number average molar mass, denoted Mn, unless otherwise noted. The PMAR we have used to illustrate the technology is PMAO with a molecular weight (Mn) of 30,000 Da to 50,000 Da. In considering the MW or polymer length of PMAR, it should be of sufficient length to maintain strong binding to the nanoparticle surface via the hydrophobic moieties (R1).

In one embodiment, the PMAR portion has a molecular weight (Mn) of 1,000 Da to 100,000 Da. In one embodiment, the PMAR portion has a molecular weight (Mn) of 10,000 Da to 70,000 Da. In a further embodiment, the PMAR portion has a molecular weight (Mn) of 30,000 Da to 50,000 Da. This size range for the PMAR portion provides hydrophobic moieties sufficient to attach the PMAR-PEG polymer to the core. The PMAR portion additionally provides a structure onto which PEG portions are attached.

The molecular weight of the PEG portions strongly defines the character of the nanoparticle properties. A plurality of the PEG portions each have a molecular weight (Mn) of 10,000 Da or greater. PEG portions with a molecular weight greater than 10,000 Da were found to reduce aggregation while preserving magnetic properties of the cores, as illustrated in Examples 6, 7, and 12.

In certain embodiments, all of the PEG portions have a MW of 10,000 Da or greater. However, in other embodiments, less than all of the PEG portions have a MW of 10,000 Da or greater.

In certain embodiments, the PEG portions have a molecular weight (Mn) of 15,000 Da or greater. In certain embodiments, the PEG portions have a molecular weight (Mn) of 20,000 Da or greater.

While greater PEG MW provides strong anti-aggregation effects and improved nanoparticle properties, if the PEG MW is too high deleterious effects can occur. For example, relatively high MW PEG (e.g., greater than 40 k Da) becomes highly viscous due to entanglement of PEG chains. The reaction dynamics when synthesizing the PMAR-PEG are adversely affected by the increased PEG MW and coupling to the PMAR is negatively impacted. Furthermore, high MW PEG is not typically commercially available or, if available, expensive. Finally, increasing PEG MW leads to increased hydrodynamic diameter of the nanoparticles, which affects in vivo performance due to filtering by the body (e.g., spleen). As the hydrodynamic diameter reaches further above 100 nm, the more likely the particles will be screened from the blood and eliminated, or in the case of sentinel lymph node detection, lead to poor lymph node uptake and retention [Swartz, adv. *Drug delivery Rev* 2001; 50; 3-20]. Therefore, using high MW PEG effectively leads to reduced blood lifetime or lymph node uptake of the nanoparticles, which is detrimental to the applications disclosed herein.

Accordingly, in certain embodiments the PEG portions have a molecular weight (Mn) of 30,000 Da or less. In a further embodiment, the PEG portions have a molecular weight (Mn) of 40,000 Da or less. In yet a further embodiment, the PEG portions have a molecular weight (Mn) of 50,000 Da or less. It is anticipated that PEG MW greater than 50,000 Da will be incompatible with the disclosed embodiments, or will not provide additional benefit beyond what is described herein.

In one embodiment the PEG portions have a molecular weight (Mn) of 10,000 Da to 50,000 Da. In one embodiment the PEG portions have a molecular weight (Mn) of 15,000 Da to 40,000 Da. In one embodiment the PEG portions have a molecular weight (Mn) of 15,000 Da to 30,000 Da. In one embodiment the PEG portions have a molecular weight (Mn) of 10,000 Da to 20,000 Da. In one embodiment the PEG portions have a molecular weight (Mn) of 15,000 Da to 25,000 Da.

While certain embodiments include further copolymers beyond PEG and PMAO, in one embodiment, the coating consists essentially of the PMAR-PEG copolymer.

The molecular weight and surface density of PEG portions can be modified to optimize colloidal stability of the nanoparticles, with negligible inter-particle dipolar interactions, preserve their nonlinear magnetic response in alternating magnetic fields, and also tune their blood half-life after intravenous injection. With regard to the behavior of nanoparticles in blood, Example 9 demonstrates signal linearity in blood; Example 10 demonstrates signal stability in vivo; and Example 11 demonstrates the tunability of blood half-life based on alteration of the PEG molecular weight and/or PEG loading.

The blood half-life can be modified to enable first-pass cardiovascular MPI imaging, such as coronary angiography after intracatheter administration in coronary artery, and steady state imaging of the vascular system after intravenous or intracatheter administration.

There is strong interplay between the core diameter, the molecular weight of the individual PEG portions, and the PEG loading. As the core diameter increases, more PEG is required to prevent aggregation and maintain magnetic properties. Increased PEG is achievable through increased PEG molecular weight, increased PEG loading, or a combination of the two. Relatively small core diameter nanoparticles according to the present disclosure, for example less than 20 nm, may be sufficiently protected with a coating comprising 10,000 Da PEG portions at a PEG loading of 8%. However, increasing the core diameter to 23 nm requires PEG of 20,000 Da or greater and at least 12.5% PEG loading.

The nanoparticles can be formed using any methods known to those of skill in the art. In the exemplary embodiments disclosed herein (in the Examples below), the core is synthesized in organic solvents and then transferred from the organic to aqueous phase using the amphiphilic polymer. Hydrophobic-hydrophilic interactions attach the polymer to the cores in the aqueous phase.

In one embodiment, the polymer coating is a polymer:

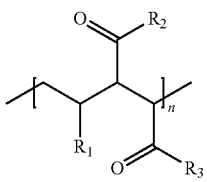

Wherein $R_1$ is a hydrophobic moiety (e.g., an alkyl of C6-C18 length).

Wherein $R_2$ comprises from 2% to 100% of —NH—$R_4$ or —O—$R_4$ and the remaining percentage of $R_2$ is selected from one or more of the following: —OH (or —O$^-$), —NH2, —NHCH$_2$CH$_2$CH$_2$N(CH$_3$)$_2$, —NHCH$_3$, —NHCH$_2$CH$_3$, —NHR$_5$, —OR$_5$ or other hydrophilic moiety.

Wherein $R_3$ is selected from one or more of the following: —OH (or —O$^-$), —NH$_2$, —NHCH$_2$CH$_2$CH$_2$N(CH$_3$)$_2$, —NHCH$_3$, —NHCH$_2$CH$_3$, —NHR$_5$, —OR$_5$ or other hydrophilic moiety.

$R_4$ is a polyethyleneglycol chain with a molecular weight (Mn) of 10,000 Da or more.

$R_5$ is a polyethyleneglycol chain with a molecular weight (Mn) of 5,000 Da of less.

In certain embodiments $R_4$ is a polyethyleneglycol chain with a molecular weight (Mn) of 40,000 Da or less. In one embodiment $R_4$ is a polyethyleneglycol chain with a molecular weight (Mn) of 15,000 Da to 30,000 Da. In one embodiment $R_4$ is a polyethyleneglycol chain with a molecular weight (Mn) of 10,000 Da to 20,000 Da. In one embodiment $R_4$ is a polyethyleneglycol chain with a molecular weight (Mn) of 15,000 Da to 25,000 Da.

Nanoparticle Hydrodynamic Size

The overall size of the nanoparticle depends on several variables, including core diameter and PEG molecular weight. As used herein, nanoparticle size is defined as measured by Z-average dynamic light scattering (DLS) (defined in ISO 22412:2008).

As an example, in one embodiment, the diameter of the core is 18 nm or greater and a Z-average hydrodynamic diameter of less than 150 nm.

In a further embodiment, the diameter of the core is 23 nm or greater and the molecular weight (Mn) of the PEG portions is 20,000 Da or greater. In such an embodiment the nanoparticles have a Z-average hydrodynamic diameter of less than 250 nm. This size relates to a relatively large core diameter and PEG molecular weight.

Nanoparticle Use

The provided nanoparticles can be used for any applications currently known or developed in the future that utilize magnetic particles. Exemplary methods include MPI, SLNB, and MFH.

In one embodiment the nanoparticles are magnetic tracers configured to be introduced into a subject. In one embodiment the subject is a human. In another embodiment, the subject is a non-human animal. By being configured to be introduced into a subject, the nanoparticles are of sufficient number to possess the required magnetic properties and suspended in a medium compatible with introduction into the subject (e.g., into the subject's bloodstream).

In one embodiment, the nanoparticles have a magnetic moment reversal in serum-containing media (including examples such as fetal bovine serum (FBS), Roswell Park Memorial Institute cell culture+10% fetal bovine serum, whole blood, etc.) that is similar to that in water and other aqueous systems.

In one embodiment, the nanoparticles have a magnetic moment reversal preserved in AC fields with frequency from 1 kHz to 500 kHz.

In one embodiment, the nanoparticles are administered in vivo and their magnetic moment reversal is preserved.

In one embodiment, the inductive signal is preserved in vivo. In one embodiment, the inductive signal is linear with concentration.

In another aspect, methods of using the nanoparticles are provided. In one embodiment, the method comprises applying a magnetic field to a plurality of nanoparticles according to the disclosed embodiments. In certain applications, the magnetic field is applied to a subject into which the nanoparticles have been dispersed.

In one embodiment, the method is a magnetic particle imaging method and the magnetic field comprises a spatially varying magnetic field with a field-free region and a time varying magnetic field. Representative MPI methods with which the nanoparticles are compatible include those disclosed in U.S. Pat. No. 7,778,681 and U.S. Patent Application Publication No. 2011/0089942, the disclosures of which are both incorporated herein by reference in their entirety.

In another embodiment, the method is a magnetic hyperthermia method and the magnetic field is an alternating magnetic field configured to heat the plurality of nanoparticles.

In yet another embodiment, the method is a magnetic sentinel lymph node biopsy method, the method further comprising a step of detecting a magnetic response to the magnetic field.

The specific dimensions of any of the apparatuses, devices, systems, and components thereof, of the present disclosure can be readily varied depending upon the intended application, as will be apparent to those of skill in the art in view of the disclosure herein. Moreover, it is understood that the examples and embodiments described herein are for illustrative purposes only and that various modifications or changes in light thereof may be suggested to persons skilled in the art and are included within the spirit and purview of this application and scope of the appended claims. Numerous different combinations of embodiments described herein are possible, and such combinations are considered part of the present disclosure. In addition, all features discussed in connection with any one embodiment herein can be readily adapted for use in other embodiments herein. The use of different terms or reference numerals for similar features in different embodiments does not necessarily imply differences other than those expressly set forth. Accordingly, the present disclosure is intended to be described solely by reference to the appended claims, and not limited to the preferred embodiments disclosed herein.

The following examples are included for the purpose of illustrating, not limiting, the disclosed embodiments.

EXAMPLES

Example 1

This example demonstrates a method of identifying an optimum size for magnetite nanoparticles that are used to generate MPI signal, where the signal is detected as the third harmonic of nanoparticle magnetization, M, for any driving field frequency, v. The experimental results, for an arbitrarily chosen v=250 kHz, agreed with predictions for a nanoparticle magnetization model based on the Langevin theory of superparamagnetism. By carefully controlling size, it is possible to engineer biocompatible magnetite nanoparticles with optimum physical dimensions that maximize MPI's mass sensitivity. This result is explained using the Langevin theory, is demonstrated experimentally, and provides a basis for synthesizing optimal materials with improved performance relative to commercial options.

Magnetite Nanoparticle Synthesis. Magnetite nanoparticles were synthesized by the pyrolysis of Iron (III) oleate in 1-Octadecene (technical grade, 90%, Aldrich). In a typical reaction to produce 15 nm magnetite nanoparticles, 12 mmol of oleic acid (technical grade, 90% Aldrich) was added to 0.5 mmol of the iron (III) oleate complex dissolved in 2.5 g of 1-Octadecene. After purging under argon for 30 minutes, the mixture was heated, also under argon atmosphere, and refluxed for 24 hours. Finally, the reaction mixture was cooled to room temperature and the nanoparticles were collected and washed in a 1:1 mixture of chloroform and methanol.

To prepare for MPI signal testing, each sample was transferred from the organic to water phase for biocompatibility using the amphiphilic polymer, poly(maleic anhydride-alt-1-octadecene)-poly(ethylene glycol) (PMAO-PEG), and dissolved in 1× Phosphate Buffered Saline (PBS) solution. Following phase transfer, iron concentration was measured using an Inductively Coupled Plasma—Atomic Emission Spectrophotometer (Jarrel Ash 955). The iron concentration in synthesized samples generally ranged from 0.5 to 3.6 mg Fe/mL. The median diameter and size distribution of each was measured by fitting magnetization vs. field data according to the Chantrell method. (Chantrell et al., IEEE Transactions on Magnetics 1978; Mag-14(5):975).

MPI Signal Testing. MPI signal performance was measured using a custom-built transceiver that was specially designed for detecting the 3rd harmonic of nanoparticle magnetization. During its operation sample harmonics are excited using an air-cooled solenoid that is driven at 250 kHz using a commercial radio-frequency (RF) amplifier (Hotek Technologies Model AG1017L). Harmonics are then detected using a smaller receiver coil and counter-windings that both reside coaxially inside. To narrow receiver bandwidth and provide optimal power transfer for harmonic detection, the receiver coil is tuned and matched to 50Ω at 750 kHz. Induced harmonics are also amplified using ~24 dB of gain before detection with a commercial spectrum analyzer (Rohde & Schwarz, Model FSL303).

During testing, the transceiver transmitter coil was driven with 10 Watts of RF power to produce an excitation field of 10 mT$\mu_0^{-1}$. To assess measurement variability, MPI signal testing was performed in triplicate. For each triplicate, 3 small cuvettes were filled with 100 μL of sample at the measured concentration listed in Table 1. Sample cuvettes were then inserted into the transceiver coils.

Langevin Model of Nanoparticle Magnetization. For a sample of nanoparticles, time dependent magnetization M, was modeled as a function of median nanoparticle diameter $d_0$ and standard deviation σ.

$$\frac{M(d_0, \sigma, t)}{M_s} = \int_0^\infty \left( \frac{1}{1+(\omega\tau)^2} + i\frac{(\omega\tau)^2}{1+(\omega\tau)^2} \right) \left( \text{Coth}[ad^3 H(\omega, t)] - \frac{1}{ad^3 H(\omega, t)} \right) g(d_0, \sigma, d) dd, \quad (10)$$

where H($\omega_1$t) is the RF driving field, which varies sinusoidally with amplitude H and angular frequency $$\alpha = \frac{\pi M_3 \mu_0}{6 k_b T},$$

where $M_s$ is the saturation magnetization of the nanoparticles (446 kA/m for magnetite), $\mu_0$ is $4\pi \times 10^{-7}$ Hm$^{-1}$, $k_b$ is the Boltzmann constant, $1.38 \times 10^{-23}$ JK$^{-1}$, and T is the temperature in Kelvin; τ is the effective relaxation time for the particle moment to reverse in an alternating magnetic field, $\tau = \tau_B \tau_N/(\tau_B + \tau_N)$, where $\tau_N$ is the Néel relaxation, $$\tau_N = \frac{\sqrt{\pi}}{2} \tau_0 \frac{\exp[K\rho]}{K\rho^{1/2}}, \quad (11)$$

where K is the magnetocrystalline anisotropy constant, $$\rho = \frac{\pi d^3}{6 k_b T}$$

and $\tau_0$ is taken to be $10^{-10}$ sec, and $\tau_B$ is the Brownian relaxation, $$\tau_B = \frac{3V\eta}{k_b T},$$

where V is the hydrodynamic volume of the particle, and η is the viscosity of the suspending fluid (0.89 mPa s for water). Finally, $g(d_0, \sigma, d)$ represents the distribution of diameters in the sample, and can be well-approximated using a log-normal distribution function:

$$g(d_0, \sigma, d) = \frac{1}{\sigma d \sqrt{2\pi}} \exp \frac{-(\ln(d/d_0))^2}{2\sigma^2}, \quad (12)$$

where σ is the standard deviation of the distribution, and $d_0$ is the median diameter.

Figure 3:
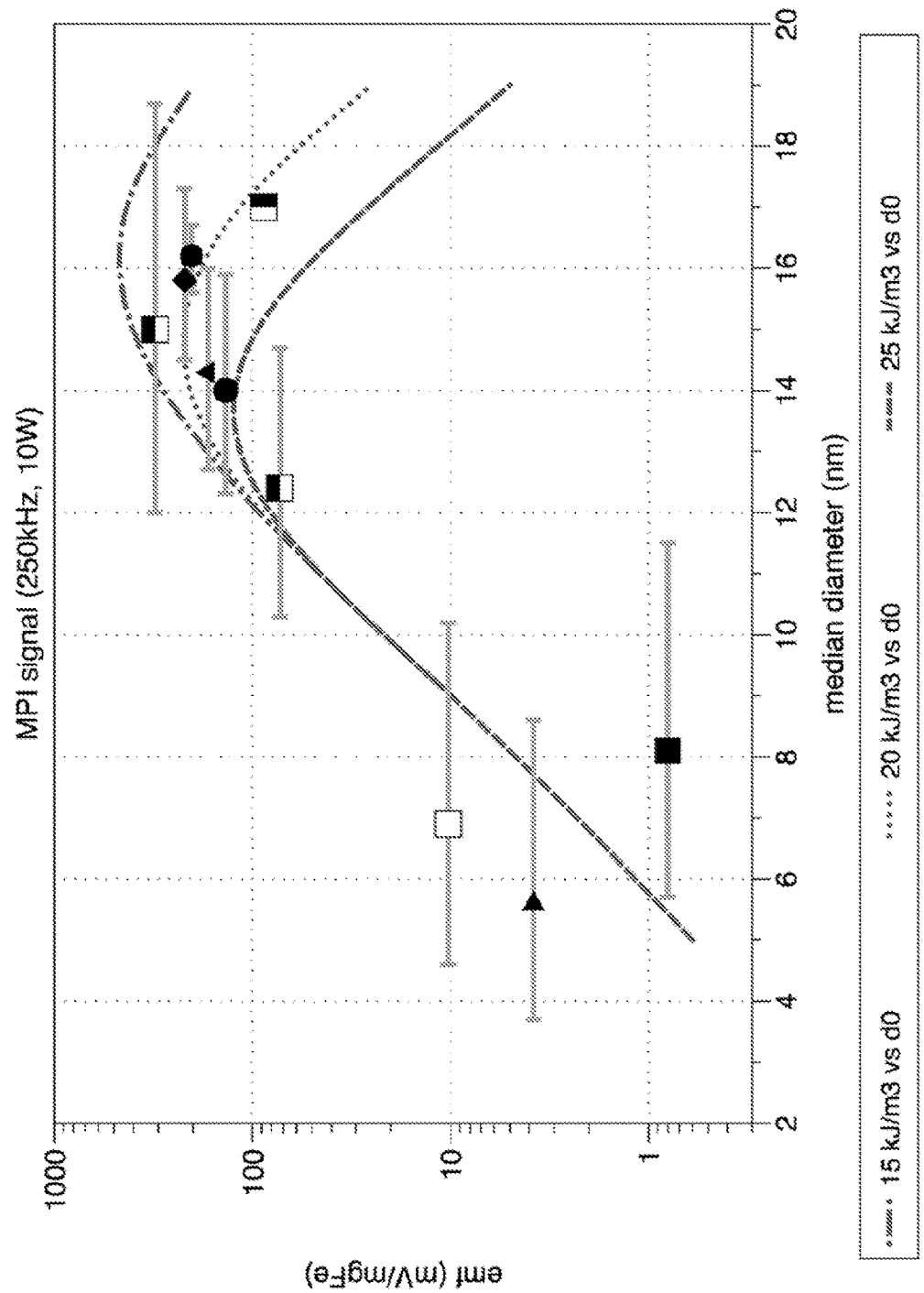
FIG. 3 shows MPI signal testing results, in accordance with an embodiment of the present disclosure. Symbols represent nanoparticle samples. The error bars delineate the first standard deviation of the sample diameter distribution. The curves are simulated data for particles with the listed anisotropy constant from Equation 11 and a log normal distribution with standard deviation 0.1.

By carefully controlling the size of the magnetic nanoparticles, it was demonstrated that MPI signal can vary dramatically with nanoparticle diameter, d. This is illustrated in FIG. 3 where measured signal per mg iron is seen to vary over nearly three orders of magnitude, with some particles exhibiting a 30 fold sensitivity increase over commercial counterparts with comparable iron concentration. There is an observed peak in the harmonic signal vs diameter, indicating that there is an optimum nanoparticle size for MPI at 250 kHz. This optimal size can depend on the drive frequency and the anisotropy constant K (Eq. 11), and can be predicted for other frequencies using the Langevin model discussed above. For 250 kHz MPI, the optimum particle diameter is ~15 nm. Detailed information about the nanoparticle samples shown in FIG. 3 is provided in Table 1. Also included in FIG. 3, are three simulated curves, for Magnetite samples of increasing diameter, having anisotropy constants K of 15, 20, and 25 kJ/m^3, respectively, each with a log-normal size distribution with standard deviation, σ=0.1.

TABLE 1

Details of Magnetite nanoparticle samples used in MPI signal testing.

| Sample | MPI signal (mV/mgFe) | mgFe/ml | D0 (nm) | σ |
|---|---|---|---|---|
| Feridex IV (Bayer) | 10 | 2.21 | 6.9 | 0.40 |
| mf090401 | 4 | 0.24 | 5.6 | 0.42 |
| ak090309 | <1 | 1.68 | 7.5 | 0.28 |
| mf090806 | 72 | 0.68 | 12.4 | 0.18 |
| mf090810p | 136 | 1.56 | 14.0 | 0.12 |
| mf090903p | 168 | 2.72 | 14.3 | 0.17 |
| mf090910p | 310 | 1.10 | 15.0 | 0.22 |
| mf090917p | 221 | 3.64 | 15.8 | 0.09 |
| mf090924p | 204 | 3.12 | 16.3 | 0.07 |
| mf091001p | 88 | 1.73 | 17.0 | n/a |

Maximum signal was produced by sample mf090910p in Table 1. Size for sample mf091001p, which had an open loop at room temperature, was determined by TEM (FEI Tecnai G2 F20), and by the ratio of precursors relative to the other samples. The height and location of the peak in measured signal vs diameter (FIG. 3) quantitatively match the predicted values for magnetite nanoparticles with an anisotropy constant K of ~20 kJ/m^3. Measured values of K for magnetite typically ranged between 23-41 kJ/m^3, while theory predicts 11 kJ/m^3. The decrease in MPI signal for larger particles implies that, though the $10\,mT\mu_0^{-1}$ excitation field is sufficiently large to generate harmonics, it is not large enough to shorten the effective relaxation time t, and instead relaxation is determined by particle size as discussed above. In fact, shortening should only occur at higher applied fields, $H_a$, such that $H_a \gg H_K$, where $H_K = 2K/M_s$ the anisotropy field. The signal voltage per mg iron curve has a 9% average uncertainty, due to errors in the iron concentration and MPI signal voltage measurements.

Example 2

In this example, models described herein in Equations 1-9 above were used for simulations. Magnetite magnetic nanoparticles were synthesized by the pyrolysis of iron (III) oleate in 1-octadecene (technical grade, 90%, Aldrich). Iron (III) oleate was formed in a separate reaction, prior to nanoparticle formation, by dissolving 10 mmol of iron (III) chloride (anhydrous, Aldrich) in 50 ml methanol along with 30 mmol of oleic acid (technical grade, 90%, Aldrich). To this mixture was added, dropwise, 30 mmol of sodium hydroxide dissolved in 100 ml of methanol. The resulting waxy precipitate was washed five times with methanol, dried, dispersed in hexane, and washed five times with water in a separatory funnel. Finally, the product is dried again for storage and later use. In a typical reaction, to produce 15 nm magnetite nanoparticles, 12 mmol of oleic acid (technical grade, 90% Aldrich, St. Louis, Mo.) was added to 0.5 mmol of the iron (III) oleate complex dissolved in 2.5 g of 1-octadecene. After purging under argon for 30 min, the mixture was heated, also under argon atmosphere, and refluxed for 24 h. Finally, the reaction mixture was cooled to room temperature and the nanoparticles were collected and washed thoroughly in a 1:1 mixture of chloroform and methanol.

For phase transfer, a synthetic route was chosen based on organic solvents and surfactants because it leads to highly crystalline magnetic nanoparticles with narrow size distributions (typical σ of 0.1, corresponding to a 95% confidence interval of ±~2 nm) and controllable size. However, since organic solvents are not suitable for use in biological imaging, the as-synthesized magnetic nanoparticles were transferred to the water phase. To ensure biocompatibility, organic residue was removed and the final magnetic nanoparticles were stable and not cytotoxic. The amphiphilic polymer poly(maleic anhydride-alt-1-octadecene)-poly(ethylene glycol) (PMAO-PEG) was used to affect phase transfer and dissolve the final magnetic nanoparticles in 1× phosphate buffered saline solution for testing.

For characterization, as-synthesized samples were dispersed on carbon TEM grids by a controlled evaporation of the solvent. Bright field images were then obtained using a FEI Tecnai TEM (Hillsboro, Oreg.) equipped with a Gatan CCD camera (Pleasanton, Calif.), operating at 200 KeV. Following phase transfer to aqueous solution, iron concentration was measured with an inductively coupled plasma-atomic emission spectrophotometer (Jarrel Ash 955). The iron concentration in synthesized samples ranged from 0.5 to 3.6 mgFe ml$^{-1}$. Magnetization vs field data M(H) was acquired with a LakeShore (Weterville, Ohio) vibrating sample magnetometer at room temperature. Sample UW170_16 showed a slight open loop at room temperature and for this sample, M(H) data were acquired above the blocking temperature at 575 K using a Quantum Design (San Diego, Calif.) PPMS VSM oven. Saturation magnetization $M_s$ (kA m$^{-1}$) was determined from M(H) data and the measured sample concentration by assuming density equal to stoichiometric magnetite (5180 kg m$^{-3}$). The median diameter and diameter distribution of each sample were determined from M(H) data according to the Chantrell method.

Figure 4:
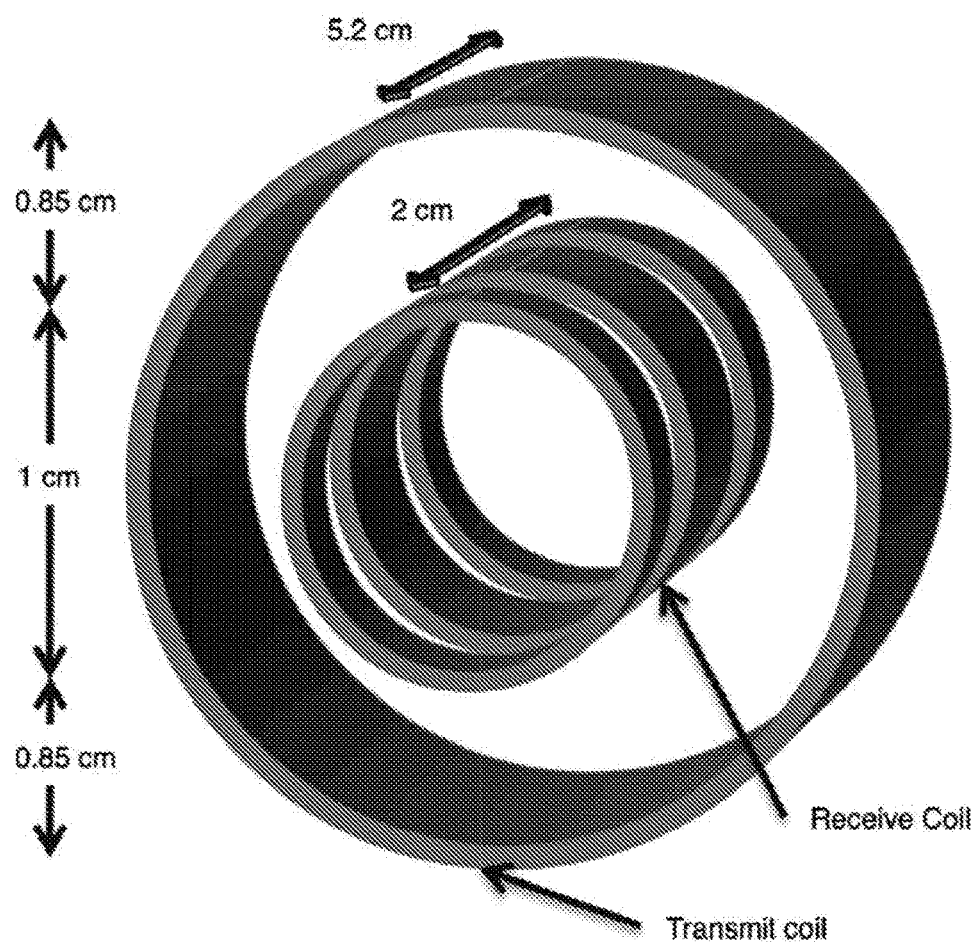
FIG. 4 is a schematic diagram of MPI transceiver coils, in accordance with an embodiment of the present disclosure.

MPI signal was measured using a custom-built narrowband transceiver designed to detect the third harmonic of magnetic nanoparticle magnetization. FIG. 4 shows a schematic diagram of transmit and receive coil arrangement in the MPI transceiver. During transceiver operation, an air-cooled, wirewound solenoid transmit coil excites sample harmonics that are then detected by a receiver coil. The transmit coil consists of 94 turns of 550 μm diameter copper wire and has a diameter and a length of 2.71 and 5.2 cm, respectively. The receiver coil is positioned inside the transmit coil and contains 140 total turns of 114 μm diameter copper wire. The receiver coil is designed to inductively isolate receive and transmit channels. It features three coaxial solenoids connected in series: Two outer coils each with 35 counterwound turns are positioned on either side of a central solenoid with 70 turns. The entire receiver coil has a diameter of 1 cm and a total length of 2 cm, with 3 mm spacing between the central and outer windings. During operation, the outer windings inductively decouple the receiver from the transmitter to reduce the level of harmonic noise that is detected. Additional use of radio-frequency (RF) traps and capacitive decoupling increases electrical isolation between the transmitter and receiver to well over 120 dB. The transmit coil was driven at 250 kHz by a commercial RF amplifier (Hotek Technologies, Tacoma, Wash., Model AG1017L). To narrow receiver bandwidth and provide optimal power transfer for harmonic detection, the receiver coil was tuned and matched to 50 at 750 kHz. Induced harmonics were also amplified using ~24 dB of gain before detection with a commercial spectrum analyzer (Rohde & Schwarz, Munich, Germany, Model FSL303).

During testing, the transmitter coil was driven with 10 W of RF power to produce a sinusoidal excitation field with amplitude $H_0$~6 mTμo$^{-1}$. To assess measurement variability, MPI signal testing was performed in triplicate. For each sample, three cuvettes were filled with 100 μl of sample, at the measured concentration listed in Table 2. Sample cuvettes were then inserted into the transceiver coils and the signal was recorded. The normalized signal listed in Table 2 is the average of the three tested samples.

Numerical Simulations. MPI signal was simulated using MATHEMATICA software according to the models described herein. M(t) data were generated at a sampling rate of 4 MHz, sufficient to resolve the MPI signal at 750 kHz, by numerical integration of Eq. (2). The integration was limited to physically relevant diameters in order to reduce computing time. For each distribution, the integration bounds were chosen such that g(d) [Eq. (6)]>0.01 at the boundary d values. For all fields $H_0$ up to saturation, this condition yielded the same precision in M(t) to at least four significant figures, as setting the bounds from ~0 to 1000 nm. The step size was chosen to ensure similar accuracy in M(t) at a range of fields up to saturation. The MPI signal was defined to be the emf induced in a receive coil by M3, the third harmonic of M(t), determined by discrete Fourier transform of M(t). According to the theory of reciprocity, this can be related to the axial field $B_{axial}$ (TA$^{-1}$), produced by unit current in the receive coil $$emf_v = 6\pi f_o M_3 B_{axial} \qquad (13)$$

where $f_0$ is the driving field frequency.

MPI signal is plotted against the measured median diameter do in FIG. 5A and characteristics of the measured MNP samples are provided in Table 2. All data have been normalized by iron concentration to allow comparison between samples. The signal voltage per mg iron has 12% average uncertainty due to errors in the iron concentration and MPI signal voltage measurements. The error bars are smaller than the dot size in FIG. 5A. Size-dependent signal generation can be seen in the figure, with a maximum value for sample UW150_22 (median diameter equal to 15 nm).

TABLE 2

Properties of magnetite nanoparticles used in MPI signal testing.

| Sample | MPI signal (mV/mgFe) | mgFe/ml | $M_s$ (kA/m) | $d_0$ (nm) | σ |
|---|---|---|---|---|---|
| Feridex IV | 10 | 2.21 | 223 | 6.9 | 0.40 |
| UW056_42 | 3 | 0.24 | 225 | 5.6 | 0.42 |
| UW075_28 | 1 | 1.68 | 155 | 7.5 | 0.28 |
| UW124_18 | 72 | 0.68 | 322 | 12.4 | 0.18 |
| UW140_12 | 136 | 1.56 | 384 | 14.0 | 0.12 |
| UW143_17 | 163 | 2.72 | 203 | 14.3 | 0.17 |
| UW150_22 | 291 | 1.17 | 347 | 15.0 | 0.22 |
| UW158_09 | 233 | 3.45 | 293 | 15.8 | 0.09 |
| UW163_07 | 216 | 2.94 | 300 | 16.3 | 0.07 |
| UW170_16 | 91 | 1.66 | 309 | 17.0 | 0.16 |

FIG. 5B shows simulated data for each experimental sample. Normalized MPI signal voltage was calculated per mg iron, assuming stochiometric magnetite of density 5180 kg m$^{-3}$. Measured values of $d_0$, σ, and $M_s$ were used as listed in Table 2; was assumed to be the bulk value (11 kJ m$^{-3}$), $f_0$ was 250 kHz, and $H_0$ was 6 mT $\mu_0^{-1}$. Values of $M_s$ listed in Table 2 have 20% average uncertainty due mainly to error in the sample volume used to measure M(H). The hydrodynamic diameter dH=d+2δ was used to determine the Brownian component of the effective relaxation time τ [Eq. (6)], where δ is the thickness of the polymer layer surrounding the magnetic core; in all simulations, δ was 10 nm, the length of the PMAO-PEG layer as measured by dynamic light scattering of MNPs before and after phase transfer.

FIG. 6 shows simulated data for magnetite MNPs to illustrate how changes in the anisotropy, the standard deviation of the diameter distribution σ, and the driving field amplitude Ho affect the signal voltage as a function of MNP size. In FIG. 6A, the range of K values is the expected range for magnetite nanoparticles, from the bulk value 11 kJ m$^{-3}$ to a larger value 20 kJ m$^{-3}$ that is in the middle of the range of values previously observed for particles smaller than 20 nm diameter.

By controlling MNP synthesis to produce a series of samples with closely spaced diameters and narrow size distributions, it has been demonstrated that MPI signal varies dramatically with MNP diameter, as predicted by models described herein. The observed normalized MPI signal is seen to vary over three orders of magnitude in the measured samples, with some particles exhibiting a 30-fold sensitivity increase over commercial counterparts with comparable iron concentration.

Our experimental device was designed to test the feasibility of generating harmonics for MPI imaging of small volumes, suitable for small animals. The driving field frequency, $f_0$=250 kHz throughout this work, was chosen accordingly. The field strength used in experiment (6 πτTμo$^{-1}$) was chosen to limit coil heating, while the simulated fields in FIG. 6C were also chosen as relevant for imaging small animals at 250 kHz, where 12 mTμ$_0^{-3}$ is estimated to be the magnetic simulation threshold.

A feature of FIG. 5 is the observed peak in harmonic signal as a function of MNP diameter. This peak shows an optimum MNP size for MPI at 250 kHz. Comparing experimental data with the simulated data of FIG. 4B, we see quantitative agreement to within a factor of 2 for most samples. The exceptions include the two smallest samples, UW056_42 and Feridex I.V.™, which also feature the largest a; sample UW143_17, which has an unusually low measured Ms relative to its neighbors; and UW170_16, the largest sample. Modeling samples UW056_42 and Feridex was less reliable due to small median diameters and very broad distributions. Their measured distribution functions g(d) each include diameters as small as 1 nm, which is of the order of a single unit cell for magnetite.

In the simulated points of FIG. 5B, the signal voltage increases with diameter up to 15 nm, corresponding to the experimental data. However, a peak diameter is not clearly visible. In fact, given our assumption that K is equal to the bulk value (11 kJ m$^{-3}$), samples up to at least 20 nm in diameter may be needed to clearly resolve the peak (shown in FIG. 5A). Experimental data showed a peak near 15 nm, from which may infer that the MNPs have anisotropy greater than 11 kJ m$^{-3}$. For K=20 kJ m$^{-3}$, the simulated data of FIG. 6A showed a peak at 15 nm. This is consistent with theoretical studies showing that nanoparticles can have an effective anisotropy greater than the bulk due to broken symmetry at their surfaces.

The same effects that yield increased K lead to a reduction in Ms with decreasing MNP size. This trend was observed in the samples: The average measured Ms is 70% (308 kA m$^{-1}$) of the bulk (446) value for magnetite for the samples with $d_0$ 10 nm; it is 45% (201) for samples with $d_0$<10 nm. The maximum concentration of 3.65 mgFe/ml (0.065 molFe/l) is quite low and it is unlikely that the small variations in sample concentrations contributed to the observed differences in MPI signal. The simulated results in FIGS. 6A-C provide insight into how the MPI signal strength will vary with sample properties and the driving field amplitude $H_0$. More generally, the model used herein and simulated results provide a physical understanding of the peak observed in the experiments. The decrease in MPI signal for MNPs larger than 15 nm in diameter is due to increased relaxation time τ. In small particles less than ~10 nm in diameter, magnetic relaxation is dominated by the Néel process wherein the moment is thermally activated and typically reverses in nanoseconds. Brownian relaxation dominates in large particles greater than ~20 nm in diameter. The moment of such particles is blocked or fixed along an easy axis, so that the entire particle physically rotates to align with an external field. The Brownian relaxation constant varies linearly with hydrodynamic volume and is substantially slower than Néel relaxation, its period ranging from microseconds to milliseconds depending on the thickness of the hydrodynamic layer that is made up of the surface coating(s) on the nanoparticles. Because the Néel relaxation time N [Eq. (7)] depends exponentially on the magnetic volume, relaxation slows with increasing diameter in the region between 10 and 20 nm for magnetite. If the effective relaxation time τ is longer than the period of the driving field, one would expect the MNP moment to lag behind the driving field, the in-phase component of susceptibility to decrease, and the out-of-phase component to become more prominent. For the simulated data of FIGS. 6A-C, this transition corresponds to descent from the peak in MPI signal to the shoulder as the diameter increases. We note that the peak height varies with, but the height of the shoulder, where relaxation is Brownian, does not. As expected, larger $H_0$ yield increased harmonic amplitude, especially for intermediate sizes where Néel relaxation dominates. The peak signal is seen to shift to slightly smaller diameters with increasing field.

The experimental data show that a detectable third harmonic can be produced by fields as small as 6 mT $\mu_0^{-1}$ Furthermore, the measured decrease in MPI signal for larger sized MNPs implies that the 6 mT $\mu_0^{-1}$ excitation field generated by our MPI transceiver during these experiments is not large enough to shorten the effective relaxation time τ. Therefore, the finite relaxation time should be considered as in Equations 1-9. We can estimate the field at which shortening is expected to occur; this should be when $H_a \gg H_K$, where $H_a$ is the applied field and $H_K$ is the anisotropy field. For bulk magnetite, which has cubic symmetry, $H_K = 4K/(3\mu_0 M_s) = 34$ mT $\mu_0^{-1}$.

It has been shown with experiments that magnetite MNPs chosen for their optimized magnetic properties can show 30-fold improvement in normalized MPI signal over commercial samples, where the frequency of the driving field $f_0$ is 250 kHz and the MPI signal is measured at $3f_0$. We have also observed a peak in MPI signal as a function of MNP size, with the diameter of ~15 nm. A model of MNP magnetization based on the Langevin theory predicts a similar peak and gives some physical understanding of the underlying cause: The transition between Néel and Brownian relaxation results in a reduction in the MPI signal. Wherever the effective magnetic relaxation time τ of some samples under test approaches $\frac{1}{2}\pi f_0$ in magnitude, there should be an optimum MNP size.

Example 3

In this example, it is shown that monodispersed MNPs ($Fe_3O_4$), synthesized in organic solvents and successfully transferred to water, can be tailored for strong size-dependent heating for any chosen combination of field frequency and amplitude. In order to establish biological relevance, heating rates were also measured in cell culture medium and the results interpreted in terms of changes in Brownian relaxation due to particle agglomeration.

Nanoparticles were synthesized according to a procedure based on pyrolysis of metal fatty acid salts; in this case, $Fe^{3+}$-oleate. $Fe^{3+}$-oleate was prepared and stored as a stock solution (conc. 18 wt. %) in 1-octadecene (ODE, technical grade 90%). $Fe_3O_4$ nanoparticles of desired sizes were synthesized by reacting predetermined amounts of $Fe^{3+}$-oleate and oleic acid (tech. 90%) in ODE. For instance, synthesis of 15 nm particles used 0.2 mmol/g of $Fe^{3+}$-oleate and 3 mmol/g of oleic acid in 2.5 g of reaction solvent (ODE). The mixture was refluxed overnight (~24 h) at 320° C. under argon and vigorous stirring. The final product was collected and washed four times with a 1:1 (v/v) mixture of chloroform and methanol to remove excess surfactant and solvent. MNP powder, obtained by drying in vacuum for 30 min, was hydrophobic and easily dispersed in organic solvents such as toluene or chloroform. Phase transfer to aqueous phase was achieved by coating oleic acid coated MNPs (MNP@OA) with poly(maleic anhydride-alt-1-octadecene)-poly(ethylene glycol) (PMAO-PEG), an amphiphilic polymer. Colloidal stability of PMAO-PEG coated MNPs (MNP@PMAO-PEG) was characterized using Dynamic Light Scattering (DLS—Zetasizer Nano, Malvern Instruments). Iron concentration was determined using an inductively coupled plasma atomic emission spectrophotometer (ICP-AES, Jarrell Ash 955). A room temperature vibrating sample magnetometer (VSM, Lakeshore) was used to obtain magnetization results.

Heating rates of MNPs in water and tissue culture medium (Dulbecco's modified Eagle medium with 10% fetal bovine serum, DMEMk 10% FBS) was measured using a dedicated hyperthermia system (magneTherm, nanoTherics, UK). Alternating magnetic field (AMF) frequency and amplitude were set at 376 kHz and 13.5 kA/m, respectively. A fiber optic thermocouple (Luxtron, Lumasense Technologies) was used to probe temperature. The power dissipation or SLP was measured using the following equation:

$$SLP(\text{watts}/gFe_3O_4) = c\frac{m_{H_2O+Fe_3O_4}}{m_{Fe_3O_4}}\left(\frac{dT}{dt}\right). \quad (14)$$

where c is the specific heat capacity of water (4.186 J/g ° C.), $m_{Fe_3O_4}$ and $M_{H_2O+Fe_3O_4}$ are the mass of $Fe_3O_4$ and mass of whole sample in grams, respectively, and dT/dt is the temperature ramp rate in ° C./sec.

Transmission electron microscopy (TEM) imaging (FIG. 7A) shows that MNPs synthesized via the organic route are monodispersed (diameter of 16±1 nm is shown). For superparamagnetic particles, size and the lognormal size distributions were also determined by fitting magnetization curves to the Langevin function. Magnetization curves of MNP@PMAO-PEG in DI water for a range of sizes show increase in initial susceptibility and saturation with increasing particle size (FIG. 7B). Depending on the particle size, saturation magnetization values reach up to 80% of the bulk saturation value of magnetite, i.e., 90 emu/g. Due to spin disordering at the surface, saturation values of magnetite nanoparticles are often less than bulk values. Magnetization measurements before (MNP@OA) and after (MNP@PMAO-PEG) phase transfer show negligible change in the magnetic properties (FIG. 7C). Finally, magnetic properties are consistent over the tested time period (5 months), suggesting excellent shelf life of MNP @ PMAO-PEG.

Heating rates measured as a function of MNP size show a sharp peak in SLP at a diameter of 16 nm for $\sigma_{avg}=0.175$ (FIG. 8A). SLP values were calculated using equation (14). When particles of broader average size distribution ($\sigma_{avg}$=0.266) were used, the peak SLP value dropped from 144 to 100 W/g $Fe_3O_4$ (30% drop). These results confirm that a small increase in polydispersity can be negatively affect the heating capacity of MNPs.

In order to simulate biologically relevant environment, heating rates of MNPs dispersed in (DMEM with 10% FBS and 1% L-glutamine) were measured. FIG. 8B shows that MNPs of sizes 13 and 14 nm do not show any significant changes in SLP; however, 16 nm MNPs show a 30% decrease. DLS measurements FIG. 8C show that hydrodynamic size of MNP@PMAO-PEG increase when dispersed in DMEM+10% FBS. According to the magnetization relaxation theory of superparamagnetic nanoparticles, increase in hydrodynamic volume prolongs Brownian relaxation while the relaxation via Neél mechanism is unaffected. Furthermore, models show that, in water, 16 nm MNPs lie within the transition region from Neél to Brownian relaxation. Thus, based on our results, we infer that ~30% of MNPs in the 16 nm sample were large enough to undergo Brownian relaxation and due to agglomeration in DMEM, the Brownian relaxation is blocked or too slow relative to the 376 kHz time window imposed by the AMF. The 13 and 14 nm samples did not show any significant change in SLP, even though they also agglomerated in DMEM (data not shown), suggesting primarily Neél relaxation. These measurements give significant insight into biological implications of hyperthermia. Even if MNPs are delivered in sufficient concentrations to target sites, adherence to cells and biomolecules is inevitable in in vivo situations and should be taken into consideration.

Example 4

Background

Since the idea of site-specific therapy is to restrict treatment to the cancer site, thereby minimizing side effects and patient discomfort, magnetic nanoparticles (MNPs) are an attractive option because they can be remotely targeted by application of external magnetic field gradients or other active and passive targeting methods. Once localized, Magnetic Fluid Hyperthermia (MFH), a therapeutic modality that utilizes alternating magnetic fields (AMF) to dissipate heat from the resulting relaxation losses in MNPs, can be used to induce localized heating. Heating cancer cells (typically to ~42-43° C.) is known to disrupt cellular metabolism making adjuvant therapy by conventional established methods more efficient. A wide range of ferromagnetic nanoparticles, with superior magnetic properties, can be synthesized for MFH. However, iron oxide ($\gamma$-$Fe_2O_3$ or $Fe_3O_4$) magnetic nanoparticles show minimal toxicity and are FDA approved for MRI contrast agents and more recently for treatment of patients with chronic kidney disease. Furthermore, due to their modest magnetic characteristics when compared to the ferromagnetic elements, it is desired to optimize their morphological (size, size distribution, shape), crystallographic (phase purity) and magnetic (relaxation) characteristics for effective application in MFH.

MFH has been studied on both in vitro and in vivo platforms. However, the difficulty in delivering a sufficient amount of MNPs at the target site in order to promote a noticeable therapeutic outcome is one of the major hurdles impeding clinical adoption of MFH. For example, an estimated 32 mW of power dissipation for a treatment time of 10 minutes is used to raise the temperature of 1 g of prostate tumor tissue ($c_P$~3.8 kJ $kg^{-1}$ $s^{-1}$) by 5° C. This is an underestimation and can be higher if cooling from blood perfusion is taken into account. Nevertheless, based on this rough estimate, a minimum dose of 0.32 mg of magnetic nanoparticles that have a Specific Loss Power (SLP) of 100 W/g, per gram of tumor tissue would be needed to locally raise the temperature by 5° C.

SLP output can be optimized if the effective magnetization relaxation time of MNPs match the applied AMF frequency. The effective relaxation time depends on both Neél (magnetization reversal) and Brownian (particle rotation) time components. Brownian relaxation ($\tau_B$) depends linearly on the fluid viscosity ($\eta$) and the hydrodynamic particle volume ($V_H$), and is typically difficult to control due to the dynamic nature of the in vivo environment. It can also be detrimental to SLP output if the hydrodynamic volume is found to increase significantly. On the other hand, the operating Neél relaxation time ($\tau_N$) depends exponentially on the product of magnetic anisotropy constant (K) and the magnetic core volume ($V_m$) $\tau_N$~exp (KV). Due to this exponential dependence, even slight increase in the size distribution alters the effective relaxation time. It is clear from the above discussion that the effective relaxation time, whether dominated by Neél or Brownian component, is dependent on the particle volume. Thus, it is desired to tailor particle size and, more importantly, the size distribution for a chosen AMF frequency, and also ensure MNPs do not agglomerate in biological medium in order to maximize SLP output. For instance, according to a model based on the known size-dependence of magnetic relaxation in MNPs, if size distribution increases from highly monodisperse ($\sigma$=0) to polydisperse ($\sigma$=0.25), heating rate degrades by a factor of 5. This changes the estimate above, which assumes ideally monodisperse MNPs, to ~1.6 mg of polydisperse MNPs ($\sigma$=0.25) per gram of tumor tissue or 5 times more than needed.

Current MNP synthesis methods typically involve co-precipitation of iron salts in aqueous solution and lack the ability to produce monodisperse MNPs. So far, most studies of MFH utilize MNPs synthesized by such methods, and rely primarily on "extrinsic" augmentations in order to counteract the ineffectiveness of polydisperse MNP dispersions and improve therapeutic efficiency. Such augmentations include, directly injecting tumors with large quantities of MNPs or planting "thermoseeds" at tumor sites. However, in most cases the exact tumor location may be either unknown or require invasive methods to be reached. Increasing the administered MNP dose is also limited by the maximum tolerated dose (MTD); alternatively, increasing the applied magnetic field amplitude is also not an option as it can result in non-specific eddy current heating of surrounding tissue. Thus, an approach to optimize MFH is to intrinsically tailor the MNPs, which are the actual source of heating.

In order to tailor MNPs for optimized MFH response, highly monodisperse magnetite ($Fe_3O_4$) MNPs have been synthesized using organic methods and have been subsequently transferred to aqueous phase using a biocompatible amphiphilic polymer. The organic synthesis route gives control over size, size distribution, shape and phase purity, enabling synthesis of MNPs specifically tailored for any chosen AMF frequency. The resulting power output, or SLP, is maximum and optimized for that specific frequency. Systematic characterization was done to confirm that the synthesized MNPs possess the necessary characteristics for optimum MFH performance. A dedicated hyperthermia system was used to measure heating capacity of MNPs and identify the optimum size for our chosen AMF conditions (f=373 kHz, $H_0$=14 kA/m). Finally, the in vitro therapeutic effectiveness was compared for monodisperse MNPs to induce hyperthermia in cells as a function of concentration and size.

Materials and Methods

Chemicals Iron (III) Chloride, anhydrous (98%) was purchased from Alfa-Aesar. Oleic acid (tech. grade, 90%), 1-octadecene (tech. grade 90%), poly(maleic anhydride-alt-1-octadecene) ($M_n$=30,000-50,000), Pluronic®-F127 ($M_n$=12,600), methoxy polyethylene glycol) ($M_n$=5,000) and ethylene diamine were purchased from Sigma-Aldrich. 1-Ethyl-3-[3-dimethylaminopropyl]carbodiimide hydrochloride was purchased from Pierce Biotechnology. N-Succinimidyl 3-(2-pyridyldithio)propionate (99+%) was purchased from Molecular Biosciences.

Synthesis of $Fe_3O_4$ magnetic nanoparticles (MNPs). Magnetite MNPs were synthesized according to a procedure based on pyrolysis of metal fatty acid salts; specifically, $Fe^{3+}$-oleate. $Fe^{3+}$-oleate was prepared according to previous methods and stored as a stock solution (conc. 18 wt %) in 1-octadecene (ODE, technical grade 90%). A method was developed that allows reproducible synthesis of highly monodisperse $Fe_3O_4$ nanoparticles of diameters ranging from 10-25 nm by reacting pre-defined amounts of $Fe^{3+}$-oleate and oleic acid (tech. 90%) in ODE. For instance, synthesis of 15 nm particles used 0.2 mmol/g of $Fe^{3+}$-oleate and 3 mmol/g of oleic acid in 2.5 g of reaction solvent (ODE). The mixture was refluxed overnight (≥24 hours) at 320° C. under a blanket and vigorous stirring. Nucleation of nanoparticles was observed as a sudden change in color, from clear to black. The final product was collected and washed to remove excess surfactant and solvent. MNPs were precipitated using an excess of 1:1 (v/v) mixture of chloroform and methanol; they were then separated using a magnet and the washing step was repeated at least four times. MNP powder, obtained by drying in vacuum for 30 minutes, was coated with oleic acid and could be easily dispersed in organic solvents such as toluene or chloroform. X-ray diffraction (XRD—Rigaku) was used to confirm the crystalline phase of $Fe_3O_4$ and determine size of nanocrystals. A Vibrating Sample Magnetometer (VSM—Lakeshore) was used to measure magnetic properties of the samples.

Synthesis of PMAO-PEG. Methoxy-poly(ethylene glycol) (m-PEG, $M_n$=5,000) was used in the PEG-ylation of PMAO ($M_n$=30,000-50,000). PEG is considered highly biocompatible as it rejects non-specific protein adsorption, is non-immunogenic and nontoxic. Under acid catalysis, the hydroxyl group on m-PEG forms an ester bond with the anhydride ring on PMAO. In a typical reaction 2 g of PMAO (≈50 μmol) was reacted with 3.75 g of m-PEG (≈750 μmol) in 20 ml of acetone. A few drops of concentrated sulfuric acid were added to catalyze the reaction. The mixture was refluxed at 58° C. in an argon atmosphere. After 24 hours, the mixture was cooled to room temperature and the polymer was obtained by precipitation in excess DI water. After several more DI water washes by sonication and centrifugation, the white polymer cake was freeze dried for 24 hours. The final product was obtained as a white powder and stored at room temperature. Gel Permeation Chromatography (GPC) was used to confirm the increase in molecular weight after PEG-ylation (data not shown).

Phase transfer of hydrophobic MNP using PMAO-PEG. In a typical phase transfer process, about 10 mg of oleic acid coated MNP (MNP@OA) and 10 mg of PMAO-PEG were dissolved in 1-2 ml of chloroform. The mixture was sonicated in an ultrasonic bath for about 15 minutes and dried under a stream of argon. The dried nanoparticle-polymer complex was dispersed in 1 ml of 1× Tris-acetate-EDTA (TAE) buffer by a 30-minute sonication step. MNP coated PMAO-PEG (MNP@PMAO-PEG) were filtered using a 0.45 μm nylon syringe filter. In order to remove excess unbound polymer, MNP@PMAO-PEG were passed through a Sephacryl™ S-200 HR gel column (GE Healthcare Life Sciences). Either de-ionized (DI) water or 1× phosphate buffered saline (PBS) was used as the eluent. Nanoparticles were stored at 4° C. until further use. Iron concentration was determined using an Inductively Couple Plasma Atomic Emission Spectrophotometer (ICP-AES, Jarrell Ash 955).

Colloidal stability measurements. In order to understand the colloidal properties of MNP@PMAO-PEG, zeta potential and hydrodynamic size measurements were done using dynamic light scattering (DLS) technique (Zetasizer Nano, Malvern Instruments). For biological relevance, hydrodynamic size measurements were also made in cell culture medium.

Cytotoxicity study. Jurkat cells (human T-cell leukemia cell line) were grown in RPMI 1640 medium+10% fetal bovine serum (FBS) in physiological conditions (37° C. and 5% $CO_2$). Complementary assays were conducted to confirm there is reasonable correlation between cell viability and induced toxicity. A Lactate Dehydrogenase (LDH) assay (Cytotox-ONE®, Promega) was used to determine MNP toxicity to cells by measuring LDH release in medium due to membrane disintegration. Cell viability was determined using a luciferase assay (Celltiter-GLO®, Promega), which measures ATP levels. Cells were seeded at 20,000 cells/well in a 96-well plate. MNP concentrations of 150 μgFe/ml, 300 μgFe/ml and 450 μgFe/ml were tested for 24 hours in physiological conditions. Appropriate controls were included to ensure assay validity and test for any interference MNPs or media may have with the assay. A microplate reader was used to measure fluorescence at $\lambda_{ex}$=560 nm and $\lambda_{em}$=590 nm for LDH assay, and a luminometer (TopCount, Perkin-Elmer) was used for measuring luminescence in the luciferase assay.

In vitro hyperthermia. An alternating magnetic field (AMF) of frequency, f=373 kHz, and amplitude, $H_0$=14 kA/m, was generated using a dedicated commercial hyperthermia system (magneTherm™, NanoTherics Limited, UK). Jurkat cells were cultured in triplicates at a density of 10,000 cells/well. MNPs of three sizes (12, 13 and 16 nm) with varying concentrations were added to the cultured cells. Prior to AMF heating, samples and controls were incubated at 37° C. for 15 minutes to stabilize temperature. Samples were enclosed in a thermally insulating Styrofoam™ jacket before inserting in the instrument's coil assembly. After 15 minutes of AMF application, samples were returned to the 37° C. incubator. Cell viabilities were compared using the Celltiter-GLO® luciferase assay.

Results

Characterization of $Fe_3O_4$ MNPs. Synthesized MNPs were highly monodisperse as characterized by TEM imaging. Hydrodynamic size of MNPs, before and after coating with PMAO-PEG, was measured using Dynamic Light Scattering (DLS). Magnetization curves, M(H), from VSM measurements were fit to the Langevin function, to obtain median magnetic core size and the volume-weighted size-distribution, using the Chantrell method. Average diameters and corresponding standard deviations, assuming a lognormal distribution, are shown in Table 3. Magnetic properties were reconfirmed after organic to aqueous phase transfer; example of a 12 nm sample, before, after and 5 months after coating.

TABLE 3

Median diameters and standard deviations of as-synthesized MNPs, derived from Chantrell fitting of magnetization curves.

| Size (nm) | Std. Dev (σ) |
|---|---|
| 12 | 0.01 |
| 13 | 0.1 |
| 14 | 0.23 |
| 16 | 0.16 |
| 18 | 0.34 |

Powder X-ray diffraction θ-2θ scans of as synthesized MNPs are shown in FIG. 9. The scans show a good match with the powder diffraction file (PDF) for magnetite (#019-0629, International Centre for Diffraction Data). As indicated in the FIGURE, scans for MNPs of two sizes are included (top and middle). Since smaller particles (<15 nm) are nearly spherical in shape (TEM data not shown), a modified version of Scherrer's formula accounting for the spherical geometry was used to determine crystal size of smaller particles (top spectrum). The generalized form was used for larger MNPs (middle scan) due to their noticeable non-spherical geometry characterized by faceting. The peak at 35.42° (θ=17.71°) was chosen for all crystallite size calculations. The calculated crystal sizes are 13.7 nm and 16.9 nm for the top and middle scans, respectively. These are in good agreement with the corresponding magnetic diameters determined by the Chantrell fitting method, which are 12.9 nm and 15.9 nm, respectively.

Colloidal stability. MNPs preferentially disperse in the aqueous phase after coating with PMAO-PEG (FIG. 10(A)) and show no signs of physical agglomeration or aggregate formation for several months. Long-term colloidal stability of MNPs in water was determined by measuring zeta potential as a function of pH (FIG. 10(B)). MNPs display a neutral surface charge across a wide range of pH values (2-12). Additionally, for biological relevance, hydrodynamic size measurements were also done in cell culture medium (RPMI 1640+10% FBS) to ensure MNPs remain stable during in vitro experiments (FIG. 10(C)). MNPs show no significant change in hydrodynamic size up to a period of 96 hours of incubation in RPMI 1640 medium.

Cytotoxicity. FIG. 11 shows results of MNP@PMAO-PEG cytotoxicity in Jurkat cells. Complementary viability (Luciferase assay) and toxicity (LDH release assay) studies were done to confirm validity of the performed assays. Cell viability drops to about 75% for the lowest concentration tested (150 μgFe/ml), while similar levels, within the calculated errors, are maintained for higher concentrations (300 and 450 μgFe/ml). The trend observed in the toxicity measurement agrees reasonably well with that observed in the viability measurement. Additionally, bright field images of cells incubated with MNPs were captured to examine any subsequent morphological alterations (FIG. 12A-H). Jurkat cells are suspension cells and do not adhere to culture plates, as indicated by their spherical shape (FIGS. 12 (A&E)). The cellular structure and shape is consistent with the control (no MNPs) for all concentrations of MNPs (FIGS. 12 (B-D) & (F-H)).

Magnetic Fluid Hyperthermia. MNPs of various sizes (Table 3) were tested for specific loss power (SLP, watts/g) in a dedicated hyperthermia system. The AMF frequency and amplitude were set at 373 kHz and 14 kA/m respectively. A fiber-optic thermocouple (Luxtron, Lumasense Technologies) was used to measure the temperature ramp rate (dT/dt) in samples. SLP was measured using the following equation:

$$SLP(\text{watts}/gFe_3O_4) = c \frac{mass_{Sample}}{mass_{Fe\rho_s}} \left(\frac{dT}{dt}\right) \quad (15)$$

where c is the specific heat capacity of water (4.187 J g$^{-1}$ °C.$^{-1}$). Two sets of samples with average standard deviations (σ) of 0.175 and 0.266 were measured to specifically characterize effects of both size and size distribution on the power output. Such characterization is intended to emphasize the significance of tailoring size to a specific frequency, thus intrinsically optimizing MFH from a material perspective rather than augmenting extrinsic factors such as concentration or field amplitude. FIG. 13 shows a distinct peak in SLP at 16 nm for MNPs with narrow average size distribution. SLP values drop by ~30% for samples with broader average size distribution. The drop is especially substantial for 16 nm particles, the peak diameter for a 373 kHz field.

In vitro hyperthermia. In order to study the in vitro effect of magnetic fluid hyperthermia, ATP levels in Jurkat cells, as a measure of metabolic activity or cell viability, were compared. In general, cells experiencing MFH showed a decrease in viability compared to controls (no MFH). This trend was consistent with increasing MNP concentration (FIGS. 14A-14C). Monodisperse MNPs of three different diameters were compared. 16 nm MNPs, the optimal size for our chosen AMF as per the SLP data (FIG. 13), were compared with 12 and 13 nm MNPs. The decrease in viability is markedly greater for the 16 nm MNPs compared to 12 and 13 nm MNPs (FIG. 15). Also note, MNP concentration is slightly lower for 16 nm sample compared to 12 and 13 nm samples.

Discussion

TEM and analysis showed that the Fe$_3$O$_4$ MNPs were highly monodisperse and single phase, respectively. Additionally, magnetic properties of MNPs are superior, with saturation magnetization reaching as high as 75 emu/g for 16 nm MNPs (i.e. ~83% of bulk saturation value for magnetite (~90 emu/g). Due to the presence of ~0.5 nm layer of disordered spins on the surface of the MNPs that do not contribute to the total saturation magnetization of the sample, superparamagnetic particles often have lower saturation values compared to bulk. It also explains why the crystalline diameter, determined from XRD spectrum, is ~1 nm larger than the magnetic core diameter, determined by the Chantrell method. After transfer from organic to aqueous phase using the amphiphilic PMAO-PEG polymer, MNPs show exceptional stability in water (e.g., up to a year) and retain their superior magnetic properties up to a tested period of 5 months. The magnetic core diameters as determined using the Chantrell method confirm MNPs remain nearly monodisperse even after phase transfer (Table 3), suggesting no aggregation during the phase transfer process. Zeta potential as a function of pH shows MNPs display a near neutral surface charge across a wide pH range (2-12). This suggests MNPs are primarily stabilized via steric repulsion due to the surface PEG layer, and are less prone to adsorption form charged proteins or, in general, non-immunogenic. Hydrodynamic size measurements performed in cell culture medium (FIG. 10C) emphasize the biological relevance. For particles agglomerating in culture medium, the Brownian component of the relaxation, which depends on the hydrodynamic volume, can be blocked, decreasing the overall SLP output. MNP@PMAO-PEG are relatively stable for up to 96 hours in RPMI 1640+10% FBS cell culture medium, suggesting consequent decrease in SLP output due to particle agglomeration is not expected.

Cytotoxicity results confirm MNPs exhibit relatively low inherent toxicity in Jurkat cells (FIG. 11). Typically, the total amount of iron stores in the human body is approximately 3500 mg and the total amount of iron oxide used for diagnostic imaging is relatively small (~5.6 μgFe/ml). The maximum concentration used in our cytotoxicity experiments (up to 450 μgFe/ml) is far greater than the actual in vivo use. This ensures that we are measuring for cytotoxicity beyond current clinically tried levels. Overall, both viability and toxicity assays complement each other reasonably well, within the calculated error. Bright field images of cells (FIG. 12) at 20× and 60× magnification confirm that overall cell morphology is preserved after 24 hours of incubation with MNPs of various concentrations.

Comprehensive experimental SLP data as a function of both size and size distribution (FIG. 13) shows that, for the chosen AMF conditions (373 kHz and 14 kA/m), 16 nm monodisperse MNPs exhibit the optimum SLP. More importantly, a clear peak in the heating as a function of MNP size is demonstrated for the first time. Additionally, MNPs with broader average size distributions show an overall drop in the peak SLP value. The experimental data presented here provides strong validity to theoretical models of MFH, especially the need for size-tuned, monodisperse MNPs for maximizing SLP.

The in vitro therapeutic efficacy of MFH to induce cell death has been demonstrated in heating experiments with Jurkat cells as a function of both MNP concentration and size (FIGS. 14A-14C and 15). As expected, increasing MNP concentration increases heating rates; consequently reduction in % viability is also enhanced (FIG. 15). As described earlier, enhancing MFH by increasing MNP concentration, which is an extrinsic parameter, does not indicate an improvement in the overall therapeutic potency of MFH. The key result, however, is the significant decrease in % viability due to the optimum 16 nm sized MNPs compared to the 12 and 13 nm MNPs under the same AMF conditions. This result (FIG. 15) underscores the central idea of tailoring size for a specific frequency in order to intrinsically improve the therapeutic potency of MFH.

Systematic experiments show that magnetite MNPs, with optimal magnetic properties and tailored to a specific alternating magnetic field frequency (f=373 kHz) can show enhancement in MFH. Specifically, a peak in the heating rate or SLP as a function of MNP size has been clearly demonstrated and in vitro heating shows that optimized MNPs (16 nm) and narrow size distributions (a 30% difference in SLP is observed between σ~0.175 and σ~0.266) have maximum efficiency in reducing cell viability, suggesting our SLP data translates to cell populations. All this is achieved by synthesizing monodisperse MNPs via organic synthesis routes and successfully transferring them to aqueous phase using a biocompatible amphiphilic polymer. A characterization protocol ensures that the MNPs meet the criteria: (1) uniform shape and monodispersity, (2) phase purity, (3) stable magnetic properties approaching that of the bulk, (4) colloidal stability, (5) substantial shelf life and (6) pose no significant in vitro toxicity. This presents a way to tailor/synthesize optimal, biocompatible MNPs for MFH at any applied frequency.

Example 5

Analytical Methods Utilized to Characterize Nanoparticles

Transmission electron microscopy (TEM) was used to characterize the iron oxide cores. Core size and size distribution were measured from bright field TEM images using imageJ software (National Institutes of Health). Particle core diameters were binned to form a histogram, which was fitted using a log normal distribution (Equation 16)

$$g(d) = \frac{1}{\sigma d \sqrt{2\pi}} \exp - \frac{\left[\ln\left(\frac{d}{d_0}\right)\right]^2}{2\sigma^2} \quad (16)$$

where d is the core diameter measured by TEM, $d_0$ is the median core diameter, and $\exp(\sigma)$ is the geometric standard deviation. The geometric standard deviation is used to establish the bounds of confidence intervals for log-normally distributed variables; e.g. the 68% confidence interval has upper bound $d_0 * \exp(\sigma)$ and lower bound $d_0/\exp(\sigma)$.

Dynamic light scattering (DLS) measures the hydrodynamic diameter of nanoparticles. Hydrodynamic diameter includes the core diameter, any surfactants or polymers attached to the core and any hydration or counter-ion layer (if surface is charged) surrounding the outer surface. Hydrodynamic size increases if nanoparticles aggregate, or additional molecules, such as antibodies or other targeting moieties, are intentionally or unintentionally (non-specific adsorption of serum proteins) attached to the surface.

The "Z-average" value and PDI are quoted here, but hydrodynamic size can also be interpreted from the three intensity, volume and number-weighted distributions. All three distributions are included.

Vibrating sample magnetometer (VSM) measures the magnetization response of nanoparticles as a function of applied field (dc field). Saturation magnetization (Ms) and the core diameter—obtained from fitting the magnetization curve—are included. The magnetic core diameter is determined from magnetization data by fitting Equation 17:

$$\frac{M}{Ms} = \int_0^\infty L(\alpha) g(d) \, dd \quad (17)$$

Where $L(\alpha) \alpha \mathrm{Coth}(\alpha) - 1/\alpha$, $\alpha = vM_s\mu_0 H/k_b T$, v is the volume of the magnetic core, $M_s$ is the saturation magnetization of the particle in A/m, T is the sample temperature in Kelvin, $\mu_0$ is $4\pi \times 10^{-7}$ H/m, $\mu_0 H$ is the applied field (in Tesla), and $k_b$ is the Boltzmann constant, $1.38 \times 10^{-23}$ J/K. g(d) is a log-normal size distribution function, Equation 18:

$$g(d) = \frac{1}{\sigma d_c \sqrt{2\pi}} \exp - \frac{\left[\ln\left(\frac{d}{d_0}\right)\right]^2}{2\sigma^2} \quad (18)$$

$d_0$ is the median magnetic core diameter, and $\exp(\sigma)$ is the geometric standard deviation. The magnetic core diameter is often, though not always, similar to the iron oxide core diameter measured by TEM.

Magnetic particle spectrometry (MPS) measures the magnetization response of nanoparticles in an AC magnetic field.

All MPS measurements were performed with a sinusoidal excitation magnetic field at 25 kHz and 20 mT/$\mu_o$ amplitude. MPS measures the induced signal, which is proportional to the derivative of the total magnetic moment—m'(H(t), where m [Am$^2$] is the magnetic moment of the nanoparticles in the test sample. The m'(H(t) curves are presented in two ways: (1) intensity normalized—to compare the full width at half maximum (FEHM), and (2) mass normalized—to compare the magnetic signal per unit mass of iron. MPS also provides the harmonic spectrum of nanoparticles, which is the magnetization response of nanoparticles in the frequency domain.

Example 6

Colloidal and Magnetic Stability in Serum-Containing Medium

FIGS. 17A-2C graphically illustrate hydrodynamic size data from three samples (see Table 4) of PMAO-PEG nanoparticles (>20 nm) in RPMI+10% FBS cell culture medium: FIGS. 17A and 17B are comparative samples with 5 k Da PEG at a loading of 9% and 13%, respectively; FIG. 17C is an exemplary embodiment having 20 k Da PEG at a loading of 13%. In similar systems, FIGS. 18A-18C graphically illustrate magnetic particle spectrometry data from three samples of PMAO-PEG nanoparticles in DI water and serum-rich cell culture medium: FIG. 18A is a comparative sample of 25 nm core diameter coated with 5 k Da PEG at a loading of 9%; FIG. 18B is a comparative sample of 23 nm core diameter coated with 5 k Da PEG at a loading of 13%; and FIG. 18C is an exemplary embodiment of 25 nm core diameter coated with 20 k Da PEG at a loading of 13%. The insets of FIGS. 18A-3C show intensity-normalized MPS data.

TABLE 4

Nanoparticle characteristics from FIGS. 17A-17C and 18A-18C

| sample | d-core [nm] | m-PEG Mn [Da] | % PEG loading | d-hydro [nm] |
|---|---|---|---|---|
| a | 25 | 5,000 | 9 | 44 |
| b | 23 | 5,000 | 13 | 46 |
| c | 27 | 20,000 | 13 | 62 |

The SPION samples of FIGS. 18A-18C are within the optimum size range for MPI (23-27 nm, core dia.) and were coated with either one of three different PMAO-PEG polymers: PMAO-PEG(5 KDa), with ~9% or ~13% PEG loading and PMAO-PEG(20 KDa) with ~13% PEG loading. In contrast to the DLS data presented in FIGS. 17A-17C, MPS data provides insight into the relaxation behavior of SPIONs in the biological environment—together the two methods enable us to probe the physical changes in SPIONs that can affect MPS performance. In order to get a complete picture of the m'(H) plots, both forward and reverse scans are shown in FIGS. 18A-18C. SPIONs coated with PMAO-PEG(5 kDa) at 9% PEG loading (FIG. 18A) showed immediate degradation in m'(H) after dispersing in RPMI+10% FBS medium; the appearance of peaks at −10 mT/$\mu_o$ and +10 mT/$\mu_o$ suggest a high coercive field required for magnetization reversal, which occurs when SPIONs are interacting due to potential agglomeration. The colloidal stability data for the same sample presented in FIG. 18A confirms that SPIONs are indeed agglomerating. In contrast, the improvement in colloidal stability (FIG. 18B) of SPIONs coated with PMAO-PEG(5 kDa), but a higher PEG loading (PEG/PMAO=30; 13%), translates to MPS measurements (FIG. 18B), which show that m'(H) curve is relatively unperturbed even 24 hours post-RPMI dispersion. Finally, the effect of increasing PEG molecular weight from 5,000 Da to 20,000 Da (FIG. 18C)—without changing PEG density (PEG/PMAO=30; 13% PEG loading)—also preserves the native m'(H) response of SPIONs in serum-rich medium. Note that the core size of SPIONs tested in FIGS. 18A and 18C are identical, including their respective m'(H) curves in DI water. However, while the SPIONs coated with the 20,000 Da molecular weight PEG (PEG/PMAO=30; 13% PEG loading) performed excellent in cell culture medium, the 5,000 Da coated SPIONs, with a PEG/PMAO=20 (9% PEG loading) performed poorly.

These results show that colloidal stability—measured using DLS (FIGS. 17A-17C)—correlates directly with MPS signal (FIGS. 18A-18C). By preventing the SPION cores from agglomerating and magnetically interacting, we preserve the magnetization reversal characteristics of SPIONs, which forms the physical basis of signal generation in MPI. In summary, surface coatings play a critical role in preventing protein adsorption—important for long blood circulation—and preserving the MPS performance—important for acquiring images from circulating SPIONs—of MPI-optimized SPIONs in physiological environments.

Example 7

Improving Performance by Removing Aggregates or Clusters

FIG. 19A graphically illustrates the effect of centrifugation on the hydrodynamic diameter of PMAO-PEG nanoparticles. FIG. 19B graphically illustrates the mass (top) and intensity (bottom) of the PMAO-PEG nanoparticles evaluated in FIG. 19A by magnetic particle spectrometry.

In this section, we examine the critical role of surface coatings in preserving the relaxation properties of iron oxide cores—the fundamental properties responsible for MPI signal generation—and demonstrating significant improvements in MPS performance; critically, we will examine the effect of removing clustered SPIONs—often the product of phase transfers—on the MPS signal. Nanoparticle clusters were removed via a series of centrifugation steps, followed by careful extraction of the dispersed SPIONs ensuring the pelleted SPIONs remain unperturbed from pipetting; subsequently, the mean hydrodynamic diameter and MPS signal were monitored. For instance, it was found that the hydrodynamic size of 22.5 nm core diameter SPIONs progressively decreased post-centrifugation (FIG. 4A), while the MPS signal [V mgFe-1] and shape improved (FIG. 19B). Specifically, the mean hydrodynamic diameter decreased from 137.9 nm (PDI=0.33) to 54.8 nm (PDI=0.147), the mass normalized MPS signal (FIG. 19B, top) improved almost 1.7-fold, and the FWHM narrowed by ~24% (FIG. 19B-bottom). It is clear that the improved MPS performance is a direct consequence of removing clustered SPIONs and reduction in hydrodynamic size.

Example 8

MPS Performance as a Function of Core Diameter

FIGS. 20A and 20B graphically illustrate the magnetic particle spectrometry response to magnetic nanoparticle core diameter based on intensity (FIG. 20A) and mass (FIG.

20B). The core diameter varies as noted; the coating is PMAO-PEG (5 k MW). Data shows that nanoparticles smaller than 15 nm in core diameter have MPS performance worse than Resovist®—signal is nearly equivalent but FWHM is significantly broader/worse. Thus, nanoparticles smaller than 15 nm core diameter are inferior for MPI and other AC inductive measurement techniques. On the other hand, nanoparticles with core diameter between 23-27 nm are excellent for AC inductive measurements; example of 25.1 nm particles shown.

Example 9

Signal Linearity in Blood

FIGS. 21A and 21B graphically illustrate the magnetic response linearity of magnetic nanoparticles according to the disclosed embodiments in blood. Analyzed samples are described in Table 5.

Nanoparticles coated with PMAO-PEG(20 kDa) demonstrate signal stability and signal linearity in blood. Nanoparticles from the same batch of iron oxide cores (5-87; d-core=26.4 nm, sigma=0.06) were coated with either polymer batch 9-4 (PMAO-PEG(20 kDa) at 12.5% PEG loading) or 9-5 (PMAO-PEG(20 kDa) at 25% PEG loading). Iron concentration of PMAO-PEG coated samples was determined using ICP and dilution series in DI water and blood were prepared. After 24 hours of incubation in blood, magnetic signal induced in ac magnetic field (25 kHz and 20 mT/$\mu_0$) from both samples was linear with concentration and changed minimally compared to signal in DI water and 0 h incubation time-point in blood.

Results demonstrate the ability to stabilize large core diameter nanoparticles (>25 nm) in water and biological media, while preventing long-term aggregation and preserving nanoparticle relaxation dynamics that are critical for ac magnetic field detection and imaging applications.

TABLE 5

Nanoparticle characteristics of FIGS. 21A and 21B.

| Sample | Core | Polymer | m-PEG $M_n$ [Da] | TEM [nm] ($\sigma$) | % PEG loading | DLS [nm] (PDI) |
|---|---|---|---|---|---|---|
| 8-108 | 5-87 | 9-5 | 20,000 | 26.4 (0.06) | 25 | 71 (0.12) |
| 8-109 | 5-87 | 9-4 | 20,000 | 26.4 (0.06) | 12.5 | 67 (0.14) |

Example 10

Signal Stability after In Vivo Administration

FIG. 22 graphically illustrates magnetic signal stability in blood of exemplary nanoparticles in vivo (mice). Analyzed here is sample 8-175: nanoparticle core 9-71 (d-core=24.3 nm and sigma=0.13) coated with polymer batch 9-104 (PMAO loaded with 18.75% 20 kDa PEG). Nanoparticles were injected in the tail-vein of mice and allowed to circulate. Blood was drawn after 60 and 90 minutes of circulation and the nanoparticle-containing blood samples were placed in 25 kHz (20 mT/$\mu_0$ amplitude) ac magnetic field. The induced magnetic signal from nanoparticles in blood after 60 and 90 minutes of circulation showed little change, as characterized by the signal full-width at half maximum (FWHM).

Result indicates that colloidal stability and nanoparticle relaxation dynamics, critical for signal induction in ac magnetic fields, were preserved after in vivo administration.

Example 11

Tunable Blood Half-Life

Table 6 summarizes blood half-life data for comparative and exemplary nanoparticles.

TABLE 6

Blood half-life data

| Sample | Internal ID | PEG $M_n$ [Da] | % loading | TEM dia. [nm] ($\sigma$) | DLS dia.; z-avg. [nm] (PDI) | t-½ [min] |
|---|---|---|---|---|---|---|
| A | UW-17-86 | 5,000 | 9 | 19 (0.15) | 86 | 4 |
| B | UW-20-42 | 5,000 | 13 | 18 (0.09) | 42 | 18 |
| C (LSL) | 8-109 | 20,000 | 12.5 | 26.4 (0.06) | 67 (0.14) | 35 |
| D (LSL) | 8-157 | 20,000 | 25 | 24.3 (0.13) | 89 (0.18) | 80 |
| E (LSL) | 8-175 | 20,000 | 18.75 | 24.3 (0.13) | 78 (0.11) | 160 |

Results clearly showed that UW-20-42 had a longer circulation time (blood half-life) than UW-17-86 in mice; specifically, the blood half-life of UW-20-42 was ~18 minutes compared to ~4 minutes for UW-17-86. Since the core properties of the two samples were similar, the differences in circulation characteristics are likely due to the differences in surface coating and hydrodynamic diameter. Our results seem to agree with the general notion that blood half-life tends to increase with a decrease in hydrodynamic size. Furthermore, increasing the PEG loading from PEG(5 kDa)/PMAO of 20 (9%) to 30 (13%) significantly improves colloidal and magnetic signal stability of nanoparticles in serum-containing media (FIGS. 17A-17C and 18A-18C); consequently, increasing the blood half-life.

Increasing the PEG molecular weight from 5 kDa to 20 kDa improves blood half-life. In general, the observed improvements in blood half-life are directly related to the enhanced stability of nanoparticles coated with 20 kDa PEG. Nanoparticles coated with 20 kDa PEG at 12.5% PEG loading (sample C) showed a 2-fold increase in blood half-life compared to nanoparticles coated with 5 kDa PEG at a similar PEG loading of 13% (sample B). Further increasing PEG(20 kDa) loading to 18.75% (sample E) and 25% (sample D) increased blood half-life to 160 minutes and 80 minutes, respectively.

Results indicate that (1) increasing PEG molecular weight from 5 kDa to 20 kDa significantly improves blood half-life and (this is still preliminary work) (2) optimal % loading, when using PEG(20 kDa), may exist between 12.5% and 25%.

Example 12

Synthesis and Characterization of Comparative and Exemplary Nanoparticles

Table 7 summarizes the composition of comparative and exemplary nanoparticles disclosed herein. Table 8 summarizes the characteristics of the nanoparticles of Table 7. The synthesis of the polymers, cores, and coated nanoparticles of Tables 7 and 8 are disclosed in detail below.

TABLE 7

Composition of comparative and exemplary nanoparticles.

| Sample ID | Polymer ID | Core ID | PEG1 [Mn] Da | PEG2 [Mn] Da | Other | % PEG1 | % PEG2 | % Other |
|---|---|---|---|---|---|---|---|---|
| 8-43 | ak051313 | 5-87 | 20,000 | — | — | 13 | — | — |
| 8-66 | 5-153 | 5-87 | 5,000 | — | — | 50 | — | — |
| 8-103 | 9-3 | 5-206 | 10,000 | — | — | 25 | — | — |
| 8-104 | 9-1 | 5-87 | 10,000 | — | — | 50 | — | — |
| 8-105 | 9-2 | 5-87 | 10,000 | 5,000 | — | 25 | 25 | — |
| 8-106 | 9-3 | 5-87 | 10,000 | — | — | 25 | — | — |
| 8-107 | 9-4 | 5-87 | 20,000 | — | — | 12.5 | — | — |
| 8-108 | 9-5 | 5-87 | 20,000 | — | — | 25 | — | — |
| 8-109 | 9-4 | 5-87 | 20,000 | — | — | 12.5 | — | — |
| 8-117 | 9-19 | 5-87 | 20,000 | 5,000 | — | 12.5 | 25 | — |
| 8-118 | 9-20 | 5-87 | 20,000 | — | N,N-dimethyl-1,3-propanediamine | 12.5 | — | 37.5 |
| 8-157 | 9-55 | 9-71 | 20,000 | — | — | 25 | — | — |
| 8-175 | 9-104 | 9-71 | 20,000 | — | — | 18.75 | — | — |
| 8-180 | 9-105 | 9-71 | 20,000 | — | — | 25 | — | — |

TABLE 8

Characteristics of comparative and exemplary nanoparticles.

| Sample ID | TEM-dC [nm] ($\sigma$) | DLS-dH [nm] (PDI) | MPS-FWHM [mT/$\mu_0$] | MPS-signal [m$^3$/gFe] | VSM-Ms (Saturation Magnetization) [kA/m] |
|---|---|---|---|---|---|
| 8-43 | 26.4 (0.06) | 72 (0.12) | 4.7 | 2.20E−05 | 330 |
| 8-66 | 26.4 (0.06) | 52 (0.16) | 5.5 | 2.00E−05 | 318 |
| 8-103 | 25.8 (0.12) | 73 (0.15) | 5.5 | 1.60E−05 | 335 |
| 8-104 | 26.4 (0.06) | 65 (0.11) | 5.7 | | |
| 8-105 | 26.4 (0.06) | 66 (0.13) | 5.9 | | |
| 8-106 | 26.4 (0.06) | 66 (0.11) | 5.4 | | |
| 8-107 | 26.4 (0.06) | 75 (0.14) | 5.1 | 1.52E−05 | |
| 8-108 | 26.4 (0.06) | 71 (0.12) | 5 | 1.65E−05 | 263 |
| 8-109 | 26.4 (0.06) | 67 (0.14) | 5 | 1.65E−05 | 263 |
| 8-117 | 26.4 (0.06) | 77 (0.15) | 5.3 | | |
| 8-118 | 26.4 (0.06) | 79 (0.13) | 5.3 | | |
| 8-157 | 24.3 (0.13) | 89 (0.18) | 4.8 | 2.79E−05 | 343 |
| 8-175 | 24.3 (0.13) | 78 (0.11) | 4.8 | 2.52E−05 | 358 |
| 8-180 | 24.3 (0.13) | 89 (0.14) | 5.2 | 2.52E−05 | 367 |

TEM = Transmission Electron Microscopy
DLS = Dynamic Light Scattering
MPS = Magnetic Particle Spectroscopy; all measurements at 25 kHz and 20 mT/$\mu_0$ amplitude
VSM = Vibrating Sample Magnetometry
Note:
A small MPS-FWHM and large MPS-signal indicate preferred performance.

Materials. Poly(maleic anhydride-alt-1-octadecene) (average Mn 30,000-50,000 Da) was obtained from Sigma-Aldrich. Triethylamine (99%), triphenylphosphine (99%), N,N-dimethyl-1,3-propanediamine, were obtained from Alfa Aesar. Benzyltriethylammonium chloride (>98%) p-toluenesulfonyl chloride (>99%) was obtain from Tokyo Chemical Industry CO, LTD. Sodium hydroxide, magnesium sulfate (anhydrous), sodium sulfate (anhydrous) and methylene chloride (HPLC grade) were obtained from Fisher Scientific. Hexane (mixture of isomers), chloroform, acetone were HPLC grade and obtained from Sigma-Aldrich. Diethyl ether was obtained from J. T. Baker. Ethanol (200 proof) was obtained from Decon Labs. Phosphoric acid (85%), sulfuric acid were obtained from Macron. Water used in any experiment was purified at 18.2 MOhm-cm. SUB A-SEAL® septum were obtained from Chemglass. Dialysis tubing, Spectra/Por Dialysis Membrane Biotech CE tubing MWCO: 50 kD, flat width=31 mm, was obtained from Spectrum Laboratories, Inc.

mPEG-NH2 of various MWs were either purchased from JenKem or produced from the appropriate mPEG-OH by formation of the tosylate, displacement with sodium azide and reduction of the azide to the amine with triphenylphosphine.

PMAO (30-50 kDa) loaded 50% with mPEG-NH2 (5 kDa) (5-153). To a 100 mL round bottom flask was added PMAO (211 mg), mPEG-NH2 (MW=5 kDa, 3.00 g, 0.600 mmol) and dichloromethane (24 mL) followed by triethylamine (0.335 mL). The reaction mixture was stirred for 4 days under argon and then concentrated. The resulting residue was dissolved with water (50 mL) and 30% aqueous sodium hydroxide (0.5 mL) and stirred for two days. Dialysis using 50 kDa mw cut off dialysis tubes was performed against water for 24 hours with 8 water changes. The polymer solution was lyophilized to give 50% mPEG(5 kDa)-NH-PMAO (2.73 g).

PMAO (30-50 kDa) loaded 100% with mPEG-NH2 (5 kDa) (5-161). To a 100 mL round bottom flask was added PMAO (175.4 mg), mPEG-NH2 (MW=5 kDa, 5.00 g, 1.00 mmol) and dichloromethane (30 mL) followed by triethylamine (0.280 mL). The reaction mixture was stirred overnight under argon. EDC-HCl (383 mg, 2 mmol) was added and stirring was continued for three days. The reaction mixture was concentrated and then dried in vacuo for 30 minutes. The resulting residue was dissolved with water (100 mL) and stirred for 15 minutes. Dialysis of the polymer solution using 50 kDa mw cut off dialysis tubes was performed against water for 24 hours with 8 water changes. The polymer solution was lyophilized to give 100% mPEG(5 kDa)-NH-PMAO (3.468 g).

PMAO (30-50 kDa) loaded 50% with mPEG-NH2 (10 kDa) (9-01). To a 25 mL round bottom flask was added PMAO (70 mg), mPEG-NH2 (MW=10 kDa, 2.00 g, 0.200 mmol) and dichloromethane (12 mL) followed by triethylamine (0.111 mL). The reaction mixture was stirred for 3 days under argon and then concentrated. The resulting residue was dissolved with water (100 mL) and 30% aqueous sodium hydroxide (0.5 mL) and stirred for 24 hours. Dialysis using 50 kDa mw cut off dialysis tubes was performed against water for 48 hours with 8 water changes. The polymer solution was lyophilized to give 50% mPEG (10 kDa)-NH-PMAO (1.738 g).

PMAO (30-50 kDa) loaded 25% with mPEG-NH2 (5 kDa) and 25% with mPEG-NH2 (10 kDa) (9-02). To a 25 mL round bottom flask was added PMAO (70 mg), mPEG-NH2 (MW=5 kDa, 0.50 g, 0.100 mmol), mPEG-NH2 (MW=10 kDa, 1.00 g, 0.100 mmol) and dichloromethane (8 mL) followed by triethylamine (0.111 mL). The reaction mixture was stirred for 3 days under argon and then concentrated. The resulting residue was dissolved with water (90 mL) and 30% aqueous sodium hydroxide (0.5 mL) and stirred for 1 hour. Dialysis using 50 kDa mw cut off dialysis tubes was performed against water for 24 hours with 8 water changes. The polymer solution was lyophilized to give 25% (5 kDa) and 25% (10 kDa) mPEG-NH-PMAO (1.401 g).

PMAO (30-50 kDa) loaded 25% with mPEG-NH2 (10 kDa) (9-03). To a 25 mL round bottom flask was added PMAO (70 mg), mPEG-NH2 (MW=10 kDa, 1.00 g, 0.100 mmol) and dichloromethane (8 mL) followed by triethylamine (0.111 mL). The reaction mixture was stirred for 3 days under argon and then concentrated. The resulting residue was dissolved with water (90 mL) and 30% aqueous sodium hydroxide (0.5 mL) and stirred for 1 hour. Dialysis using 50 kDa mw cut off dialysis tubes was performed against water for 24 hours with 8 water changes. The polymer solution was lyophilized to give 25% (5 kDa) and 25% (10 kDa) mPEG-NH-PMAO (1.023 g).

PMAO (30-50 kDa) loaded 12.5% with mPEG-NH2 (20 kDa) (9-04). To a 25 mL round bottom flask was added PMAO (70 mg), mPEG-NH2 (MW=20 kDa, 1.00 g, 0.050 mmol) and dichloromethane (8 mL) followed by triethylamine (0.028 mL). The reaction mixture was stirred for 2 days under argon and then concentrated. The resulting residue was dissolved with water (125 mL) and 30% aqueous sodium hydroxide (0.5 mL) and stirred for 18 hours. Dialysis using 50 kDa mw cut off dialysis tubes was performed against water for 24 hours with 8 water changes. The polymer solution was lyophilized to give 12.5% (20 k) mPEG-NH-PMAO (1.143 g).

PMAO (30-50 kDa) loaded 25% with mPEG-NH2 (20 kDa) (9-05). To a 100 mL round bottom flask was added PMAO (70 mg), mPEG-NH2 (MW=20 kDa, 2.00 g, 0.100 mmol) and dichloromethane (20 mL) followed by triethylamine (0.056 mL). The reaction mixture became very viscous. The reaction mixture was stirred for 6 days under argon and then concentrated. The resulting residue was dissolved with water (125 mL) and 30% aqueous sodium hydroxide (0.5 mL) and stirred for 18 hours. To get the white residue to completely dissolve an additional portion of water (125 mL) was added and the mixture was stirred for another 2 hours. Dialysis using 50 kDa mw cut off dialysis tubes was performed against water for 24 hours with 8 water changes. The polymer solution was lyophilized to give 25% (20 k) mPEG-NH-PMAO (1.895 g).

PMAO (30-50 kDa) loaded 12.5% with mPEG-NH2 (20 kDa) and 25% with mPEG-NH2 (5 kDa) (9-19). To a 25 mL round bottom flask was added PMAO (70 mg), mPEG-NH2 (MW=20 kDa, 1.00 g, 0.050 mmol) and dichloromethane (8 mL) followed by triethylamine (0.028 mL). The reaction mixture was stirred for 2 hrs under argon. The other mPEG-NH2 (MW=5 kDa, 0.500 g, 0.100 mmol) was added. The reaction mixture was stirred for 5 days and then concentrated. The resulting residue was dissolved with water (125 mL) and 30% aqueous sodium hydroxide (0.5 mL) and stirred for 18 hours. Dialysis using 50 kDa mw cut off dialysis tubes was performed against water for 24 hours with 8 water changes. The polymer solution was lyophilized to give 12.5% (20 k) and 25% (5 kDa) mPEG-NH-PMAO (1.425 g).

PMAO (30-50 kDa) loaded 12.5% with mPEG-NH2 (20 kDa) and 37.5% with N,N-dimethyl-1,3-propane diamine (9-19). To a 100 mL round bottom flask was added PMAO (70 mg), mPEG-NH2 (MW=20 kDa, 1.00 g, 0.050 mmol) and dichloromethane (20 mL) followed by triethylamine (0.028 mL). The reaction mixture was stirred for 3 days under argon. The N,N-dimethyl-1,3-propane diamine (0.019 mL, 0.150 mmol) was added. The reaction mixture was stirred for 2 days and then concentrated. The resulting residue was dissolved with water (125 mL) and 30% aqueous sodium hydroxide (0.5 mL) and stirred for 18 hours. Dialysis using 50 kDa mw cut off dialysis tubes was performed against water for 24 hours with 8 water changes. The polymer solution was lyophilized to give 37.5% N,N-dimethyl-1,3-propane diamine and 12.5% (20 k) mPEG-NH-PMAO (1.035 g).

PMAO (30-50 kDa) loaded 12.5% with mPEG-NH2 (20 kDa) and 87.5% with mPEG-NH2 (2 k) (9-40). To a 100 mL round bottom flask was added PMAO (47 mg), mPEG-NH2 (MW=20 kDa, 0.667 g, 0.033 mmol) and dichloromethane (27 mL) followed by triethylamine (0.149 mL). The reaction mixture was stirred overnight under argon. The other mPEGNH2 (2 k, 0.467 mg, 0.233 mmol) was added and stirring continued for 1 hour. EDC-HCl (51 mg, 0.266 mmol) was added and stirring was continued for three days. The reaction mixture was concentrated and then dried in vacuo for 30 minutes. The resulting residue was dissolved with water (85 mL). Sodium hydroxide (100 mg) was added and stirred for 20 hours. Dialysis of the polymer solution using 50 kDa mw cut off dialysis tubes was performed against water for 48 hours with 8 water changes. The polymer solution was lyophilized to give 12.5%(20 k) and 87.5% (2 k) mPEG-NH-PMAO (775 mg).

PMAO (30-50 kDa) loaded 25% with mPEG-NH2 (20 kDa) (9-55). To a 100 mL round bottom flask was added PMAO (70 mg), mPEG-NH2 (MW=20 kDa, 2.00 g, 0.100 mmol) and dichloromethane (25 mL) followed by triethylamine (0.056 mL). The reaction mixture became very viscous. The reaction mixture was stirred for 9 days under argon and then concentrated. The resulting residue was dissolved with water (225 mL) and sodium hydroxide (108 mg) was added. The solution was stirred for 3 days. Dialysis using 50 kDa mw cut off dialysis tubes was performed against water for 24 hours with 8 water changes. The polymer solution was lyophilized to give 25% (20 k) mPEG-NH-PMAO (1.6982 g).

PMAO (30-50 kDa) loaded 25% with mPEG-NH2 (20 kDa) (9-96). To a 100 mL round bottom flask was added PMAO (70 mg), mPEG-NH2 (MW=20 kDa, 2.00 g, 0.100 mmol) and dichloromethane (25 mL) followed by triethylamine (0.056 mL). The reaction mixture was stirred for 6 days under argon and then concentrated. The resulting residue was dissolved with water (225 mL) and sodium hydroxide (150 mg) and stirred for 2 days. Dialysis using 50 kDa mw cut off dialysis tubes was performed against water for 24 hours with 8 water changes. The polymer solution was lyophilized to give 25% (20 k) mPEG-NH-PMAO (1.957 g).

PMAO (30-50 kDa) loaded 37.5% with mPEG-NH2 (20 kDa) (9-97). To a 100 mL round bottom flask was added PMAO (70 mg), mPEG-NH2 (MW=20 kDa, 3.00 g, 0.150 mmol) and dichloromethane (37.5 mL) followed by triethylamine (0.084 mL). The reaction mixture was stirred for 6 days under argon and then filtered and concentrated. The resulting residue was dissolved with water (200 mL) and sodium hydroxide (110 mg) and stirred for 20 hours. Dialysis using 50 kDa mw cut off dialysis tubes was performed against water for 48 hours with 8 water changes. The polymer solution was lyophilized to give 37.5% (20 k) mPEG-NH-PMAO (2.3834 g).

PMAO (30-50 kDa) loaded 25% with mPEG-NH2 (20 kDa) (9-101). To a 500 mL round bottom flask was added PMAO (601 mg), mPEG-NH2 (MW=20 kDa, 17.134 g, 0.857 mmol) and dichloromethane (214.2 mL) followed by triethylamine (0.478 mL). The reaction mixture was stirred for 6 days under argon and then concentrated. The resulting residue was dissolved with water (1600 mL) and sodium hydroxide (1.50 g) and stirred for 4 days. The resulting polymer solution was divided into four portions for batch dialysis using 50 kDa mw cut off dialysis tubes was performed against water for 24 hours with 8 water changes. The polymer solution was lyophilized to give 25% (20 k) mPEG-NH-PMAO (15.875 g).

PMAO (30-50 kDa) loaded 18.75% with mPEG-NH2 (20 kDa) (9-104). To a 20 mL vial was added PMAO (7 mg), mPEG-NH2 (MW=20 kDa, 150 mg, 0.007 mmol) and dichloromethane (2 mL) followed by triethylamine (0.006 mL). The reaction mixture was stirred for 6 days under argon and then concentrated. The polymer was dissolved in chloroform was used in phase transfer without further purification.

PMAO (30-50 kDa) loaded 25% with mPEG-NH2 (20 kDa) (9-105). To a 100 mL round bottom flask was added PMAO (70 mg), mPEG-NH2 (MW=20 kDa, 2.00 g, 0.100 mmol) and dichloromethane (25 mL) followed by triethylamine (0.056 mL). The reaction mixture was stirred for 6 days under argon. The polymer solution was used in phase transfer without further purification.

Examples of Phase Transfer Procedures

Nanoparticle washing procedure. Iron oxide nanoparticle cores were synthesized according to U.S. Patent Application Publication No. 2013/0149539, the disclosure of which is hereby incorporated by reference in its entirety. Nanoparticles from crude synthesis batch were washed with a mixture of hexanes, acetone and ethyl acetate. After separating iron oxide cores with a magnet, supernatant containing excess oleic acid and octadecene was decanted. To iron oxide core pellet, hexane was added and sonicated in water-bath sonicator for 10 minutes. After dispersion in hexanes, acetone and ethyl acetate solvent mixture was added to precipitate nanoparticles and then separated with magnet. Supernatant from the separated nanoparticles was decanted and washing procedure was repeated for an additional 3 times. After last wash, iron oxide cores were dried under high vacuum before phase transfer with PMAO-PEG polymer.

Phase Transfer of Washed Nanoparticles.

8-43: nanoparticle core 5-87 phase transferred with Ak051313. 40 mg of polymer batch ak051313 (PMAO loaded with 13% 20 kDa mPEG-OH; Mn~6.37E5 g/mol) was dissolved in 3 mL chloroform and mixed with 1 mL of washed iron oxide nanoparticles (batch 5-87) dispersed in chloroform. The final polymer and nanoparticle concentrations were 10 mg/mL and 2.5 mg/mL, respectively, dispersed in a total of 4 mL chloroform in a 20 mL glass vial (approximately 187 PMAO-PEG polymer units per iron oxide nanoparticle, assuming 26.3 nm core diameter). The mixture was sonicated for 60 minutes, followed by rotary evaporation to dryness. The solid nanoparticle and polymer mixture was further dried under high vacuum for 60 minutes. To the 20 mL glass vial, 10 mL of 1×TAE buffer was added, and nanoparticle and polymer solid mixture was dispersed by sonication for 60 minutes. The solution was checked for any visible aggregates and sonicated for additional time if necessary. The PMAO-PEG coated nanoparticles dispersed in 1×TAE buffer were stirred for 24 hours using magnetic stir bar, then filtered with 200 nm nylon syringe filter. To remove excess polymer and salt, filtered PMAO-PEG coated nanoparticles were passed through S-200 sephacryl gel column (GE Healthcare) pre-rinsed with DI water.

Hydrodynamic diameter (Z-average)=72 nm; PDI=0.12

8-66: nanoparticle core 5-87 phase transferred with 5-153. 230 mg of polymer batch 5-153 (PMAO loaded with 50% 5 kDa mPEG-NH2; Mn~6.10E5 g/mol) was dissolved in 11.5 mL chloroform (20 mg/mL concentration). 10 mg of washed iron oxide nanoparticles (batch 5-87) were dispersed in 1 mL chloroform (10 mg/mL concentration) using a water-bath sonicator. To a 20 mL glass vial containing 0.75 mL of 20 mg/mL polymer solution dissolved in chloroform, was added 1 mL of iron oxide nanoparticles dispersed in chloroform. An additional 0.25 mL of chloroform was added to bring the final volume up to 2 mL, which diluted the polymer concentration to 7.5 mg/mL and iron oxide nanoparticle concentration to 5 mg/mL (approximately 73 PMAO-PEG polymer units per iron oxide nanoparticle, assuming 26.3 nm core diameter). The nanoparticle and polymer mixture in chloroform was sonicated for 60 minutes and then stirred using a magnetic stir bar. After 24 hours of stirring, chloroform was evaporated using rotary evaporation, giving a nanoparticle and polymer solid mixture that was dried overnight under high vacuum. To the 20 mL glass vial containing dried nanoparticle and polymer solid mixture, 4 mL of 1×TAE buffer was added, and nanoparticle and polymer solid mixture was dispersed by sonication for 60 minutes. After sonication, the solution was checked for any visible aggregates and sonicated for additional time if necessary. The PMAO-PEG coated nanoparticles dispersed in 1×TAE buffer were stirred for 24 hours using magnetic stir bar, then filtered with 200 nm nylon syringe filter. To remove excess polymer and salt, filtered PMAO-PEG coated nanoparticles were passed through S-200 sephacryl gel column (GE Healthcare) pre-rinsed with DI water. To remove aggregates, nanoparticles were centrifuged at 5,000 rcf for 15 minutes and supernatant containing aggregate-free nanoparticles was carefully collected.

Hydrodynamic diameter (Z-average)=52 nm; PDI=0.16

8-103: nanoparticle core 5-206 phase transferred with 9-3. 155.2 mg of polymer batch 9-3 (PMAO loaded with 25% 10 kDa mPEG-NH2; Mn~6.10E5 g/mol) was dissolved in 9.1 mL chloroform (17 mg/mL concentration). 10 mg of washed iron oxide nanoparticles (batch 5-206) were dispersed in 1 mL chloroform (10 mg/mL concentration) using a water-bath sonicator. To a 20 mL glass vial containing 2.79 mL of 17 mg/mL polymer solution dissolved in chloroform, was added 1 mL of iron oxide nanoparticles dispersed in chloroform. An additional 0.21 mL of chloroform was added to bring the final volume up to 4.0 mL, which diluted the polymer concentration to 11.86 mg/mL and iron oxide nanoparticle concentration to 2.5 mg/mL (approximately 232 PMAO-PEG polymer units per iron oxide nanoparticle, assuming 26.3 nm core diameter). The nanoparticle and polymer mixture in chloroform was sonicated for 60 minutes and then stirred using a magnetic stir bar. After 24 hours of stirring, chloroform was evaporated using rotary evaporation, giving a nanoparticle and polymer solid mixture that was dried overnight under high vacuum. To the 20 mL glass vial containing dried nanoparticle and polymer solid mixture, 10 mL of 1×TAE buffer was added, and nanoparticle and polymer solid mixture was dispersed by sonication for 60 minutes. After sonication, the solution was checked for any visible aggregates and sonicated for additional time if necessary. The PMAO-PEG coated nanoparticles dispersed in 1×TAE buffer were stirred for 24 hours using magnetic stir bar, then filtered with 200 nm nylon syringe filter. To remove excess polymer and salt, filtered PMAO-PEG coated nanoparticles were passed through S-200 sephacryl gel column (GE Healthcare) pre-rinsed with DI water. To remove aggregates, nanoparticles were centrifuged at 5,000 rcf for 15 minutes and supernatant containing aggregate-free nanoparticles was carefully collected.

Hydrodynamic diameter (Z-average)=73 nm; PDI=0.15

8-104: nanoparticle core 5-87 phase transferred with 9-1. 149 mg of polymer batch 9-1 (PMAO loaded with 50% 10 kDa mPEG-NH2; Mn~1.18E6 g/mol) was dissolved in 4.3 mL chloroform (35 mg/mL concentration). 10 mg of washed iron oxide nanoparticles (batch 5-87) were dispersed in 1 mL chloroform (10 mg/mL concentration) using a water-bath sonicator. To a 40 mL glass vial containing 2.64 mL of 35 mg/mL polymer solution dissolved in chloroform, was added 1 mL of iron oxide nanoparticles dispersed in chloroform. An additional 0.36 mL of chloroform was added to bring the final volume up to 4.0 mL, which diluted the polymer concentration to 23 mg/mL and iron oxide nanoparticle concentration to 2.5 mg/mL (approximately 234 PMAO-PEG polymer units per iron oxide nanoparticle, assuming 26.3 nm core diameter). The nanoparticle and polymer mixture in chloroform was sonicated for 60 minutes and then stirred using a magnetic stir bar. After 24 hours of stirring, chloroform was evaporated using rotary evaporation, giving a nanoparticle and polymer solid mixture that was dried overnight under high vacuum. To the 40 mL glass vial containing dried nanoparticle and polymer solid mixture, 10 mL of 1×TAE buffer was added, and nanoparticle and polymer solid mixture was dispersed by sonication for 60 minutes. After sonication, the solution was checked for any visible aggregates and sonicated for additional time if necessary. The PMAO-PEG coated nanoparticles dispersed in 1×TAE buffer were stirred for 24 hours using magnetic stir bar, then filtered with 200 nm nylon syringe filter. To remove excess polymer and salt, filtered PMAO-PEG coated nanoparticles were passed through S-200 sephacryl gel column (GE Healthcare) pre-rinsed with DI water. To remove aggregates, nanoparticles were centrifuged at 5,000 rcf for 15 minutes and supernatant containing aggregate-free nanoparticles was carefully collected.

Hydrodynamic diameter (Z-average)=65 nm; PDI=0.11

8-105: nanoparticle core 5-87 phase transferred with 9-2. 190 mg of polymer batch 9-2 (PMAO loaded with 25% 10 kDa mPEG-NH2 and 25% 5 kDa mPEG-NH2; Mn~8.95E5 g/mol) was dissolved in 5.4 mL chloroform (35 mg/mL concentration). 10 mg of washed iron oxide nanoparticles (batch 5-87) were dispersed in 1 mL chloroform (10 mg/mL concentration) using a water-bath sonicator. To a 20 mL glass vial containing 2 mL of 35 mg/mL polymer solution dissolved in chloroform, was added 1 mL of iron oxide nanoparticles dispersed in chloroform. An additional 1 mL of chloroform was added to bring the final volume up to 4.0 mL, which diluted the polymer concentration to 17.5 mg/mL and iron oxide nanoparticle concentration to 2.5 mg/mL (approximately 234 PMAO-PEG polymer units per iron oxide nanoparticle, assuming 26.3 nm core diameter). The nanoparticle and polymer mixture in chloroform was sonicated for 60 minutes and then stirred using a magnetic stir bar. After 24 hours of stirring, chloroform was evaporated using rotary evaporation, giving a nanoparticle and polymer solid mixture that was dried overnight under high vacuum. To the 20 mL glass vial containing dried nanoparticle and polymer solid mixture, 10 mL of 1×TAE buffer was added, and nanoparticle and polymer solid mixture was dispersed by sonication for 60 minutes. After sonication, the solution was checked for any visible aggregates and sonicated for additional time if necessary. The PMAO-PEG coated nanoparticles dispersed in 1×TAE buffer were stirred for 24 hours using magnetic stir bar, then filtered with 200 nm nylon syringe filter. To remove excess polymer and salt, filtered PMAO-PEG coated nanoparticles were passed through S-200 sephacryl gel column (GE Healthcare) pre-rinsed with DI water. To remove aggregates, nanoparticles were centrifuged at 5,000 rcf for 15 minutes and supernatant containing aggregate-free nanoparticles was carefully collected.

Hydrodynamic diameter (Z-average)=66 nm; PDI=0.13

8-106: nanoparticle core 5-87 phase transferred with 9-3. 152.2 mg of polymer batch 9-3 (PMAO loaded with 25% 10 kDa mPEG-NH2; Mn~6.10E5 g/mol) was dissolved in 9.1 mL chloroform (17 mg/mL concentration). 10 mg of washed iron oxide nanoparticles (batch 5-87) were dispersed in 1 mL chloroform (10 mg/mL concentration) using a water-bath sonicator. To a 20 mL glass vial containing 2.79 mL of 17 mg/mL polymer solution dissolved in chloroform, was added 1 mL of iron oxide nanoparticles dispersed in chloroform. An additional 0.21 mL of chloroform was added to bring the final volume up to 4.0 mL, which diluted the polymer concentration to 11.86 mg/mL and iron oxide nanoparticle concentration to 2.5 mg/mL (approximately 234 PMAO-PEG polymer units per iron oxide nanoparticle, assuming 26.3 nm core diameter). The nanoparticle and polymer mixture in chloroform was sonicated for 60 minutes and then stirred using a magnetic stir bar. After 24 hours of stirring, chloroform was evaporated using rotary evaporation, giving a nanoparticle and polymer solid mixture that was dried overnight under high vacuum. To the 20 mL glass vial containing dried nanoparticle and polymer solid mixture, 10 mL of 1×TAE buffer was added, and nanoparticle and polymer solid mixture was dispersed by sonication for 60 minutes. After sonication, the solution was checked for any visible aggregates and sonicated for additional time if necessary. The PMAO-PEG coated nanoparticles dispersed in 1×TAE buffer were stirred for 24 hours using magnetic stir bar, then filtered with 200 nm nylon syringe filter. To remove excess polymer and salt, filtered PMAO-PEG coated nanoparticles were passed through S-200 sephacryl gel column (GE Healthcare) pre-rinsed with DI water. To remove aggregates, nanoparticles were centrifuged at 5,000 rcf for 15 minutes and supernatant containing aggregate-free nanoparticles was carefully collected.

Hydrodynamic diameter (Z-average)=66 nm; PDI=0.11

8-107: nanoparticle core 5-87 phase transferred with 9-4. 111 mg of polymer batch 9-4 (PMAO loaded with 12.5% 20 kDa mPEG-NH2; Mn~6.10E5 g/mol) was dissolved in 14.8 mL chloroform (7.5 mg/mL concentration). 10 mg of washed iron oxide nanoparticles (batch 5-87) were dispersed in 1 mL chloroform (10 mg/mL concentration) using a water-bath sonicator. To a 20 mL glass vial containing 6.33 mL of 7.5 mg/mL polymer solution dissolved in chloroform, was added 1 mL of iron oxide nanoparticles dispersed in chloroform. An additional 2.67 mL of chloroform was added to bring the final volume up to 10 mL, which diluted the polymer concentration to 4.75 mg/mL and iron oxide nanoparticle concentration to 1 mg/mL (approximately 234 PMAO-PEG polymer units per iron oxide nanoparticle, assuming 26.3 nm core diameter). The nanoparticle and polymer mixture in chloroform was sonicated for 60 minutes and then stirred using a magnetic stir bar. After 24 hours of stirring, chloroform was evaporated using rotary evaporation, giving a nanoparticle and polymer solid mixture that was dried overnight under high vacuum. To the 20 mL glass vial containing dried nanoparticle and polymer solid mixture, 10 mL of 1×TAE buffer was added, and nanoparticle and polymer solid mixture was dispersed by sonication for 60 minutes. After sonication, the solution was checked for any visible aggregates and sonicated for additional time if necessary. The PMAO-PEG coated nanoparticles dispersed in 1×TAE buffer were stirred for 24 hours using magnetic stir bar, then filtered with 200 nm nylon syringe filter. To remove excess polymer and salt, filtered PMAO-PEG coated nanoparticles were passed through S-200 sephacryl gel column (GE Healthcare) pre-rinsed with DI water. To remove aggregates, nanoparticles were centrifuged at 5,000 rcf for 15 minutes and supernatant containing aggregate-free nanoparticles was carefully collected.

Hydrodynamic diameter (Z-average)=75 nm; PDI=0.14

8-108: nanoparticle core 5-87 phase transferred with 9-5. 114 mg of polymer batch 9-5 (PMAO loaded with 25% 20 kDa mPEG-NH2; Mn~1.18E6 g/mol) was dissolved in 11.4 mL chloroform (10 mg/mL concentration). 10 mg of washed iron oxide nanoparticles (batch 5-87) were dispersed in 1 mL chloroform (10 mg/mL concentration) using a water-bath sonicator. To a 40 mL glass vial containing 9.25 mL of 10 mg/mL polymer solution dissolved in chloroform, was added 1 mL of iron oxide nanoparticles dispersed in chloroform. After mixing the polymer and nanoparticle solutions, the final polymer concentration was 9.25 mg/mL and iron oxide nanoparticle concentration to 1 mg/mL (approximately 234 PMAO-PEG polymer units per iron oxide nanoparticle, assuming 26.3 nm core diameter). The nanoparticle and polymer mixture in chloroform was sonicated for 60 minutes and then stirred using a magnetic stir bar. After 24 hours of stirring, chloroform was evaporated using rotary evaporation, giving a nanoparticle and polymer solid mixture that was dried overnight under high vacuum. To the 40 mL glass vial containing dried nanoparticle and polymer solid mixture, 10 mL of 1×TAE buffer was added, and nanoparticle and polymer solid mixture was dispersed by sonication for 60 minutes. After sonication, the solution was checked for any visible aggregates and sonicated for additional time if necessary. The PMAO-PEG coated nanoparticles dispersed in 1×TAE buffer were stirred for 24 hours using magnetic stir bar, then filtered with 200 nm nylon syringe filter. To remove excess polymer and salt, filtered PMAO-PEG coated nanoparticles were passed through S-200 sephacryl gel column (GE Healthcare) pre-rinsed with DI water. To remove aggregates, nanoparticles were centrifuged at 5,000 rcf for 15 minutes and supernatant containing aggregate-free nanoparticles was carefully collected.

Hydrodynamic diameter (Z-average)=71 nm; PDI=0.12

8-109: nanoparticle core 5-87 phase transferred with 9-4. 111 mg of polymer batch 9-4 (PMAO loaded with 12.5% 20 kDa mPEG-NH2; Mn~6.10E5 g/mol) was dissolved in 14.8 mL chloroform (7.5 mg/mL concentration). 8.44 mg of washed iron oxide nanoparticles (batch 5-87) were dispersed in 0.84 mL chloroform (10 mg/mL concentration) using a water-bath sonicator. To a 40 mL glass vial containing 8.1 mL of 7.5 mg/mL polymer solution dissolved in chloroform, was added 0.84 mL of iron oxide nanoparticles dispersed in chloroform. After mixing the polymer and nanoparticle solutions, the final polymer concentration was 6.80 mg/mL and iron oxide nanoparticle concentration to 0.94 mg/mL (approximately 351 PMAO-PEG polymer units per iron oxide nanoparticle, assuming 26.3 nm core diameter). The nanoparticle and polymer mixture in chloroform was sonicated for 60 minutes and then stirred using a magnetic stir bar. After 24 hours of stirring, chloroform was evaporated using rotary evaporation, giving a nanoparticle and polymer solid mixture that was dried overnight under high vacuum. To the 40 mL glass vial containing dried nanoparticle and polymer solid mixture, 9.4 mL of 1×TAE buffer was added, and nanoparticle and polymer solid mixture was dispersed by sonication for 60 minutes. After sonication, the solution was checked for any visible aggregates and sonicated for additional time if necessary. The PMAO-PEG coated nanoparticles dispersed in 1×TAE buffer were stirred for 24 hours using magnetic stir bar, then filtered with 200 nm nylon syringe filter. To remove excess polymer and salt, filtered PMAO-PEG coated nanoparticles were passed through S-200 sephacryl gel column (GE Healthcare) pre-rinsed with DI water. To remove aggregates, nanoparticles were centrifuged at 5,000 rcf for 15 minutes and supernatant containing aggregate-free nanoparticles was carefully collected.

Hydrodynamic diameter (Z-average)=67 nm; PDI=0.14

8-117: nanoparticle core 5-87 phase transferred with 9-19. 75 mg of polymer batch 9-19 (PMAO loaded with 12.5% 20 kDa mPEG-NH2 and 25% 5 kDa mPEG-NH2; Mn~8.95E5 g/mol) was dissolved in 7.5 mL chloroform (10 mg/mL concentration). 6 mg of washed iron oxide nanoparticles (batch 5-87) were dispersed in 0.6 mL chloroform (10 mg/mL concentration) using a water-bath sonicator. To a 40 mL glass vial containing 4.2 mL of 10 mg/mL polymer solution dissolved in chloroform, was added 0.6 mL of iron oxide nanoparticles dispersed in chloroform. An additional 1.2 mL of chloroform was added to bring the final volume to 6.0 mL, which diluted polymer concentration to 7 mg/mL and iron oxide nanoparticle concentration to 1 mg/mL (approximately 233 PMAO-PEG polymer units per iron oxide nanoparticle, assuming 26.3 nm core diameter). The nanoparticle and polymer mixture in chloroform was sonicated for 60 minutes and then stirred using a magnetic stir bar. After 24 hours of stirring, chloroform was evaporated using rotary evaporation, giving a nanoparticle and polymer solid mixture that was dried overnight under high vacuum. To the 40 mL glass vial containing dried nanoparticle and polymer solid mixture, 6 mL of 1×TAE buffer was added, and nanoparticle and polymer solid mixture was dispersed by sonication for 60 minutes. After sonication, the solution was checked for any visible aggregates and sonicated for additional time if necessary. The PMAO-PEG coated nanoparticles dispersed in 1×TAE buffer were stirred for 24 hours using magnetic stir bar, then filtered with 200 nm nylon syringe filter. To remove excess polymer and salt, filtered PMAO-PEG coated nanoparticles were passed through S-200 sephacryl gel column (GE Healthcare) pre-rinsed with DI water. To remove aggregates, nanoparticles were centrifuged at 5,000 rcf for 15 minutes and supernatant containing aggregate-free nanoparticles was carefully collected.

Hydrodynamic diameter (Z-average)=77 nm; PDI=0.15

8-118: nanoparticle core 5-87 phase transferred with 9-20. 56 mg of polymer batch 9-20 (PMAO loaded with 12.5% 20 kDa mPEG-NH2 and 37.5% N,N-dimethyl-1,3-propanediamine; Mn~6.19E5 g/mol) was dissolved in 7.5 mL chloroform (10 mg/mL concentration). 6 mg of washed iron oxide nanoparticles (batch 5-87) were dispersed in 0.6 mL chloroform (10 mg/mL concentration) using a water-bath sonicator. To a 40 mL glass vial containing 2.91 mL of 10 mg/mL polymer solution dissolved in chloroform, was added 0.6 mL of iron oxide nanoparticles dispersed in chloroform. An additional 2.5 mL of chloroform was added to bring the final volume to 6.0 mL, which diluted polymer concentration to 4.85 mg/mL and iron oxide nanoparticle concentration to 1 mg/mL (approximately 342 polymer units per iron oxide nanoparticle, assuming 26.3 nm core diameter). The nanoparticle and polymer mixture in chloroform was sonicated for 60 minutes and then stirred using a magnetic stir bar. After 24 hours of stirring, chloroform was evaporated using rotary evaporation, giving a nanoparticle and polymer solid mixture that was dried overnight under high vacuum. To the 40 mL glass vial containing dried nanoparticle and polymer solid mixture, 6 mL of 1×TAE buffer was added, and nanoparticle and polymer solid mixture was dispersed by sonication for 60 minutes. After sonication, the solution was checked for any visible aggregates and sonicated for additional time if necessary. The PMAO-PEG coated nanoparticles dispersed in 1×TAE buffer were stirred for 24 hours using magnetic stir bar, then filtered with 200 nm nylon syringe filter. To remove excess polymer and salt, filtered PMAO-PEG coated nanoparticles were passed through S-200 sephacryl gel column (GE Healthcare) pre-rinsed with DI water. To remove aggregates, nanoparticles were centrifuged at 5,000 rcf for 15 minutes and supernatant containing aggregate-free nanoparticles was carefully collected.

Hydrodynamic diameter (Z-average)=79 nm; PDI=0.13

8-157: nanoparticle core 9-71 phase transferred with 9-55. 936 mg of polymer batch 9-55 (PMAO loaded with 25% 20 kDa mPEG-NH2; Mn~1.18E6 g/mol) was dissolved in 46.8 mL chloroform (20 mg/mL concentration). 93.6 mg of washed iron oxide nanoparticles (batch 9-71) were dispersed in 9.36 chloroform (10 mg/mL concentration) using a water-bath sonicator. To a 250 mL round bottom flask containing 46.8 mL of 20 mg/mL polymer solution dissolved in chloroform, was added 9.36 mL of iron oxide nanoparticles dispersed in chloroform. An additional 46.8 mL of chloroform was added to the polymer and nanoparticle mixture to bring the final volume up to 103 mL, which diluted polymer concentration to 9.1 mg/mL and iron oxide nanoparticle concentration to 0.91 mg/mL (approximately 245 PMAO-PEG polymer units per iron oxide nanoparticle, assuming 26 nm core diameter). The nanoparticle and polymer mixture in chloroform was sonicated for 60 minutes and then stirred using a magnetic stir bar. After 48 hours stirring, chloroform was evaporated using rotary evaporation, giving a nanoparticle and polymer solid mixture that was dried overnight under high vacuum. To 250 mL round bottom flask containing dried nanoparticle and polymer solid mixture, 100 mL of 1×TAE buffer was added and nanoparticle and polymer solid mixture was dispersed by sonication for 120 minutes. After sonication, the solution was checked for any visible aggregates and sonicated for additional time if necessary. PMAO-PEG coated nanoparticles dispersed in 1×TAE buffer were stirred for 48 hours using magnetic stir bar, then filtered with 200 nm nylon syringe filter. PMAO-PEG coated nanoparticles were dialyzed against deionized (DI) water using 50,000 MWCO dialysis tubes to remove salts, with water four water changes over a 24-hour period. To remove excess polymer, filtered and dialyzed PMAO-PEG coated nanoparticles were passed through S-200 sephacryl gel column (GE Healthcare) pre-rinsed with DI water. To remove aggregates, nanoparticles were centrifuged at 5,000 rcf for 15 minutes and supernatant containing aggregate-free nanoparticles was carefully collected.

Hydrodynamic diameter (Z-average)=89 nm; PDI=0.18

8-175: nanoparticle core 5-87 phase transferred with 9-104. 157 mg of polymer batch 9-104 (PMAO loaded with 18.75% 20 kDa mPEG-NH2; Mn~8.95E5 g/mol) was dissolved in 7.85 mL chloroform (20 mg/mL concentration). 10 mg of washed iron oxide nanoparticles (batch 9-71) were dispersed in 1.0 mL chloroform (10 mg/mL concentration) using a water-bath sonicator. To a 40 mL glass vial containing 3.75 mL of 20 mg/mL polymer solution dissolved in chloroform, was added 1 mL of iron oxide nanoparticles dispersed in chloroform. An additional 5.25 mL of chloroform was added to bring the final volume to 10 mL, which diluted polymer concentration to 7.5 mg/mL and iron oxide nanoparticle concentration to 1 mg/mL (approximately 241 PMAO-PEG polymer units per iron oxide nanoparticle, assuming 26 nm core diameter). The nanoparticle and polymer mixture in chloroform was sonicated for 60 minutes and then stirred using a magnetic stir bar. After 24 hours of stirring, chloroform was evaporated using rotary evaporation, giving a nanoparticle and polymer solid mixture that was dried overnight under high vacuum. To the 40 mL glass vial containing dried nanoparticle and polymer solid mixture, 10 mL of deionized (DI) water was added, and nanoparticle and polymer solid mixture was dispersed by sonication for 60 minutes. After sonication, the solution was checked for any visible aggregates and sonicated for additional time if necessary. The PMAO-PEG coated nanoparticles dispersed in DI water were stirred for 24 hours using magnetic stir bar, then filtered with 200 nm nylon syringe filter. To remove excess polymer, filtered PMAO-PEG coated nanoparticles were passed through S-200 sephacryl gel column (GE Healthcare) pre-rinsed with DI water. To remove aggregates, nanoparticles were centrifuged at 5,000 rcf for 15 minutes and supernatant containing aggregate-free nanoparticles was carefully collected.

Hydrodynamic diameter (Z-average)=78 nm; PDI=0.11

8-180: nanoparticle core 9-71 phase transferred with 9-105. Polymer solution of batch 9-105 (PMAO loaded with 25% 20 kDa mPEG-NH2; Mn~1.18E6 g/mol) in dichloromethane was evaporated to dryness using rotary evaporation and further dried under high vacuum for 24 hours. Dried polymer was weighed and dissolved in chloroform at 20 mg/mL concentration. Washed iron oxide nanoparticles (batch 9-71) were weighed and dispersed in chloroform at 10 mg/mL concentration using a water-bath sonicator. To a 100 mL round bottom flask containing 20 mL of 20 mg/mL polymer solution dissolved in chloroform, was added 4 mL of iron oxide nanoparticles dispersed in chloroform. An additional 16 mL of chloroform was added to the polymer and nanoparticle mixture to bring the final volume up to 40 mL, which diluted polymer concentration to 10 mg/mL and iron oxide nanoparticle concentration to 1 mg/mL (approximately 245 PMAO-PEG polymer units per iron oxide nanoparticle, assuming 26 nm core diameter). The nanoparticle and polymer mixture in chloroform was sonicated for 60 minutes and then stirred for 48 hours using a magnetic stir bar. After stirring, the magnetic stir bar was removed and 40 mL of nanoparticle and polymer solution was divided equally into four (4) 40 mL glass vials (10 ml/vial). Chloroform from each was evaporated using rotary evaporation, giving a nanoparticle and polymer solid mixture that was dried for 30 minutes under high vacuum. To each 40 mL vial, 10 mL of deionized (DI) water was added and nanoparticle and polymer solid mixture was dispersed by sonication for 60 minutes. After 60 minutes of sonication, the solution was checked for any visible aggregates and sonicated for additional time if necessary. PMAO-PEG coated nanoparticles dispersed in DI water were stirred for 48 hours using magnetic stir bar, then filtered with 200 nm nylon syringe filter. To remove excess polymer, filtered PMAO-PEG coated nanoparticles were passed through S-200 sephacryl gel column (GE Healthcare) pre-rinsed with DI water.

Hydrodynamic diameter (Z-average)=89 nm; PDI=0.14

While illustrative embodiments have been illustrated and described, it will be appreciated that various changes can be made therein without departing from the spirit and scope of the invention.

The invention claimed is:

1. A plurality of nanoparticles, each nanoparticle comprising:
   a core comprising iron oxide, wherein the core has a diameter of 15 nm to 30 nm; and
   a coating surrounding the core, the coating comprising a PMAR-PEG copolymer having a poly(maleic anhydride alt-$H_2C=CH-R_1$) (PMAR) portion and a plurality of polyethylene glycol (PEG) portions each with a molecular weight ($M_n$) of 10,000 Da or greater;
   wherein $R_1$ is a hydrophobic moiety.

2. The nanoparticles of claim 1, wherein the molecular weight ($M_n$) of the PEG portions is 40,000 Da or less.

3. The nanoparticles of claim 1, wherein the cores are monodisperse, as defined by a geometric standard deviation of less than 1.35.

4. The nanoparticles of claim 1, wherein the plurality of nanoparticles is 100 or more nanoparticles.

5. The nanoparticles of claim 1, wherein the PMAR portion has a molecular weight (Mn) of 30,000 Da to 50,000 Da.

6. The nanoparticles of claim 1, wherein the PMAR-PEG copolymer has 1% to 50% PEG based on the number of PEG portions attached to the available number of carboxylates of the PMAR portion, given the presence of 2 carboxylates per maleate in the PMAR portion.

7. The nanoparticles of claim 1, wherein the nanoparticle relaxation or magnetic moment reversal of each core is independent of an adjacent nanoparticle.

8. The nanoparticles of claim 1, wherein the coating is attached to the core by a mechanism selected from the group consisting of covalent bonding, ionic bonding, van der Waals forces, and hydrophobic/hydrophobic interactions.

9. The nanoparticles of claim 1, wherein the coating consists essentially of the PMAR-PEG copolymer.

10. The nanoparticles of claim 1, wherein at least a portion of the plurality of nanoparticles comprise a single core surrounded with the coating.

11. The nanoparticles of claim 1, wherein the PMAR portion is poly(maleic anhydride alt-1-octadecene) (PMAO).

12. The nanoparticles of claim 1, wherein $R_1$ is alkyl.

13. The nanoparticles of claim 1, wherein the $R_1$ is a C6 to C18 hydrocarbon.

14. The nanoparticles of claim 1, wherein the diameter of the core is 18 nm or greater.

15. The nanoparticles of claim 14, wherein the nanoparticles have a Z-average hydrodynamic diameter of less than 150 nm.

16. The nanoparticles of claim 1, wherein the diameter of the core is 23 nm or greater and the molecular weight (Mn) of the PEG portions is 20,000 Da or greater.

17. The nanoparticles of claim 16, wherein the nanoparticles have a Z-average hydrodynamic diameter of less than 250 nm.

18. The nanoparticles of claim 1, wherein the nanoparticles are magnetic tracers configured to be introduced into a subject.

19. A method, comprising applying a magnetic field to a plurality of nanoparticles according to claim 1.

20. The method of claim 19, wherein the method is a magnetic particle imaging method and the magnetic field comprises a spatially varying magnetic field with a field-free region and a time varying magnetic field.

21. The method of claim 19, wherein the method is a magnetic hyperthermia method and the magnetic field is an alternating magnetic field configured to heat the plurality of nanoparticles.

22. The method of claim 19, wherein the method is a magnetic sentinel lymph node biopsy method, the method further comprising a step of detecting a magnetic response to the magnetic field.

* * * * *